United States Patent
Burns et al.

(10) Patent No.: US 6,379,929 B1
(45) Date of Patent: Apr. 30, 2002

(54) CHIP-BASED ISOTHERMAL AMPLIFICATION DEVICES AND METHODS

(75) Inventors: Mark A. Burns; David T. Burke; Brian N. Johnson, all of Ann Arbor, MI (US); John D. DeNuzzio, Chapel Hill; Wayne F. Beyer, Jr., Bahama, both of NC (US)

(73) Assignee: The Regents of the University of Michigan, Ann Arbor, MI (US)

( * ) Notice: Subject to any disclaimer, the term of this patent is extended or adjusted under 35 U.S.C. 154(b) by 0 days.

(21) Appl. No.: 08/974,738

(22) Filed: Nov. 19, 1997

Related U.S. Application Data

(60) Provisional application No. 60/031,590, filed on Nov. 20, 1996.

(51) Int. Cl.⁷ ............................................... C12P 19/34
(52) U.S. Cl. ..................... 435/91.2; 435/91.1; 436/501
(58) Field of Search .............................. 435/91.1, 91.2; 436/501; 935/77, 78

(56) References Cited

U.S. PATENT DOCUMENTS

| | | | |
|---|---|---|---|
| 5,006,749 A | * 4/1991 | White | 310/323 |
| 5,270,184 A | 12/1993 | Walker et al. | 435/91.2 |
| 5,451,500 A | 9/1995 | Stapleton | 435/6 |
| 5,455,166 A | 10/1995 | Walker | 435/91.2 |
| 5,498,392 A | 3/1996 | Wilding et al. | 422/68.1 |
| 5,587,128 A | 12/1996 | Wilding et al. | 422/50 |
| 5,589,136 A | 12/1996 | Northrup et al. | 422/102 |
| 5,591,609 A | 1/1997 | Auerbach | 435/91.2 |
| 5,614,389 A | 3/1997 | Auerbach | 435/91.2 |
| 5,616,478 A | 4/1997 | Chetverin et al. | 435/91.2 |
| 5,639,423 A | 6/1997 | Northrup et al. | 122/50 |
| 5,712,124 A | 1/1998 | Walker et al. | 435/91.2 |
| 5,733,733 A | 3/1998 | Auerbach | 435/6 |
| 5,872,010 A | * 2/1999 | Karger et al. | 436/173 |

FOREIGN PATENT DOCUMENTS

| | | |
|---|---|---|
| EP | 0329 822 B1 | 8/1989 |
| EP | 0329 822 A2 | 8/1989 |
| EP | 0684 315 A1 | 11/1995 |
| WO | WO 88/10315 | 12/1988 |
| WO | WO 94/03472 | 2/1994 |

OTHER PUBLICATIONS

Van Brunt, Bio/Technology, vol. 8, pp. 291–294, 1990.*
Matthews et al., Analytical Biochemistry, vol. 169, pp 1–25, 1988.*

(List continued on next page.)

*Primary Examiner*—Ardin H. Marschel
(74) *Attorney, Agent, or Firm*—Fulbright & Jaworski

(57) ABSTRACT

Disclosed are methods and compositions for isothermal amplification of nucleic acids in a microfabricated substrate. Methods and compositions for the analysis of isothermally amplified nucleic acids in a microfabricated substrate are disclosed as well. The microfabricated substrates and isothermal amplification and detection methods provided are envisioned for use in various diagnostic methods, particularly those connected with diseases characterized by altered gene sequences or gene expression.

48 Claims, 7 Drawing Sheets

OTHER PUBLICATIONS

Burke et al., "Microfabrication technologies for integrated nucleic acid analysis" *Genome Research*, 7:189–197, 1997.

Burns et al., "Microfabricated structures for integrated DNA analysis" *Proc. Natl. Acad. Sci. USA*, 93:5556–5561, 1996.

Cheng et al., "Analysis of ligase chain reaction products amplified in a silicon–glass chip using capillary electrophoresis" *J. Chrom. A*, 732:151–158, 1996.

Cheng et al., "Chip PCR. II. Investigation of different PCR amplification systems in microfabricated silicon–glass chips" *Nucl. Acid. Res.*, 24:380–385, 1996.

Guatelli et al., "Isothermal, in vitro amplification of nucleic acids by a multienzyme reaction modeled after retroviral replication" *Proc. Natl. Acad. Sci. USA*, 87:1874–1878, 1990.

Lizardi et al., "Exponential amplication of recombinant–RNA hybridization probes" *BioTechnology*, 6:1197–1202, 1988.

Walker, et al., "Strand displacement amplification–an isothermal, in vitro DNA amplification technique" *Nucl. Acid. Res.*, 7:1691–1696, 1992.

Walker et al., "Isothermal in vitro amplification of DNA by a restriction enzyme/DNA polymerase system" *Proc. Natl. Acad. Sci. USA*, 89:392–396, 1992.

Wilding et al., "PCR in a silicon microstructure," *Clin. Chem.*, 40:1815–1818, 1994.

Wilding et al., "Thermal cycling and surface passivation of micromachined devices for PCR" *Clin. Chem.*, 41:1367–1368, 1995.

Wooley et al., "Functional integration of PCR amplification and capillary electrophoresis in a microfabricated DNA analysis device" *Anal. Chem.*, 68:4081–4086, 1996.

Yap and McGee "Slide PCR: DNA amplification from cell samples on microscopic glass slides" *Nucl. Acid. Res.*, 19:4294, 1991.

* cited by examiner

CHIP-BASED ISOTHERMAL AMPLIFICATION DEVICES AND METHODS

The present application claims the priority of co-pending U.S. Provisional Patent Application Ser. No. 60/031,590, filed Nov. 20, 1996, the entire disclosure of which is incorporated herein by reference without disclaimer. The government owns rights in the present invention pursuant to grant number R01-HG01044 from the National Institutes of Health.

BACKGROUND OF THE INVENTION

1. Field of the Invention

The present invention relates generally to the field of molecular biology, and relates to methods for amplifying nucleic acid target sequences in microfabricated devices. It particularly relates to isothermal methods for amplifying nucleic acid targets in microfabricated devices. The present invention also relates to methods of detecting and analyzing nucleic acids in microfabricated devices.

2. Description of Related Art

In vitro nucleic acid amplification techniques have provided powerful tools for detection and analysis of small amounts of nucleic acids. The extreme sensitivity of such methods has lead to their development in the fields of diagnosis of infectious and genetic diseases, isolation of genes for analysis, and detection of specific nucleic acids as in forensic medicine.

Nucleic acid amplification techniques may be grouped according to the temperature requirements of the procedure. Certain nucleic acid amplification methods, such as the polymerase chain reaction (PCR™—Saiki et al., 1985), ligase chain reaction (LCR—Wu et al., 1989; Barringer et al., 1990; Barony, 1991), transcription-based amplification (Kwoh et al., 1989) and restriction amplification (U.S. Pat. No. 5,102,784), require temperature cycling of the reaction between high denaturing temperatures and somewhat lower polymerization temperatures. In contrast, methods such as self-sustained sequence replication (3SR; Guatelli et al., 1990), the Qβ replicase system (Lizardi et al., 1988), and Strand Displacement Amplification (SDA—Walker et al., 1992a, 1992b; U.S. Pat. No. 5,455,166) are isothermal reactions that are conducted at a constant temperature, which is typically much lower than the reaction temperatures of temperature cycling amplification methods.

The SDA reaction initially developed was conducted at a constant temperature between about 37° C. and 42° C. (U.S. Pat. No. 5,455,166). This was because the exo⁻klenow DNA polymerase and the restriction endonuclease (e.g., HindII) are mesophilic enzymes that are thermolabile (temperature sensitive) at temperatures above this range. The enzymes that drive the amplification are therefore inactivated as the reaction temperature is increased.

Methods for isothermal Strand Displacement Amplification, which may be performed in a higher temperature range than conventional SDA (about 50° C. to 70° C., "thermophilic SDA"), were later developed. Thermophilic SDA is described in European Patent Application No. 0 684 315 and employs thermophilic restriction endonucleases that nick the hemimodified restriction endonuclease recognition/cleavage site at high temperature and thermophilic polymerases that extend from the nick and displace the downstream strand in the same temperature range.

Photolithographic micromachining of silicon has been used to construct high-throughput integrated fluidic systems for a variety of chemical analyses. This technology is of particular interest for the development of devices for analysis of nucleic acids, as in their conventional formats such analyses are typically labor- and material-intensive. Ideally, all of the processing steps of the amplification reaction would be conducted on the microfabricated device to produce a completely integrated nucleic acid analysis system for liquid transfer, mixing, reaction and detection that requires minimal operator intervention.

Silicon and glass devices are economically attractive because the associated micromachining methods are, essentially, photographic reproduction techniques. Silicon structures are processed using batch fabrication and lithographic techniques. These processes resemble those of printing where many features may be printed at the same time. These processes permit the simultaneous fabrication of thousands of parts in parallel, thus reducing system costs enormously. Today, silicon fabrication techniques are available to simultaneously fabricate micrometer and submicrometer structures on large-area wafers (100 cm$^2$), yielding millions of devices per wafer and may be used to process either silicon or glass substrates.

These characteristics have led to the proposal of silicon and glass as a candidate technology for the construction of high-throughput DNA analysis devices (Woolley and Mathies, 1994; Northrup et al., 1993; Effenhauser et al., 1994). As mechanical materials, both silicon and glass have well-known fabrication characteristics (Petersen, 1982). Microfabricated devices for biochemical and fluidic manipulation are undergoing development in many laboratories around the world (Ramsey et al., 1995; McIntyre 1996). Over the past 10 years, a number of microfluidic devices have been developed that allow the construction of miniaturized "chemical reactors."Individual components of the system such as pumps (Esashi et al., 1989; Zengerle et al., 1992; Matsumoto and Colgate, 1990; Folta et al., 1992); valves (Esashi et al., 1989, Ohnstein et al., 1990; Smits, 1990); fluid channels (Pfahler et al., 1990); chromatographic and liquid electrophoresis separation systems (Terry et al., 1979; Harrison et al., 1992b–g; Manz et al., 1991; Manz et al., 1992) are available. Although an objective of several research groups, complete silicon-fabricated nucleic acids analysis systems are still at the earliest stages of development.

Other components that have been microfabricated which are applicable to nucleic acid analysis include elements for gel electrophoresis (Zeineh and Zeineh, 1990; Heller and Tullis, 1992; Effenhauser et al., 1994; Woolley and Mathies, 1994, 1995; Webster et al., 1996); capillary electrophoresis (Manz et al. 1992, 1995; Effenhauser et al., 1993; Fan and Harrison, 1994; Jacobsen et al., 1994a; 1994b; Jacobson and Ramsey, 1995; Ocvirk et al., 1995; von Heeren et al., 1996); synthetic oligonucleotide arrays (Fodor et al., 1993; Schena et al., 1995; Hacia et al., 1996); continuous flow pumps (Lintel, 1988; Esashi et al., 1989; Matsumoto and Colgate, 1990; Nakagawa et al., 1990; Pfahler et al., 1990; Smits, 1990; Wilding et al, 1994; Olsson et al., 1995); discrete drop pumps (Burns et al., 1996); enzymatic reaction chambers (Northrup et al., 1994; Wilding et al., 1994b; Cheng et al., 1996); optical/radiation detectors (Belau et al., 1983; Wouters and van Sprakelaar, 1993; Webster et al., 1996); and multicomponent systems (Harrison et al., 1992, 1995; Northrup et al. 1994; Jacobsob and Ramsey 1996).

To date, a number of devices have been micromachined, including pumps and valves (Gravensen et al., 1993; Manz et al., 1994; Colgate and Matsumoto, 1990, Sammorco et al, 1996); reaction chambers (Woolley and Mathies, 1994;

Wilding et al., 1994); and separation and detection systems (Weber and May, 1989, Northrup et al., 1993, Harrison et al., 1993; Manz et al., 1992; Jacobson et al., 1994; Schoonevald et al., 1991; Van den Berg and Bergveld, 1995; Woolley et al., 1995). Some of these have been recently integrated together to build pharmaceutical drug closing systems (Lammerink et al., 1993; Miyake et al., 1993) and other microchemical systems (Nakagawa et al., 1990; Washizu, 1992; Van den Berg and Bergveld, 1995). One device is an integrated glass system combining DNA restriction enzyme digestion and capillary electrophoresis (Jacobson and Ramsey 1996). An alternative format using high-density arrays of synthesized oligodeoxynucleotides has been demonstrated as a DNA sequence detector (Fodor et al., 1993; Hacia et al., 1996).

Nucleic acid targets have been successfully amplified by the PCR™ on such microfabricated devices, often referred to as "chips" (U.S. Pat. No. 5,498,392; Woolley et al., 1996; Shoffner et al., 1995; Cheng et al., 1996; Wilding et al., 1994; U.S. Pat. No. 5,589,136; U.S. Pat. No. 5, 639,423; U.S. Pat. No. 5,587,128, U.S. Pat. No. 5,451,500) and LCR (Cheng et al., 1996; U.S. Pat. No. 5,589,136). Evaporation due to repeated exposure to high temperatures during thermocycling is a problem. Evaporation during PCR™ has been controlled by immersing the channel in oil such that the open ends are covered, but this makes recovery of the amplified sample difficult.

SUMMARY OF THE INVENTION

The present invention overcomes the foregoing evaporation and recovery drawbacks, and other deficiencies inherent in the prior art, by providing compositions and methods for use in the isothermal amplification of nucleic acids in microfabricated devices. In contrast to the difficulties previously perceived to exist and the prejudices in the art, the inventors found isothermal amplification of nucleic acids using microfabricated devices or "chips" to be surprisingly effective. In fact, the chip-based isothermal amplification of the present invention was discovered to be efficient at previously untested low temperatures, despite potentially negative effects of surface chemistry and other proposed problems, such as stagnant temperature gradients, reduced diffusion and mixing, and inhibition of enzyme activity.

The invention thus generally provides an apparatus, system, device or chip, or a plurality thereof, with isothermally regulated reaction chambers, methods of constructing single-chip and multiple-chip analytical systems, and methods for using such devices, chips and systems in the isothermal amplification of nucleic acids. The invention also provides for the analysis of the amplification products using, e.g., sequencing, gel separation, and/or detection of the amplification products in microfabricated devices. Further methods of the invention therefore include laboratory methods connected with nucleic acid analysis and clinical methods connected with the diagnosis and prognosis of disease states.

First provided by the invention are devices, chips, wafers or an analytical apparatus or system(s), generally of a microfabricated or micromachined type, for use in the isothermal amplification of selected nucleic acids. Certain preferred devices utilize the silicon chip or silicon wafer formats. In preferred embodiments, the devices of the present invention are "microdevices", preferably defining micromachined structures for use with nanoliter volumes.

The apparati, devices or chips of the invention generally comprise a microfabricated substrate or housing defining at least a first transport channel, or microdroplet transport channel, operably connected to at least a first reaction chamber, and at least a first means for isothermally regulating the temperature of the reaction chamber.

The "means for isothermally regulating the temperature of the reaction chamber" may be an element, such as a particular resistor, combination of resistors, feed-back temperature detector, and/or circuitry for temperature control, that has not been previously used in conjunction with a microfabricated device or chip for use in nucleic acid amplification. More preferably, the "means" for isothermally regulating the temperature of the reaction chamber will be a "programmable means". That is, a series of executable and controlled steps, preferably in the form of a computer program, the implementation of which results in the control of the temperature of the reaction chamber within narrow limits, such that the temperature is "substantially constant". These computer microprocessor or programmable means, although readily prepared by those of skill in the art, have not previously been proposed for use in combination with a microfabricated nucleic acid amplification device.

The microfabricated substrate of the device, chip or system is generally constructed so that application of a fluid in one or more transport channels will result in the fluid being conveyed at least to the reaction chamber. Accordingly, the microfabricated substrate inherently has a "flow-directed fabrication". The flow-directed fabrication or construction may be based upon gravitational attraction, thermal gradients, gas or liquid pressure differences, differences in hydrophobic and hydrophilic surface structures, electrowetting, and/or differences in the dielectric constant between reagent fluids applied to the substrate and the air or surrounding media. The manner in which a directional flow capability is provided to the substrate is not critical to the invention, so long as the substrate, device or system ultimately allows for the controlled manipulation of liquids or fluids applied thereto, and effective merging and mixing where appropriate.

In the context of this invention, a "reaction" or "amplification" generally refers to reactions involving nucleic acid biomolecules, such as RNA and DNA. "Nucleic acid amplification" generally refers to the process of increasing the concentration of nucleic acid, and in particular, the concentration of a selected nucleic acid and/or a defined piece of a selected nucleic acid. "Amplified or amplification products" or "amplicons" generally define the products resulting from execution of a nucleic acid amplification reaction.

As used herein, the term "an isothermal amplification reaction" refers to a nucleic acid amplification reaction that is conducted at a substantially constant temperature. It will be understood that this definition by no means excludes certain, preferably small, variations in temperature but is rather used to differentiate the isothermal amplification techniques from other amplification techniques known in the art that basically rely on "cycling temperatures" in order to generate the amplified products. Thus, the present invention is distinguished from PCR, which fundamentally rests on the temperature cycling phenomenon.

It will be further understood that although the isothermal amplification reactions of the present invention will generally be conducted at a substantially constant temperature, the overall execution of the amplification, diagnostic or prognostic methods of the invention may nonetheless require certain steps to be conducted at different temperatures. For example, moving fluids or microdroplets through the different channels or chambers defined on the microfabricated substrate, and/or merging and mixing samples and reagents, may involve alterations in temperature, e.g., as may be achieved via the use of defined heating elements.

The microfabricated substrate or housing of the invention may be fabricated from any one of a number of suitable materials. The materials will preferably be of the type that can be manipulated to define the channels, reaction chambers and other components necessary for conducting the amplification methods, and yet will be stable enough to permit repeated use in such methods once the defining components have been etched or otherwise imparted onto the substrate. Certain preferred examples include, but are not limited to, silicon, quartz and glass.

The transport channels or "microdroplet transport channels" defined in the substrate are generally pathways, whether straight, curved, single, multiple, in a network, etc., through which liquids, fluids and/or gases may be passively or actively transported. The channels are generally etched into the silicon, quartz, glass or other supporting substrate. The present invention requires the presence of at least a first channel that functions to allow the transport of a fluid sample into the reaction chamber. It will be understood that such a channel need not be of a significant minimum length, and that the term "channel" therefore refers to a fluid-conveying section in functional terms, rather than to defining a structure that is necessarily long and pipe-like.

The one or more channels in the substrate connect the various components, i.e., keep components "in communication" and more particularly, "in fluidic communication" and still more particularly, "in liquid communication." Such components include, but are not limited to, gas-intake channels and gas vents. In certain other aspects of the invention "microdroplet transport channels" may refer to channels configured (in microns) so as to accommodate "microdroplets."

While it is not intended that the present invention be limited by precise dimensions of the channels or precise volumes for microdroplets, illustrative ranges for channels may be between 0.5 and 50/$\mu$m in depth (preferably between 5 and 20 $\mu$m) and between 20 and 1000/$\mu$m in width (preferably 500/$\mu$m), and the volume of the microdroplets may range (calculated from their lengths) between approximately 0.01 and 100 nanoliters (more typically between ten and fifty).

The first microdroplet transport channel may be operably or functionally connected to, or in liquid communication with, at least a second microdroplet transport channel. First and second channels may operatively interact prior to connection with at least a first isothermally regulated reaction chamber. This would be the first meaning of "connective channels". However, other operative connections are envisioned, and separate transport channels that function to deliver fluids to a common reaction chamber are still "interactive transport channels" in the context of the present invention in that they convey their contents to a common destination.

The present invention is not limited to the number of transport channels or other fluid-conveying means that may be provided in the substrate. The number and configuration of such channels will generally be dictated by the number of reaction chambers and other components provided on the substrate and/or the interaction of various individual chip elements to form a coordinated system.

At least one isothermally regulated reaction chamber is an important element of the present invention. As used herein, an "isothermally regulated reaction chamber" is a chamber, preferably one defining a microvolume receptacle, the temperature of which chamber may be regulated in order to keep it substantially constant. The "substantially constant" temperature may be controlled within a few degrees, or within a single degree, or in certain embodiments, within a few tenths of a degree.

The means for isothermally regulating the reaction chamber may include, but are not limited to, resistors in contact with or in proximity to the reaction chamber, temperature detectors, resistive temperature detectors, dielectric sensors, or diodes and/or circuitry for temperature control. As discussed, the isothermal regulation means will preferably be a programmable means. The actual means of conveying the heat will preferably be a sheet resistively heated (rather than a wire), although polysilicon and doped polysilicon and diaphragm-type heaters may also be used in the reaction chamber.

In certain embodiments of the present invention, the microfabricated substrate further defines at least a first entry port operably or functionally connected to, or in liquid communication with, at least a first microdroplet transport channel. Any one of a variety of entry valves or ports may be used to control application of the sample or samples.

In embodiments where the microfabricated substrate further defines at least a second microdroplet transport channel, at least a second entry port may be provided in operable or functional connection, or in liquid communication with the second microdroplet transport channel. The invention is not limited to the number of transport channels, nor to the number of entry ports, either in terms of ports per channel or the total number of entry ports.

"Exit ports" or "sample collection points" are also envisioned, which are generally positioned at a downstream flow site from the reaction chamber.

In certain aspects of the invention, the microfabricated substrate will further comprise a flow-directing means system in order to facilitate that directed manipulation of fluids around the substrate. The term "flow-directing means system" is intended to refer to one or more modifications of the substrate or other components used in functional association with the substrate that act to control, or further control, the transport, merging and/or mixing of fluids or microdroplets between the components etched onto the underlying substrate.

Certain preferred flow-directing means systems are those that employ a surface-tension-gradient mechanism in which discrete droplets are differentially heated and propelled through etched channels. A series of heating elements may thus be arrayed along the one or more microdroplet transport channels. Such resistive heaters may be located slightly beneath the channels. In certain aspects of the invention, the heating elements are comprised of aluminum, although one or more or a combination of other suitable resistive metals or materials may be employed, such as platinum, gold, etc.

In certain aspects of the invention, "heating element" may refer to an element that is capable of at least partially liquefying a meltable material. A meltable material is "associated with" a heating element when it is in proximity to the heating element such that the heating element can at least partially melt the meltable material. The proximity necessary will depend on the melting characteristics of the meltable material as well as the heating capacity of the heating element. The heating element may or may not be encompassed within the same substrate as the meltable material.

Other fluid-directing means systems for use in the invention are those that comprise a gas source in fluid communication with the one or more transport channels and other components, such that application of differential gas pressure gradients result in the controlled flow of gases or liquids through the micromachined device.

Differences in hydrophobic and hydrophilic surface structures may also be employed to control the flow or transport of fluids through the defined channels and etched components. In such embodiments, the transport channels and/or components may comprise or may be manipulated to comprise one or more hydrophobic regions. The channels and components may also be treated with a hydrophilicity-enhancing compound or compounds prior to addition of one or more of the biological samples or amplification reaction reagents.

"Hydrophilicity-enhancing compounds" are generally those compounds or preparations that enhance the hydrophilicity (water affinity) of a component, such as a transport channel. "Hydrophilicity-enhancing compound" is thus a functional term, rather than a structural definition. For example, Rain-X™ anti-fog is a commercially available reagent containing glycols and siloxanes in ethyl alcohol. The fact that Rain-X™ anti-fog renders a glass or silicon surface more hydrophilic is more important than the reagent's particular formula.

In certain aspects of the invention "hydrophobic reagents" are used to make "hydrophobic coatings" and create "hydrophobic regions" (more water repellent) in channels. It will be understood that the present invention is not limited to particular hydrophobic reagents. In one embodiment, the present invention contemplates hydrophobic polymer molecules that may be grafted chemically to the silicon oxide surface. Such polymer molecules include, but are not limited to, polydimethylsiloxane. In another embodiment, the present invention contemplates the use of silanes to make hydrophobic coatings, including but not limited to halogenated silanes and alkylsilanes. The invention is not limited to particular silanes; the selection of the silane is only limited in a functional sense, i.e., that it render the surface hydrophobic.

In one embodiment, n-octadecyltrichlorosilane (OTS) is used as a hydrophobic reagent. In another embodiment, octadecyldimethylchlorosilane is employed. In yet another embodiment, the invention contemplates 1H, 1H, 2H, 2H-perfluorodecyltricholorosilane (FDTS, $C_{10}H_4F_{17}SiCl_3$) as a hydrophobic reagent. In still other embodiments, fluoroalkyl-, aminoalkyl-, phenyl-, vinyl-, bis silyl ethane- and 3-methacryloxypropyltrimethoxysilane (MAOP) are contemplated as hydrophobic reagents. Such reagents (or mixtures thereof) are useful for making hydrophobic coatings, and more preferably, useful for making regions of a channel hydrophobic (as distinct from coating the entire channel).

This invention is not limited to particular dimensions for the hydrophobic regions of the channels or components. However, while a variety of dimensions are possible, it is generally preferred that the regions have a width of between approximately 10 and 1000 μm (or greater if desired), and more preferably between approximately 100 and 500 μm.

A surface (such as a channel surface) is "hydrophobic" when it displays advancing contact angles for water greater than approximately 70°. In one embodiment, the treated channel surfaces of the present invention display advancing contact angles for water between approximately 90° and approximately 130°. In another embodiment, the treated microchannels have regions displaying advancing contact angles for water greater than approximately 130°.

In certain aspects of the invention, a "liquid-abutting hydrophobic region" may refer to a hydrophobic region within a channel which has caused liquid (e.g., aqueous liquid) to stop or be blocked from further movement down the channel, said stopping or blocking being due to the hydrophobicity of the region, said stopped or blocked liquid positioned immediately adjacent to said hydrophobic region.

Other flow-controlling or flow-directing means systems contemplated for use in the present invention are those that rely on the phenomenon of electrowetting, and/or differences in the dielectric constant between the reagent fluids and air. Electrowetting may be described as the initial intake of fluid from a reservoir into a channel, electrowetting (or heating) may also be used to break the channel droplet from contact with the reservoir. Valve sealed by a movable diaphragm and/or meltable solder can also be used to control fluid flow.

Any one of a variety of pumps, both external and internal pumps, may be used in order to control the flow of fluids in the context of this invention. In certain aspects of the invention a "bubble pump" may be used as a flow-directing means. A bubble pump operates as follows: fluid is introduced into a channel that comprises one or more electrodes positioned such that they will be in contact with a liquid sample placed in the channel. Two electrodes may be employed and a potential may be applied between the two electrodes. At both ends of the electrodes, hydrolysis takes place and a bubble is generated. The gas bubble continues to grow as the electrodes continue pumping electrical charges to the fluid. The expanded bubble creates a pressure differential between the two sides of the liquid drop which eventually is large enough to push the liquid forward and move it through the polymer channel.

When coupled with a capillary valve, a bubble pump can actuate an effective quantity of fluidic samples along the channel. The capillary valve is a narrow section of a channel. In operation, the fluidic sample is first injected into an inlet reservoir. As soon as the fluid is loaded, it moves in the channel by capillary force. The fluid then passes the narrow section of the channel but stops at the edge where the channel widens again. After the fluidic sample is loaded, a potential is applied between two electrodes. At both ends of the electrodes, hydrolysis occurs and bubble is generated. The bubble keeps growing as the electrodes continue pumping electrical charges to the fluid. The expanding bubble then creates a pressure differential between the two sides of the liquid drop, which eventually large enough to push the liquid forward.

The combination of bubble pump and capillary valve does not require any moving parts and is easy to fabricate. In addition, the device produces a well-controlled fluid motion, which depends on the bubble pressure. The bubble pressure is controlled by the amount of charges pumped by the electrodes. The power consumption of the device is also minimized by this method.

In certain aspects of the invention, the flow-directing means is separated from at least the first microdroplet transport channel by a liquid barrier. "Liquid barrier" or "moisture barrier" refers to any structure or treatment process on existing structures that prevents short circuits and/or damage to electronic elements (e.g., prevents the destruction of the aluminum heating elements). In one embodiment, the liquid barrier may comprise a first silicon oxide layer, a silicon nitride layer and a second silicon oxide layer.

Further preferred aspects of the invention are those wherein the microfabricated substrate further defines, or is operably associated with, a nucleic acid analysis component operably connected to or in liquid communication with the isothermally regulated reaction chamber. The operative connection between the nucleic acid analysis component and the reaction chamber is such that the amplified nucleic acid products generated by the isothermal amplification reaction can be analyzed by the nucleic acid analysis component. The overall analytical method thus requires that the amplified products are conveyed or otherwise transported from the isothermally regulated reaction chamber to the nucleic acid analysis component in a manner effective to allow their subsequent analysis, separation, detection, or such like.

Any one of a variety of nucleic acid separation and analytical components may be used as part of the devices or systems of the present invention. Amplification product separation means include those for use in separation methods based upon chromatographic separation, including adsorption, partition, ion-exchange and molecular sieve, and techniques using column, paper, thin-layer and gas chromatography. Gel electrophoresis, liquid capillary electrophoresis, e.g., in glass, fused silica, coated and rectangular column format, polyacrylamide gel-filled capillary columns are particularly contemplated. Gel electrophoresis channels and/or capillary gel electrophoresis channels may thus be etched into the substrate.

The use of a miniature electrophoresis stage for macromolecule DNA separation is also contemplated. Using such a system can accomplish large savings of time and fluids by a reduction in sample size, an increase in processing system speed of the system, a increase in the number of samples handled through massive parallelism and batch fabrication techniques.

In certain embodiments, the present invention will comprises a nucleic acid detection means operably connected to, or in electrical communication with, the nucleic acid analysis component. Visualization means particularly envisioned include those using ethidium bromide/UV and radio or fluorometrically-labeled nucleotides, including antibody and biotin bound probes. The nucleic acid detection means may thus include, but is not limited to, a diode detection device with suitable filters for detection of radioactive decay, fluorescence, visible and nonvisible light wavelengths, and/ or electromagnetic field changes.

The nucleic acid detection means may be a DNA sensor means, e.g., one that detects a radiolabel or a fluorescent label. Such DNA sensor means may be p-n-type diffusion diodes or p-n-type diffusion diodes combined with a wavelength filter and an excitation source. Silicon radiation/ fluorescence detectors, photodiodes, silicon diffused diode detectors, and other silicon fabricated radiation detectors are also contemplated.

The control circuitry for preferable use in the device may be "on wafer control circuitry" or "off wafer control circuitry", the latter preferably for use in non-glass devices. In addition to the isothermal temperature controls, the control circuitry employed may include sample size and flow control circuits; timing circuits; electrophoretic separation bias, data detection and transmission control circuits; and one or more sequencer/timers to control the overall operation.

Thus the instant devices are contemplated for use in conducting a diagnostic test on a nucleic acid sample. Additionally, the present devices are contemplated for use in conducting a diagnostic or prognostic test on a biological sample suspected of containing a selected nucleic acid. Therefore, the present invention provides for the use of the instant devices in the manufacture of a kit or system for the amplification of nucleic acids. In certain aspects, the invention provides for the use of the present devices in the manufacture of a kit or system for the diagnosis or prognosis of a disease.

Any one or more of the isothermal amplification devices or chips of the present invention may be formulated or packaged with biological reagents effective to permit an isothermal nucleic acid amplification reaction. In such aspects, the combined reagents and devices may be considered as "isothermal nucleic acid amplification kits". "Biological reagents effective to permit an isothermal nucleic acid amplification reaction" are exemplified by polymerases, nucleotides, buffers, solvents, nucleases, endonucleases, primers, target nucleic acids including DNA and/or RNA, salts, and other suitable chemical or biological components.

The kits may thus be defined as comprising, in suitable container means at least a first microfabricated substrate defining at least a first channel, the at least a first channel connected to an isothermally regulated reaction chamber, and reagents effective to permit an isothermal amplification reaction.

In such kits, the first microfabricated substrate may further define a nucleic acid analysis component operably connected to said isothermally regulated reaction chamber and, optionally, a nucleic acid detection means operably connected to the nucleic acid analysis component.

The biological reagents effective for use in the amplification reactions may be provided or packaged in any suitable form, preferably aliquoted into suitable quantities. In certain preferred aspects, such reagents will be provided in a dry or lyophilized formulation. The provision of reagents, preferably in a lyophilized form, applies to both kits, in which the reagents are generally separately packaged, and integral devices, in which the lyophilized reagents may be pre-fabricated into one or more etched components on the substrate.

In certain other embodiments, an effective amount of the amplifying reagents may be provided in a separate cartridge that is interchangeably connected to the device, chip or system. Such replaceable cartridges or reservoirs may be provided in the same overall container means as the device, chip or system or may be purchased separately as distinct items. Different replaceable cartridges may be provided for conducting the various different isothermal amplification reactions that are known in the art. A number of reagent formulations may be packaged together for alternative use according to the needs of the end user.

Diagnostic systems are also provided by the present invention, comprising at least a first microfabricated substrate defining at least a first channel that is connected to at least a first isothermally regulated reaction chamber; wherein the diagnostic system further comprises a nucleic acid analysis component and a nucleic acid detection means in operable association with the reaction chamber of the microfabricated substrate.

The diagnostic systems may also comprise, in operable association, at least a second microfabricated substrate defining at least a second channel that is connected to at least a second isothermally regulated reaction chamber. Third, fourth, fifth, tenth, 20th, 50th, 100th, 500th and 1000th microfabricated substrates may also be provided, as is the meaning of "a plurality of microfabricated substrates".

The diagnostic systems may variously have at least a first and at least a second microfabricated substrate, or a plurality thereof, that are operably connected in series to a single nucleic acid analysis component and nucleic acid detection means. The diagnostic systems may alternatively comprise at least a first and at least a second microfabricated substrate, or a plurality thereof, that are operably connected in parallel to at least two distinct nucleic acid analysis components and nucleic acid detection means, or a plurality of such components.

In such kit and system embodiments, liquid handling, electrophoresis, and detector components may be coupled into an integrated format. DNA samples may move directly between sample processing, size-separation, and product detection. The components are controlled by electronic circuitry, fabricated on the same silicon wafer.

Accordingly, an integrated DNA sample processing design may be arrayed as multiple parallel units on a single silicon wafer. The number of parallel DNA processing units per wafer may be maximized, and circuitry used for overall control. A large number of simultaneous isothermal amplification reactions (up to 1000 per wafer) may be performed on such systems.

Methods of making devices for use in isothermal nucleic acid amplification are provided by the invention, which generally comprise preparing at least a first microfabricated device, chip or wafer defining at least a first channel that is operably connected to an isothermally regulated reaction chamber, preferably isothermally regulated by a programmable means.

A method of making a nucleic acid diagnostic kit is also provided, which generally comprises preparing at least a first microfabricated device, chip or wafer defining at least a first channel that is operably connected to an isothermally regulated reaction chamber, and combining the microfabricated device with biological reagents effective for use in an isothermal amplification reaction. The combination may be with lyophilized reagents, which may further be disposed in the device as an integral component.

Methods of making a nucleic acid diagnostic system are further provided, comprising preparing at least a first microfabricated substrate defining, in a series of operable associations, at least a first channel, an isothermally regulated reaction chamber, a nucleic acid analysis component and a nucleic acid analysis detection means.

Multi-component nucleic acid diagnostic systems may also be manufactured by the methods of the present invention. To make a multi-component nucleic acid diagnostic system, a plurality of microfabricated substrates, nucleic acid analysis and detection means are operably combined, preferably in an interactive array or arrays. Controlling electronic circuitry and programmable regulating means are preferably provided. Multiple parallel unit arrays on single silicon wafers are particularly preferred.

Important aspects of the present invention are methods for the isothermal amplification of selected nucleic acids or portions thereof, which methods generally comprise providing or introducing a microdroplet sample comprising or suspected of comprising the selected nucleic acid, and reagents effective to permit an isothermal amplification reaction, to at least a first microfabricated substrate with an isothermally regulated reaction chamber, as generally defined hereinabove, and conducting an isothermally regulated amplification reaction to amplify the selected nucleic acid or a portion thereof.

As used herein, the terms "providing" or "introducing" mean that the sample or samples are provided or introduced into the one or more microfabricated substrates in a manner effective to begin their conveyance, transportation or general movement to the isothermally regulated reaction chamber. As described hereinabove, a number of particular flow-directing means systems may be employed in order to convey the sample or samples to the reaction chamber. Where differential heating is employed as the sole transport means, or as part of the overall transport means, an important aspect of the invention is that any samples that comprise enzymes for use in the isothermally regulated nucleic acid amplification reaction are "thermotransported" at a temperature below the critical temperature of the polymerase enzyme. Preferably, all samples will be transported at temperatures that are below the critical ranges for substantial inactivation of the enzymes for use in the isothermal amplification reaction. It is a surprising feature of the invention that heat-conveying temperatures effective to transport samples into the reaction chamber can be employed that are far enough below the denaturation and/or inactivation temperatures of the enzymes necessary to catalyze the isothermal nucleic acid amplifications. The invention may thus be characterized as including a method step of conveying said sample and/or said reagents from an initial contact point on the microfabricated substrate to the isothermally regulated reaction chamber at a "transportingly effective temperature" that does not significantly denature the selected amplification enzyme or otherwise significantly impair or reduce its catalytic amplification activity.

The isothermal amplification reactions of the invention are also conducted at temperatures effective and by means effective to result in productive mixing of the one or more samples and amplification reagents. "Effective mixing" is a functional term, most readily characterized by the operative execution of the amplification reaction such that amplified products may be detected. If desired, one or more samples containing nucleic acids and/or amplification reagents may first be "merged" prior to mixing.

In certain definitional terms, "merging" is distinct from "mixing." When a first and second microdroplet is merged to create a merged microdroplet, the liquid may or may not be mixed.

In any event, irrespective of the degree of prior sample association, the isothermal amplification reaction as a whole must be conducted under conditions effective to adequately mix the substrates and other components of the reaction. Prior to the present invention, it was generally believed in the art that effective mixing could not be achieved at the temperatures preferred for use in the present isothermal amplification reactions. Only the endeavors of the present inventors, conducted despite the prejudices in the prior art, resulted in the discovery that effective mixing could be achieved. Effective mixing is achievable despite the viscosity of the samples and/or reagent formulations used, and the particular biological components employed in connection with the isothermal amplification enzyme solutions and/or suspensions.

Those of ordinary skill in the art will be able to vary the application of the samples and reagents and the manner of transporting such components to the reaction chamber, in addition to varying the particular details of the amplification reaction, in order to ensure that a degree of mixing sufficient to result in amplified products is achieved. Moreover, the degree of mixing in a merged microdroplet may be enhanced by a variety of techniques provided by the present invention, including but not limited to, reversing the flow direction of the merged microdroplet (as discussed herein below).

Although not in any way being limited by the following guidance, the temperature differential believed to be effective in conveying microdroplet samples along a microfabricated device in accordance with the present invention should generally be a temperature differential of at least about 10° C. Preferably, temperature differentials of at least about 11° C., 12° C., 13° C., 14° C., 15° C., 16° C., 17° C., 18° C., 19° C., 20° C., about 25° C., about 30° C., about 35° C. or even up to about 40° C. or above may be advantageously used in conveying microdroplet samples along a micromachined device or substrate. It will be understood that each of the foregoing effective conveying temperature differentials must be analyzed in connection with the preferred operating temperatures for any one or more particular amplifying enzyme, and that the temperatures chosen must be below the temperature at which the enzyme denatures or otherwise becomes significantly impaired in its catalytic activity. In general, it is believed that temperature differences of greater than about 30° C. will be preferred for creating microdroplet motion or movement. In certain other embodiments, temperature differentials of about 40° C. will be effective, and these temperature gradients can be readily generated by a number of means, particularly by the use of a series of temperature sensors arrayed along the entire length of the one or more conveying channels etched into the substrate.

Although an understanding of the mechanisms of action underlying the surprising operability of the present invention is not necessary in order to carry out the claimed amplification methods, the inventors further point out that circulation patterns generated in the drop during motion aid in mixing the liquid sample. Studies using metal elements as both heaters and temperature sensors demonstrate that a temperature differential of 20–40° C. across the drop is sufficient to provide forward motion in transport channels.

Thus for only small temperature differences across the drop (on the order of 10° C.) velocities on the order of 1 cm/s may be obtained. This velocity is more than sufficient for transporting liquid drops in MIDAT and other chip based systems.

Those of ordinary skill in the art will further understand that other physical components of the chip fabrication will impact the temperatures effective to transport microdroplets. By way of example only, in studies using glass capillaries, it has been found that there is a minimum temperature difference required to move the droplet. For instance, if the advancing angle is 36° and the receding angle is 29° (with the front of the droplet being 25° C.), then the back of the droplet would need to be heated to ~60° C. for a 1 mm long droplet in a 20 mm high channel. This is just one example situation.

The use of channel geometry and defined chip fabrications that necessitate higher transport temperatures will naturally be combined with the use of enzymes that are functional at higher isothermal amplification temperatures. The choice of enzyme and transport temperatures will be routine to those of ordinary skill in the art, with a number of possibilities being readily available. By way of example only, methods for isothermal SDA are available in which temperatures of between about 50° C. and about 70° C. are used in conjunction with a thermophilic amplification enzyme. Accordingly, temperatures of about 30° C., about 35° C., about 40° C., about 45° C., about 50° C., about 55° C., about 60° C., about 65° C., about 70° C., also may be employed.

However, the calculations of the present inventors indicated that about a 35° C. difference between the front and back of a droplet will be sufficient to initiate droplet motion in a system with advancing angles of 36° and receding angles of 29° in a 20 mm high channel. Further studies of effective transport showed that the resulting temperature difference was −40° C. between the front and back of the droplet, thus corroborating the initial determination of the requirements.

This shows that the range of transporting temperatures and the variety of enzymes for use in the invention extends to encompass each of the enzymes known to be suitable for use in isothermal amplifications. For example, 3SR and Qbeta-replicase are known to function at 37° C., which can be used as part of the effective conveying temperature. Classical SDA reactions can also be conducted at a constant temperature between about 37° C. and 42° C., the preferred range identified in U.S. Pat. No. 5,455,166 (incorporated herein by reference).

U.S. Pat. No. 5,455,166 is also incorporated herein by reference for the purposes of exemplifying the level of skill in the art regarding the selection of each component necessary for the isothermal amplification reaction. For example, this patent explains that, in addition to the DNA polymerases, the restriction endonucleases necessary to carry out the reaction are also mesophilic enzymes that are thermolabile at temperatures generally above the 37–42° C. advised for use in the reaction. All such considerations will be readily employed by those of skill in the art as they select the reagents necessary for use in the present isothermal amplification reactions.

In terms of the isothermal amplification reaction itself, rather than the transporting, merging and/or mixing steps, those of ordinary skill in the art will instantly appreciate appropriate temperatures for use in connection with the selected polymerase, replicase or other amplification system. By way of example only, isothermal amplification reactions involving 3SR and Qbeta-replicase may be conducted at or about 37° C. Standard SDA isothermal amplification reactions may be conducted at a constant temperature between about 37° C. and 42° C. (including 38° C., 39° C., 40° C. and 41° C.), whereas isothermal SDA using a the enzyme may be performed at a higher temperature range than conventional SDA, anywhere between about 50° C. and about 70° C.

Any effective temperature that will support the desired enzymatic activity, even if sub-optimal, may be employed in the isothermal amplification reactions of this invention. Accordingly, the isothermal amplifications may be conducted at any substantially constant and effective temperature, including at about 20° C., 21° C., 22° C., 23° C., 24° C., 25° C., 26° C., 27° C., 28° C., 29° C., 30° C., 31° C., 32° C., 33° C., 34° C., 35° C., 36° C., 37° C., 38° C., 39° C., 40° C., 41° C., 42° C.,43° C., 44° C., 45° C., 46° C., 47° C., 48° C., 49° C., 50° C., 51° C., 52° C., 53° C., 54° C., 55° C., 56° C., 57° C., 58° C., 59° C., 60° C., 61° C., 62° C., 63° C., 64° C., 65° C., 66° C., 67° C., 68° C., 69° C., 69° C., 70° C., 71° C., 72° C., 73° C., 74° C., 75° C., and the like.

It will be understood that the overall isothermal amplification reaction is carried out in a manner effective to result in at least detectable amounts of amplified products. "At least detectable amounts of amplified products" refers to a yield of amplified nucleic acid products that can be detected by currently available nucleic acid detection means. Optical methods using efficient fluorophores can detect atto-molar concentrations (corresponding to ~$10^5$ DNA molecules) migrating in capillary channels of 8×50 mm internal cross section (Woolley and Mathies, 1994; incorporated herein by reference). Reactions for synthesizing such DNA quantities can reasonably occur in 10 µl. An integrated system designed for picoliter volumes may require channel dimensions on the order of 10 µm$^2$×100 µm (cross section×length).

In contrast to the negative beliefs in the prior art, the present invention has provided methods for target amplification efficiency surprisingly equivalent to conventional SDA reactions, but conducted on a DNA chip. Amplifications of almost a million-fold have already been achieved. This demonstrated that the physical changes in the environment on the DNA chip, including silicon contact, temperature gradients, surface interactions and other potential inhibitors, did not adversely affect the amplification reaction.

In certain preferred embodiments, it is believed that the isothermal amplification reactions of the present invention will be conducted such that the sample nucleic acids are amplified at least about 100-fold, 200-fold, 300-fold, 400-fold, 500-fold, 1000-fold, 2000-fold, 5000-fold, 10,000-fold, 50,000-fold, 100,000-fold, 200,000-fold, 300,000-fold, 400,000-fold, 500,000-fold, 600,000-fold, 700,000-fold, 800,000-fold, 900,000-fold, or so, up to and including at least about 1,000,000-fold, 2,000,000-fold or so.

The simplicity of sample provision to microfabricated devices is another surprising feature of the present isothermal amplification methods. The samples may be provided in any "silicon-compatible formulation". Prior to the present invention, it was not known whether the various isothermal polymerases and replicases would be operative in contact with the fabricating structures of a microdevice, particularly the preferred silicon formulations. The diligent studies of the present inventors have shown that the present isothermal amplification methods function in a "silicon-compatible manner", and the methods of the invention are intended to be carried out in such effective manners.

The provision of the sample to the microfabricated or micromachined devices or systems is not believed to be critical, so long as the samples are later capable of being conveyed along the appropriate channels. Sample sources include, but are not limited to, continuous streams of liquid as well as static sources (such as liquid in a reservoir). In a preferred embodiment, the source of liquid microdroplets comprises liquid in a microchannel from which microdroplets of a discrete size are split off. As described above, in certain preferred embodiments, the reagents for use in the isothermal reaction will already be comprised within a pre-fabricated microdevice. In such embodiments, lyophilized reagents may be rendered active by contact with the nucleic acid-containing sample, or alternatively, they may be separately contacted with another fluid sample, such as a buffer.

The samples comprising the nucleic acids for application in the present isothermal amplification methods may be "laboratory samples" for use in any one of a variety of molecular biological embodiments. Such samples may also be "biological or clinical samples", in which case the samples will generally be obtained from or otherwise derived from an animal or human subject.

In any event, where the samples used are "microdroplet samples", this term generally refers to the microdroplet themselves and samples from which microdroplets may be made.

Whether the sample is a laboratory, biological or clinical sample, the purity of the nucleic acids within the sample may vary widely. The purity of the sample is controlled only by the need to have a minimum purity necessary for successful execution of the isothermal amplification reaction. In certain embodiments, the sample will have been subjected to a substantial degree of extraction or purification prior to use in the present invention, although this is not necessary in all embodiments.

In terms of the biological samples, these may be obtained from a variety of biological fluids, including blood, plasma, urine, sputum, semen, and fluids obtained from homogenized tissues. It is not believed to be necessary to limit the presence of other biological components, such as proteins and lipids, from the samples for use in the invention, although this may be desired in certain embodiments and is within the level of skill of the ordinary artisan.

In common with the sample preparation, the purity of the reactants provided to the device and the makeup of the device itself require some degree of biocompatability in order to achieve the desired reaction. That is to say, that the isothermal amplification reaction should not be substantially inhibited or prevented by any components present within the biological sample, contaminants within the reactants or by the characteristics or nature of the device components, including the silicon fabricants.

It will be understood that the particular components, amounts of components and/or reactants and the particular conditions of the reaction may be modified in order to optimize the isothermal amplification reaction itself. All such variations and modifications are routinely investigated in this field of study. By way of example only, one may vary the concentration of any of the components or the samples, the temperature, pH or ionic makeup of the buffers, and generally vary any other parameter of the amplification reaction.

It will be understood that the execution of the amplification reaction, including the application of the samples and the movement, mixing and distribution of the samples prior to the actual isothermal amplification step, may also require certain optimizations. All such variations and optimizations will be routine to those skilled in this field of study.

All liquid distributions and manipulations may be performed entirely within a handling system formed as channels in micromachined silicon. Sensors may monitor the temperature and location of liquid in the channels. The manipulation of reagents includes the movement, merging, mixture, and temperature control of the reagents to allow nucleic acid amplification under isothermal reaction conditions.

In certain aspects of the present invention, the isothermal amplification methods and the reagents provided for use in the methods will be based upon the strand displacement amplification reaction. Self-sustained sequence replication amplification reactions and/or Qβ replicase amplification reactions may also be used.

A preferred technique is the Strand Displacement Amplification (SDA). The SDA reaction may be conducted at a substantially constant temperature between about 37° C. and about 42° C., or at any other effective temperature, as exemplified herein by 52° C. It was previously believed that the low temperature requirement for SDA would prevent its use in connection with amplification on microchip devices. However, the inventors discovered that the potential problems of stagnant temperature gradients and reduced diffusion and sample mixing do not actually impact the efficiency of the SDA reaction in such microvolume embodiments.

Thermophilic SDA may also be employed, as described in published European Patent Application No. 0 684 315 (incorporated herein by reference). This technique employs thermophilic restriction endonucleases which nick the hemimodified restriction endonuclease recognition/cleavage site at high temperature and thermophilic polymerases which extend from the nick and displacing the downstream strand in the same temperature range. At increased temperature, the amplification reaction has improved specificity and efficiency, reduced nonspecific background amplification, and potentially improved yields of amplification products.

In terms of amplified product analysis, DNA samples may be size-fractionated on an electrophoresis system built within or attached or connected to the silicon substrate. Electrophoresed DNA products may be visualized by radioactivity or fluorescence detectors fabricated directly in the silicon wafer.

In certain aspects of the invention, the amplified nucleic acid is detected by means of a detectable label incorporated into the amplified selected nucleic acid by the isothermal amplification reaction. In other aspects, it is detected by means of a labeled probe. The label may variously be a radioisotopic, enzymatic or fluorescent label.

The present invention further provides methods for detecting the presence of a selected nucleic acid, comprising introducing a sample suspected of containing the selected nucleic acid, and reagents effective to permit an isothermal amplification reaction, into a microfabricated substrate defining at least a first channel, the at least a first channel connected to an isothermally regulated reaction chamber, conducting an isothermally regulated amplification reaction to amplify the selected nucleic acid, and detecting the presence of the amplified selected nucleic acid, wherein the presence of the amplified selected nucleic acid confirms the presence of the selected nucleic acid in the sample.

The sample may be obtained or derived from an animal or patient having or suspected of having a disease. It will be understood that in certain aspects of the present diagnostic and/or prognostic methods, the presence of the ultimate amplified selected nucleic acid will be indicative of the disease state being analyzed. In alternative embodiments, it is the absence of amplified nucleic acid products that is indicative of a disease state. In either embodiment, the present invention is ideally suited for the amplification of nucleic acids of defined sequence, having a defined sequence element, or including a potential point mutation, as each of the foregoing variants may be distinguished by analyzing the amplified products resulting from execution of the presently claimed methods.

BRIEF DESCRIPTION OF THE DRAWINGS

FIG. 2A shows one embodiment of a single microfluidic device. FIG. 2B shows one aspect of a silicon device comprising a plurality of microfluidic device modules.

FIG. 3A shows the liquid sample prior to splitting. FIG. 3B shows the liquid sample after splitting off a microdroplet of length L. The hatched regions represent the hydrophobic regions.

FIG. 4A shows a liquid sample prior to splitting. FIG. 4B shows the liquid sample after splitting off a microdroplet of length L. The hatched regions represent the hydrophobic regions.

DESCRIPTION OF ILLUSTRATIVE EMBODIMENTS

1. DESIGN OF MICROSCALE DEVICES FOR ISOTHERMAL AMPLIFICATION REACTIONS

Figure 1:
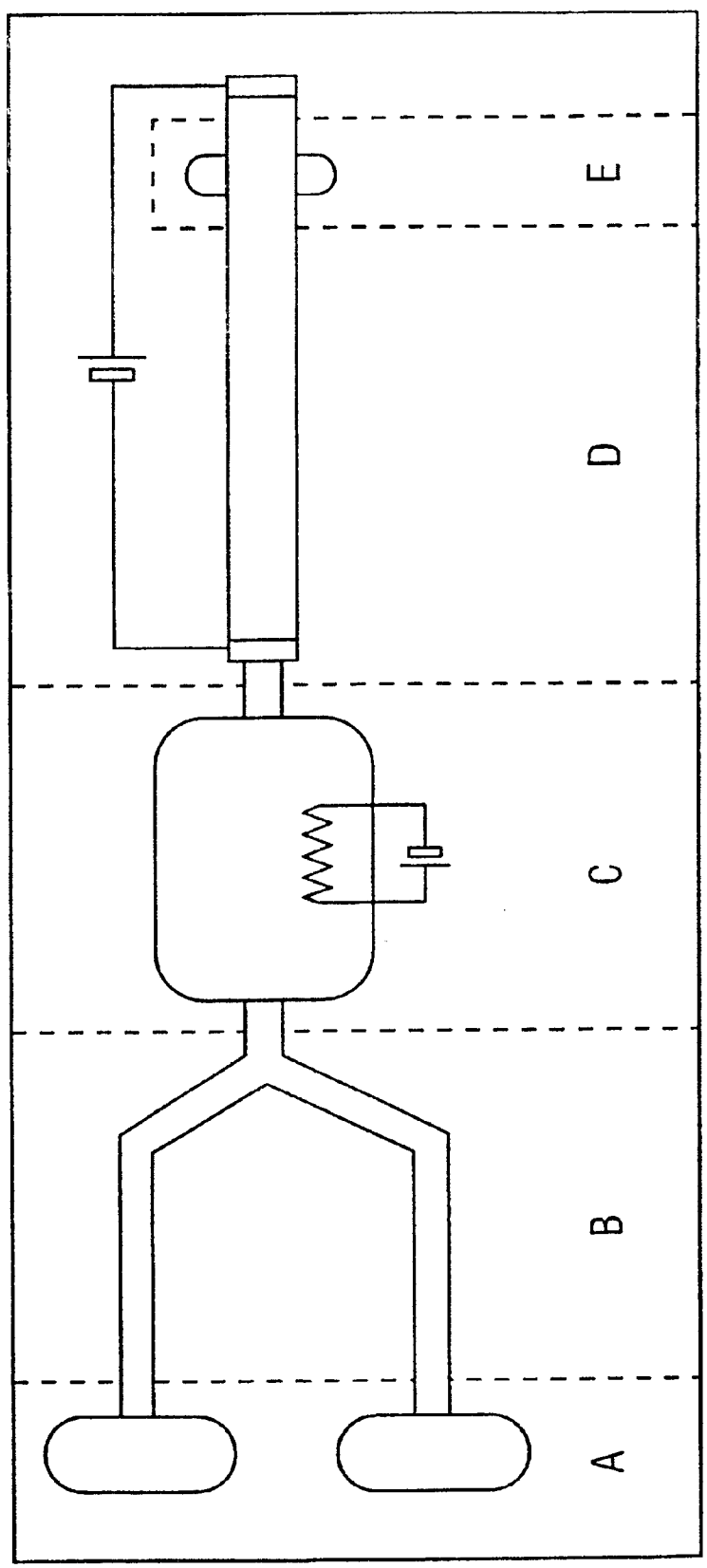
FIG. 1. Example of an integrated DNA analysis system, represented schematically. The individual components of the system are injection entry ports (A), liquid pumping channels (B), thermally (i.e., isothermally) controlled reaction chamber (C), electrophoresis channel (D), and DNA band migration detector (E). Each component would have associated sensors, control circuitry, and external connections.

The amplification of nucleic acids provides a convenient way to diagnose a variety of disease states. However, prior to the present invention, it was unknown whether the movement, mixing, and merging of viscous microvolume fluids at lower temperature to conduct isothermal amplification reactions was possible in a microfabricated environment. Isothermal amplification reactions employ reaction schemes and enzymes which are very different from PCR™, and it is unknown whether or not the enzymology of isothermal amplification reactions is compatible with chip hardware and materials.

Specifically, the only enzyme necessary for PCR™ amplification of DNA targets is a thermostable DNA polymerase. Isothermal DNA amplification reactions employ additional enzymes with different biological activities because heat is not used to denature double-stranded nucleic acids. In addition to a DNA polymerase, 3SR requires an enzyme with RNase H activity and an RNA polymerase. The SDA reaction requires several very specific enzymatic activities which are not necessary for PCR™ in order to successfully amplify a target sequence. In addition to synthesizing a new DNA strand, the DNA polymerase in SDA must lack 5'-3' exonuclease activity, either naturally or by inactivation, incorporate the modified nucleotides required by SDA (αthio-dNTPs or other modified dNTPs), and displace a downstream single strand from a double stranded molecule starting at a single stranded nick. In addition, the restriction endonuclease in SDA must nick (i.e., cleave a single strand of) its double stranded recognition/cleavage site when the recognition/cleavage site is hemimodified and dissociate from its recognition/cleavage site rapidly enough to allow the polymerase to bind and amplify the target efficiently. The restriction endonuclease must exhibit these activities under reaction conditions which are compatible with the activities required of the polymerase.

It was not previously known if the enzymatic activities required for such isothermal amplification reactions would be inhibited by interaction with the surfaces of silicon microfabricated analysis devices or by inhibitors present in the devices (e.g., residual chemicals from microfabrication).

In addition, the change in surface-to-volume ratio which accompanies taking an enzymatic reaction developed in a test tube to the microchannel of a silicon microfabricated device may have unpredictable effects, as changes in the diffusion properties of the reactants in the channel may interfere with the amplification reaction. In particular for SDA, the interaction of the derivatized dNTPs with the microdevice environment, the effect of the environment on nicking activity by the restriction endonuclease and strand-displacing activity by the polymerase were not known. It is known that liquid movement in a closed channel, which is a convenient means for bringing components of the amplification reaction into contact, is affected by the contact angle of the liquid-gas-solid interface within the channel. Changes in the composition of the liquid in the channel change the surface tension and therefore the contact angle, affecting liquid movement. The contact angle is reduced and liquid movement is facilitated by more hydrophilic liquids such as the reaction buffers conventionally used in PCR™.

Certain isothermal amplification reactions, such as SDA, employ hydrophobic components such as glycerol and BSA, which may unpredictably affect the surface tension properties of the liquid and the ability to move it within the channels of microfabricated devices, particularly when thermocapillary pumps are used. The need to increase the amount of heat to move the liquid aliquot with a thermocapillary pump could be incompatible with the temperature requirements of the enzymes and the isothermal amplification reaction.

Lowering the temperature of the amplification reaction may also have unpredictable effects. The temperature of the reaction in the microfabricated device is typically controlled from one side of the chip, setting up a temperature gradient across the channel. The temperature conditions of isothermal amplification reactions would also be expected to alter the interactions of the reactants with the silicon or glass surfaces of the channel. Because isothermal amplification is conducted at constant, lower temperatures, the temperature gradient which is produced reaches equilibrium and becomes stagnant. In contrast, the temperature gradient in higher temperature reactions with thermocycling is not stagnant. Temperature fluctuations during PCR™ amplification serve to minimize the gradient effect, improve diffusion of reactants and facilitate mixing.

Mixing of reactants in the channels and chambers of the DNA chip is of particular concern in isothermal amplification reactions, as mixing of reactants initiates the amplification reaction. This is not the case in PCR™, as all reactants required for amplification are present together in the reaction mix. PCR™ amplification of double-stranded targets does not begin until temperature cycling is started because until that time no single-stranded target is available to amplify. This is not the case in isothermal amplification reactions. Because strand separation is an enzymatic process in isothermal amplification, at least one of the enzyme reactants (usually the polymerase) is withheld until it is desired to begin the reaction. If the isothermal amplification reaction starts with a heat-denaturation step and the enzymes employed are not thermostable, all of the enzymes for amplification are typically withheld until the target-containing sample is cooled to the appropriate reaction temperature. The sample containing the enzyme or enzymes must be mixed with the remaining reagents in order for amplification to begin.

To control initiation of the isothermal amplification reaction and provide an integrated nucleic acid analysis system, it is therefore highly desirable to keep the components separate on the microfabricated device and bring them together to initiate amplification. This requires, however, that mixing of the two components in the channel be adequate at the lower temperatures of isothermal amplification, and this mixing may be negatively affected due to temperature-related decreases in diffusion and changes in surface chemistry. The components of the amplification reaction itself may also have negative effects on mixing within the channel. Many amplification reactions contain reagents such as glycerol and bovine serum albumin which increase viscosity and could reduce mixing. The viscosity-increasing effects of these reagents is increased at lower temperatures. It was therefore unknown whether or not there would be adequate mixing, diffusion and temperature regulation to produce isothermal amplification on a silicon microfabricated device.

In certain aspects, the present invention relates to movement of microdroplets through microchannels, and more particularly, compositions, devices and methods to control microdroplet size and movement. The present invention involves microfabrication of microscale devices and reactions in microscale devices, and in particular, movement of biological samples in microdroplets through microchannels to, for example, initiate biological reactions, particularly isothermal amplification of nucleic acids.

Although there are many formats, materials, and size scales for constructing integrated fluidic systems, the present invention contemplates silicon microfabricated devices as a cost-effective solution.

The present invention contemplates microscale devices, comprising microdroplet transport channels, reaction regions (e.g., chambers), electrophoresis modules, and radiation detectors. In a preferred embodiment, these elements are microfabricated from silicon and glass substrates. The various components are linked (i.e., in liquid communication) using a surface-tension-gradient mechanism in which discrete droplets are differentially heated and propelled through etched channels. Electronic components are fabricated on the same substrate material, allowing sensors and controlling circuitry to be incorporated in the same device. Since all of the components are made using conventional photolithographic techniques, multi-component devices can be readily assembled into complex, integrated systems.

Continuous flow liquid transport has been described using a microfluidic device developed with silicon (Pfahler et al., 1990). Pumps have also been described, using external forces to create flow, based on micromachining of silicon (Van Lintel et al., 1988). The present invention employs discrete droplet transport in silicon using internal forces or external forces (i.e., external forces created by pumps).

As a mechanical building material, silicon has well-known fabrication characteristics. The economic attraction of silicon devices is that their associated micromachining technologies are, essentially, photographic reproduction techniques. In these processes, transparent templates or masks containing opaque designs are used to photodefine objects on the surface of the silicon substrate. The patterns on the templates are generated with computer-aided design programs and can delineate structures with line-widths of less than one micron. Once a template is generated, it may be used almost indefinitely to produce identical replicate structures. Consequently, even extremely complex micromachines may be reproduced in mass quantities and at low incremental unit cost—provided that all of the components are compatible with the silicon micromachining process.

While other substrates, such as glass or quartz, can use photolithographic methods to construct microfabricated analysis devices, only silicon gives the added advantage of allowing a large variety of electronic components to be fabricated within the same structure.

In one embodiment, the present invention contemplates silicon micromachined components in an integrated analysis system, including the elements identified schematically in FIG. 1. In this proposed format, sample and reagent are injected into the device through entry ports (FIG. 1-A) and they are transported as discrete droplets through channels (FIG. 1-B) to a reaction chamber, such as an isothermally controlled reactor where mixing and reactions, such as isothermal nucleic acid amplification reactions (SDA, Qβ-replicase, etc), restriction enzyme digestion, ligation, phosphorylation, dephosphorylation, sequencing or other enzymatic or chemical reaction known to those of skill in the art occur (FIG. 1-C). The biochemical products are then moved by the same method to an electrophoresis module (FIG. 1-D) where migration data is collected by a detector (FIG. 1-E) and transmitted to a recording instrument. Importantly, the fluidic and electronic components are designed to be fully compatible in function and construction with the biological reactions and reagents.

A. Two-Part Approach to Construction

Most of the devices of the invention are hybrid micromechanical devices (two substrates bonded together). The purpose of using this method is to allow the fabrication of micromechanical devices out of a variety of materials (silicon, glass, fused silica, quartz, etc.). The devices have chamber volumes that are easily handled (sample loading, component analysis, etc.) and chamber walls that are transparent (sample loading, fluorescent detection, etc.). The hybrid system also gives flexibility in choosing materials in one section of the unit without affecting other pans of that same unit.

The invention may comprise two separate wafers of either the same or different materials, including but, not limited to, silicon, glass, or quartz are micromachined independently. The pieces are then bonded together using a variety-of techniques (polyimide, UV-curing cements, anodic bonding, etc.). For transparency, a glass or quartz wafer is usually used on one side of the hybrid. In general, the sensors, heaters, and other electronic components may be patterned onto one wafer and etch channels into the other. The electronic components may use 5 μm wire width over channel regions so that, if the glass wafer has the electronic components patterned on it, the contents of the channels may be seen.

Figure 2B:
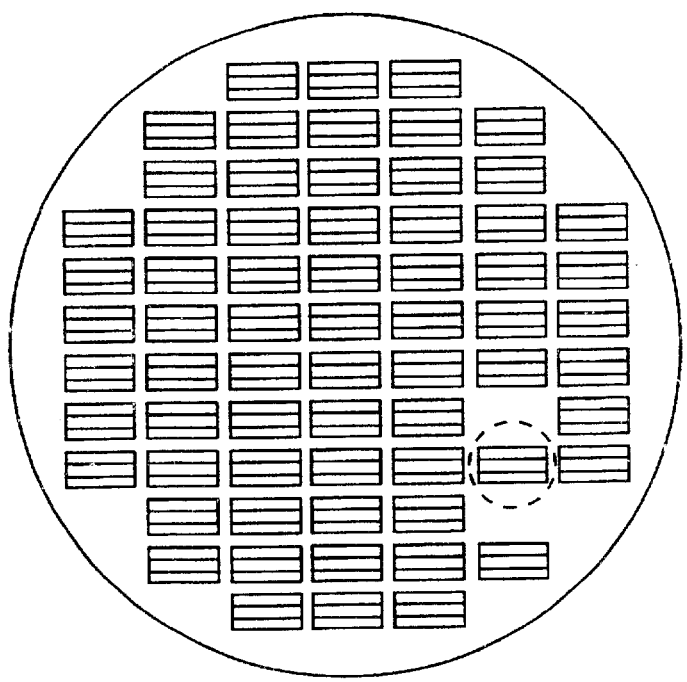
FIG. 2A and FIG. 2B. A two-part approach to construction of a silicon device of the present invention, and a silicon substrate comprising a plurality of devices.
Figure 2A:
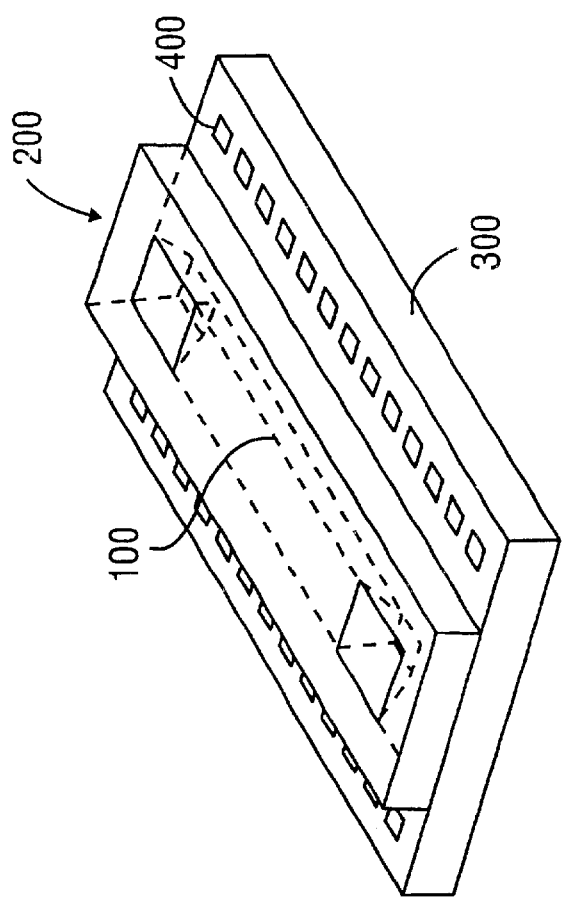

FIG. 2A shows a two-part approach to construction. Microchannels (100) are made in the silicon substrate (200) and the structure is bonded to a glass substrate (300). The two-part channel construction technique requires alignment and bonding processes but is amenable to a variety of substrates and channel profiles. In other words, for manufacturing purposes, the two-part approach allows for customizing one piece (i.e., the silicon with channels and reaction formats) and bonding with a standardized (non-customized) second piece, e.g., containing standard electrical pads (400).

Hundreds or thousands of copies of a particular component can be made simultaneously across the entire silicon wafer surface (FIG. 2B; for example, but not limited to, a wafer that is 0.5 mm thick and 100 mm in diameter). The components are made by sequential deposition, ion implantation, or etching of thin layer materials in defined patterns. Materials that are commonly used include silicon oxide, silicon nitride, and various metals and alloys.

The technology of silicon fabrication is essentially a photolithographic method for making machines. Once a "template" or "stencil" pattern has been prepared, additional copies of the machines are replicated at minimal cost and effort. The density of components is limited by line-width considerations and the designing abilities of the engineers. Complete devices are made in batches and can often exceed thousands of replicates per fabrication run. Additionally, silicon fabrication has benefited from massive industrial commitment over the past 20 years. The characteristics of the fabrication steps are known and have been incorporated into intelligent design software or computer-aided design and manufacturing packages (CAD/CAM).

B. Channel Design and Construction

In silicon micromachining, a technique to form closed channels involves etching an open trough on the surface of a substrate and then bonding a second, unetched substrate over the open channel. There are a wide variety of isotropic and anisotropic etch reagents, either liquid or gaseous, that can produce channels with well-defined side walls and uniform etch depths. Since the paths of the channels are defined by the photo-process mask, the complexity of channel patterns on the device is virtually unlimited. Controlled etching can also produce sample entry holes that pass completely through the substrate, resulting in entry ports on the outside surface of the device connected to channel structures.

The present invention contemplates a variety of silicon-based, microdroplet transport channel-containing devices. In one embodiment, the device comprises: a housing comprised of silicon, a microdroplet transport channel etched in the silicon, a microdroplet receiving means in liquid communication with a reaction region via said transport channels, and a liquid barrier disposed between the transport channels and a microdroplet flow-directing means. In one embodiment, the device is assembled in two parts. First, the channels are etched in any number of configurations. Second, this piece is bonded with a silicon-based chip containing the electronics. This allows for both customization (in the first piece) and standardization (in the second piece).

In certain aspects of the invention "conveying" may refer to causing to be moved through, as in the case where a microdroplet is conveyed through a transport channel to a particular point, such as a reaction region. Conveying may be accomplished via a flow-directing means.

The present invention also contemplates devices and methods for the sealing of channels with meltable material. In one embodiment, the device comprises a meltable material disposed within a substrate and associated with a heating element.

In one embodiment, the present invention contemplates a method comprising providing a device having a meltable material disposed within a substrate and associated with a heating element, and heating the meltable material with the heating element such that the meltable material at least partially liquefies and such that the substrate is not damaged. The method may further comprise allowing the liquefied meltable material to cool. While the present invention is not limited by the size of the channel, in one embodiment the substrate further comprises a microdroplet channel disposed in the substrate, the meltable material is disposed within the microdroplet channel.

In another embodiment, the present invention contemplates a method for restricting fluid flow in a channel comprising providing a device comprising a meltable material disposed within a substrate, the meltable material associated with a heating element; and a diaphragm positioned such that, when extended, it touches the meltable material, extending the diaphragm such that it touches the meltable material, and heating the meltable material with the heating element such that the meltable material at least partially liquefies and such that the substrate is not damaged. In one embodiment the method further comprises allowing the meltable material to cool. While the present invention is not limited by the size of the channel, in one embodiment, the substrate further comprises a microdroplet channel disposed in the substrate, the meltable material disposed within the microdroplet channel.

In certain aspects of the invention "meltable material" may refer to a material that is at least semi-solid (and preferably completely solid) at ambient temperature, will liquefy when heated to temperatures above ambient temperature, and will at least partially resolidify when cooled. Preferably, meltable material at least partially liquefies at a temperature such that the substrate is undamaged. That is to say, at the temperature the meltable material liquefies, the substrate and other metals in the substrate does not liquefy (readily tested as set forth in Example 6) and does not change its properties. By "changing properties" it is meant that the substrate or metal maintains it structural integrity, does not change its conductivity and does not liquefy. Thus, the characteristic of being meltable is not necessarily associated with a particular melting point. Examples include, but are not limited to, solder, wax, polymer and plastic.

In certain aspects of the invention "solder" may refer to a metal or alloy that is a meltable material. Preferably, the solder is a lower temperature solder, such as set forth in U.S. Pat. No. 4,967,950, herein incorporated by reference. "Lower temperature solder" means a eutectic alloy. While the present invention is not limited to a specific solder, one preferred solder composition for the paste is a 63:37 eutectic alloy of tin:lead. Another compatible solder is a 90% metal composition having a 63:35:2 eutectic alloy of tin:lead:silver. Other desired solder compositions such as eutectic Pb:Sn, Pb:In, Pb:In:Sn, etc.

The present invention also contemplates a method for restricting fluid flow in a channel, comprising providing a main channel connected to a side channel and disposed within a substrate, meltable material disposed within the side channel and associated with a heating element, and a movement means connected to the side channel such that application of the movement means induces the meltable material to flow from the side channel into the main channel, heating the meltable material such that the meltable material at least partially liquefies, and applying the movement means such that the liquefied meltable material flows from the side channel into the main channel. While the present invention is not limited by the movement means, in one embodiment the movement means is forced air. In one embodiment the method further comprises allowing the meltable material to cool. While the present invention is not limited by the size of the channel, in one embodiment, the main channel and the side channel are microdroplet channels.

While the present invention is not limited by the nature of the substrate, in one embodiment the substrate comprises silicon or glass. Likewise, the present invention is not limited by the composition of the meltable material. In one embodiment, the meltable material comprises solder. In a preferred embodiment, the solder comprises 40:60 Sn:Pb. In other embodiments, the meltable material is selected from a group consisting of plastic, polymer and wax. Likewise, the present invention is not limited by the placement of the meltable material in the substrate. In another embodiment, the meltable material is placed adjacent to a channel, while in another embodiment it is placed near the junction of more than one channel.

II. MICROFABRICATION OF SILICON-BASED DEVICES

As noted previously, silicon has well-known fabrication characteristics and associated photographic reproduction techniques. The principal modem method for fabricating semiconductor integrated circuits is the so-called planar process. The planar process relies on the unique characteristics of silicon and comprises a complex sequence of manufacturing steps involving deposition, oxidation, photolithography, diffusion and/or ion implantation, and metallization, to fabricate a "layered" integrated circuit device in a silicon substrate. See e.g., Miller, U.S. Pat. No. 5,091,328, hereby incorporated by reference.

For example, oxidation of a crystalline silicon substrate results in the formation of a layer of silicon dioxide on the substrate surface. Photolithography can then be used to selectively pattern and etch the silicon dioxide layer to expose a portion of the underlying substrate. These openings in the silicon dioxide layer allow for the introduction ("doping") of ions ("dopant") into defined areas of the underlying silicon. The silicon dioxide acts as a mask; that is, doping only occurs where there are openings. Careful control of the doping process and of the type of dopant allows for the creation of localized areas of different electrical resistivity in the silicon. The particular placement of acceptor ion-doped (positive free hole, "p") regions and donor ion-doped (negative free electron, "n") regions in large part defines the interrelated design of the transistors, resistors, capacitors and other circuit elements on the silicon wafer. Electrical interconnection and contact to the various p or n regions that make up the integrated circuit is made by a deposition of a thin film of conductive material, usually aluminum or polysilicon, thereby finalizing the design of the integrated circuit.

Of course, the particular fabrication process and sequence used will depend on the desired characteristics of the device. Today, one can choose from among a wide variety of devices and circuits to implement a desired digital or analog logic feature.

In a preferred embodiment, channels were prepared on 500 $\mu$m thick glass wafers (Dow Corning 7740) using standard aqueous-based etch procedures. The initial glass surface was cleaned and received two layers of electron beam evaporated metal (20 nm chromium followed by 50 nm gold). Photoresist Microposit 1813 (Shipley Co.) was applied 4000 rpm, 30 sec; patterned using glass mask 1 and developed. The metal layers were etched in chromium etchant (Cr-14, Cyantek Inc.,) and gold etchant (Gold Etchant TFA, Transene Co.,) until the pattern was clearly visible on the glass surface. The accessible glass was then etched in a solution of hydrofluoric acid and water (1:1, v/v). Etch rates were estimated using test wafers, with the final etch typically giving channel depths of 20 to 30 $\mu$m. For each wafer, the depth of the finished channel was determined using a surface profilometer. The final stripping (PRS-2000, J. T. Baker) removed both the remaining photoresist material and the overlying metal.

In one embodiment, channels etched on glass in the above-described manner, were bonded to the heater-element wafer in a two-part construction approach using optical adhesive (SK-9 Lens Bond, Sumers Laboratories, Fort Washington, Pa.). The bond was cured under an ultraviolet light source (365 nm) for 12 to 24 h.

Initial device design involved single layers of silicon. However, experience showed these to be inadequate to prevent short circuiting due to (necessary) liquid microdroplets within the channels (see studies described below). The preferred design involves a triple layer of oxides. Such a preferred device capable of moving and mixing nanoliter droplets was constructed by bonding a planar silicon substrate to channels etched in a glass cover. A series of metal heaters was inlaid on the silicon substrate as two parallel lanes merging into a single lane (a "Y"-shape). The heating elements were formed by first coating the wafer with a 1.0 $\mu$m layer of thermal silicon dioxide. Next, 0.35 $\mu$m deep, 5 $\mu$m wide grooves were reactive-ion etched (RIE) into the silicon dioxide following the pattern set in an overlying photoresist. Aluminum was deposited (0.35 $\mu$m) across the entire wafer using electron beam evaporation and the metal layer was "lifted-off" from all surfaces having intact photoresist using a stripping solution. The metal inlay process gives a relatively planar surface and provides a uniform base for deposition of a solution-impermeable barrier layer. The barrier layer is made by a sequence of three plasma-enhanced chemical vapor depositions (PECVD): 1.0 $\mu$m silicon oxide ($SiO_x$), 0.25 $\mu$m silicon nitride ($Si_xN_y$) and 1.0 $\mu$m silicon oxide ($SiO_x$). Some heating elements were also used as resistive temperature sensors.

Heater elements were fabricated as follows. Silicon wafer (p-type, 18–22½-cm, boron concentration Å $10^{15}$ $cm^{-3}$) was used as a substrate for growth of $SiO_2$ thermal oxide (1 $\mu$m); photoresist (AZ-5214-E, Hoescht-Celanese) was applied and spun at 3000 rpm, 30 sec. The resist was patterned (metal 1) and developed. Reactive ion etch (RIE, PlasmaTherm, Inc.) was performed to 0.35 $\mu$m depth into the $SiO_2$ layer at the following conditions: $CHF_3$, 15 sccm (standard cubic centimeters per min); $CF_4$, 15 sccm; 4 mTorr; DC bias voltage of 200V, 100 W, 20 min. The etch depth was measured by profilometer and 0.35 $\mu$m metallic aluminum was electron beam deposited. The resist and overlying metal was lifted off by development using Microposit 1112A remover in solution (Shipley Co.,). The barrier layers consist of sequentially deposited 1 $\mu$m $SiO_x$, 0.25 $\mu$m $Si_xN_y$, and 1 $\mu$m $SiO_x$ using plasma-enhanced chemical vapor deposition (PECVD). RIE was used to etch contact holes to the metal layer using a second mask ($CHF_3$, 15 sccm; $CF_4$, 15 seem; 4 mTorr; and DC bias voltage of 200V, 100 W, 120 min).

The elements are arrayed as two parallel lanes, each 500 $\mu$m wide, merging into one lane. The individual heaters consist of paired aluminum wires (5 $\mu$m) winding across the 500 $\mu$m wide region. The broad metal areas on either side of the elements are bonding locations for connection to external circuitry. The width of the aluminum element is 5 $\mu$m. The channel is uniformly etched 500 $\mu$m wide and approximately 20 $\mu$m deep.

The heating-element wafer was bonded to a glass wafer containing etched channels with the same "Y" format. An aqueous chemical etch of concentrated hydrofluoric acid was used to produce channels with defined side walls and uniform depth. The etched channels are defined by a chromium/gold mask and are 500 $\mu$m wide and approximately 20 $\mu$m deep. The complementary silicon heater and glass channel wafers were aligned and then bonded with adhesive to form the finished device.

Each heating element used as a temperature sensor is preferably first calibrated by measurement of electrical resistance at 22° C. and 65° C. under constant voltage; intermediate temperatures are estimated by linear interpolation.

A. Microchannel Construction

There are two basic techniques that may be used for construction of channel structures. The first technique uses a chemical or a reactive ion etch to form open channels on selected areas of a substrate. These channels can range in width from 10 $\mu$m to the full thickness of the wafer (500 $\mu$m). The open channels are sealed by bonding of a second substrate as a cap on top of the first one. Common bonding techniques include anodic bonding, fusion bonding, melting, and epoxy bonding. Holes at specific locations for injection of the sample are then etched from the backside of the cap wafer. Bonded structures have been successfully applied in the implementation of capillary liquid electrophoresis systems etched on glass substrates (Burggraf et al., 1993,; Harrison et al., 1993). Most bonded structures are simple discrete channel devices with a limited number of electrical components and interconnects. However, the bonded nature of the device means that the substrate material containing the electrical components may be different than the cap material, adding great flexibility to device design.

The second technique for the fabrication of channels relies on the sacrificial etch technique (Mastrangelo and Muller 1989). In this technique, the channel is formed from a patterned thin film that determines the channel height. The film is covered by the deposition of a thick cap material and access holes are opened through it. The sacrificial material defining the channel is next removed by chemical etching through the access holes, and finally the channel is sealed by plugging the access holes. The main advantage of this fabrication approach is that the channel fabrication takes place entirely on one side of the substrate; hence this technique is referred as surface micromachining. The ability to pattern channels on the surface of the substrate brings a great deal of flexibility. Surface micromachined channels may be fabricated on substrates with complex topographies of interconnects, sensors, and control electronics. In surface micromachined devices, the analytical instrumentation is built along with the channel on the same physical substrate.

The devices by both the hybrid (bonded) and monolithic (surface machining) designs have been constructed. For bonded structures, both glass and silicon substrates to form channels (500 $\mu$m wide), and t-circuits (aluminum heater circuitry, each wire filament is 5 $\mu$m wide) have been used. The monolithic device is compatible with conventional NMOS device fabrication.

B. Channel Fabrication

The channels are made of diffused silicon on the bottom and a thin film cap on the top. This type of channel may be routed through low-mass diaphragm-type heaters needed for the reaction. On the top layer, a set of thin film electrodes and heaters is constructed. Both the channels and entry port components can be formed by etching of silicon. The depth of etching can be controlled by prior doping of the silicon material with an etch stop (boron).

The surface treatment of the channels may be done by immersing the open channel in organosilane or a self-assembled monolayer coating, with oxygen reactive ion etching removing the surface from unwanted areas. Heating elements, dielectric sensors, and connecting wires may be made from sputtered aluminum metal and conventional masking. The sequential activation of heating elements can be computer controlled through external circuitry, and a printed circuit board connector.

C. Channel Treatment

Prior to performing microdroplet motion and biological reactions, the channels are preferably treated by washing with base, acid, buffer, water and a hydrophilicity-enhancing compound, followed by a relatively high concentration solution of non-specific protein. "Hydrophilicity-enhancing compounds" are those compounds or preparations that enhance the hydrophilicity of a component, such as the hydrophilicity of a transport channel. The definition is functional, rather than structural. For example, Rain-X™ anti-fog is a commercially available reagent containing glycols and siloxanes in ethyl alcohol. However, the fact that it renders a glass or silicon surface more hydrophilic is more important than the reagent's particular formula.

"Hydrophobic reagents" are used to make "hydrophobic coatings" in channels. It is not intended that the present invention be limited to particular hydrophobic reagents. In one embodiment, the present invention contemplates hydrophobic polymer molecules that can be grafted chemically to the silicon oxide surface. Such polymer molecules include, but are not limited to, polydimethylsiloxane. In another embodiment, the present invention contemplates the use of silanes to make hydrophobic coatings, including but not limited to halogenated silanes and alkylsilanes. In this regard, it is not intended that the present invention be limited to particular silanes; the selection of the silane is only limited in a functional sense, ie., that it render the surface hydrophobic.

In various aspects of the invention, n-octadecyltrichlorosilane (OTS), octadecyldimethylchlorosilane, 1H, 1H, 2H, 2H-perfluorodecyltricholorosilane (FDTS, $C_{10}H_4F_{17}SiCl_3$), fluoroalkyl-, aminoalkyl-, phenyl-, vinyl-, bis silyl ethane- or 3-methacryloxypropyltrimethoxysilane (MAOP) are contemplated as hydrophobic reagents. Such reagents (or mixtures thereof) are useful for making hydrophobic coatings, and more preferably, useful for making regions of a channel hydrophobic (as distinct from coating the entire channel).

In a preferred embodiment, the channels are washed with approximately 100 µl each of the following solutions in series: 0.1N NaOH; 0.1N HCl; 10 mM Tris-HCl (pH 8.0), deionized, $H_2O$, Rain-X Anti-Fog (a hydrophilicity-enhancing compound commercially available from Unelko Corp., Scottsdale, Ariz.), and 500 µg/µl bovine serum albumin (non-specific protein commercially available in restriction enzyme grade from GIBCO-BRL). The wafer was placed on a stereoscope stage (Olympus SZ1145), and the contact pads for the heating elements were connected to a regulated power supply. Heating occurred by passing approximately 30 volts through the element in short pulses and observing the movement rate of the droplets. A detectable reduction in droplet volume from evaporation was noted in each study, usually of less than 30%. Droplet movement was recorded with a Hamamatsu video camera on videotape.

It is not intended that the present invention be limited to particular dimensions for the hydrophobic regions of the present invention. While a variety of dimensions are possible, it is generally preferred that the regions have a width of between approximately 10 and 1000 µm (or greater if desired), and more preferably between approximately 100 and 500 µm.

A surface (such as a channel surface) is "hydrophobic" when it displays advancing contact angles for water greater than approximately seventy degrees. In one embodiment, the treated channel surfaces of the present invention display advancing contact angles for water between approximately ninety (90) and approximately one hundred and thirty (130) degrees. In another embodiment, the treated microchannels have regions displaying advancing contact angles for water greater than approximately one hundred and thirty (130) degrees.

D. Glass Channel and Chamber Fabrication

The channel and the chamber fabrication begins by depositing 0.4 µm metallic layer of Gold (Electron beam deposition) on the surface of 500 µm thick glass water (Dow Coming 7740). A 0.06 µm layer of chromium is used as the adhesion layer. Photoresist is applied and patterned using glass mask 1 and developed. The metal layers are etched in gold etchant (Gold Etchant TFA, Transene Co.) and Chromium etchant (CR-14, Cyantec Inc.). The accessible glass is then etched in a solution of freshly prepared hydrofluoric and nitric acid (7:3, v/v). The etch rate is approximately 5 µm/min and the etch depth is conveniently measured using a surface profilometer. The metal layers are removed and the wafer rinsed in DI water, air dried and oven dried at 100° C. for 20 min. The following processing steps are done for patterning hydrophobic regions onto the glass surface.

1. Hydrophobic Patterning of Glass Substrate

A 1.5 µm thick aluminum layer was electron beam deposited, covering the etched channels and chamber. A thick photoresist (AZ 4620) is applied and spun at 750 rpm for 50 sec. The resist is patterned (SAM Mask) and developed. The exposed aluminum is etched in aluminum etchant. The photoresist is stripped off in hot PRS 2000 (J. T. Baker). The samples are then cleaned in acetone, isopropyl alcohol and DI water for 5 min each and the water dried off in a 100° C. oven of 10–15 min. The samples are then dipped in a 1% OTS solution in toluene for 10–15 min. The SAM deposition was carried out in a chemical hood. The samples were then rinsed in toluene, isopropyl alcohol and DI water for 5 min each. Next, they were put in aluminum etchant until all metallic aluminum was removed. The samples were then rinsed in DI water and air dried. For the devices with the inlet from the top, holes were drilled by electrochemical discharge drilling.

The glass side was then aligned on top of the silicon side and then bonded together using optical adhesive (SK-9 Lens Bond, Sumers Laboratories, Fort Washington, Pa.). The bond was cured under an ultraviolet light source (365 nm) for 24 h.

E. Heaters and Resistive Temperature Detectors

The fabrication process for the heater and temperature detector begins by using Silicon water (p-type, 18–22 aluncm, boron concentration ~$10^{15}$ cm$^3$) as a substrate for growth of S102 thermal oxide (1 µm). A 0.5 µm metallic Aluminum film is electron beam deposited. Photoresist PR 1827 is applied and spun at 4000 rpm for 30 sec, patterned (metal 1) and developed. The exposed aluminum is etched in aluminum etchant and the photoresist stripped to define the metal heater.

Photoresist is spun again and a second lithography is done (metal 2). A 0.15 µm layer of platinum ("Pt") is electron beam deposited. A 0.03 µm thick titanium metal layer (electron beam deposited) is used as the adhesion layer. The resist and the overlying metal is lifted off by development using Microposit 1112A remover in solution (Shipley Co.). This platinum metal will be used as the resistive thermal detector. Next, 0.7 µm of low temperature oxide (LTO) of silicon is deposited to act as the barrier layer and the hydrophilic substrate. A third lithography is done and the LTO is etched in buffered hydrofluoric acid to open contacts to the metal contact pads. The further processing steps are done to pattern hydrophobic regions onto the hydrophilic silicon oxide surface.

1. Hydrophobic Patterning of Silicon Oxide Substrate

A 0.1 µm layer of chromium metal is electronbeam deposited on the processed water. Photoresist PR 1827 is applied and spun at 2000 rpm for 30 sec. The resist is patterned (SAM mask) and developed. The exposed chromium metal is etched in chromium etchant to expose the silicon oxide and the photoresist is then stripped off. The samples are then cleaned in acetone, isopropyl alcohol and DI water for 10 min each, air dried and oven dried at 100° C. for 5 min. The samples are then put in 1 wt % octadecyltrichlorosilane (OTS) solution in toluene for 15–30 min. OTS deposits on the samples as a self assembled monolayer (SAM). The samples are then rinsed in toluene, isopropyl alcohol and DI water for 5 min each, and then oven dried (100° C., 5 min). Next, they are put in chromium etchant to remove the chromium layer below. The SAM on the chromium metal gets lifted off as a result of this. The samples were then rinsed in DI water and air dried, resulting in regions of intact hydrophobic regions on a hydrophilic oxide substrate. Heater elements and RTDs have also been fabricated on a quartz substrate. The fabrication steps are similar to that of the silicon processing steps.

Once the appropriate chemicals are added to the DNA sample, the solution may be passed through several different temperatures. The mixed solution may be transported to a uniformly heated reaction chamber of the unit. Once in the chamber, the temperature of the solution may be increased using local heaters and temperature sensors. The temperature of the ends of the drops may be monitored and maintained at the same temperature to prevent the drop from leaving the reaction zone. If the drop does begin to move, local temperature gradients could quickly stabilize the drop. The cooling of the drop may be accomplished by simple conduction of the heat through the walls of the channel to ambient temperature.

F. Fluid Mixing Chamber

The mixing chamber consists of an enlarged portion of the microchannel structure, with one or more microchannels connected to the chamber. The mixing chamber is suspended on a thin silicon nitride diaphragm. This construction allows for excellent thermal isolation, as needed for low power heat cycling of the mixture. Construction of membrane suspended structures has been demonstrated (Mastrangelo et al., 1991). The heating is effected with a set of concentric resistors (heaters) that are placed on the periphery of the mixing chamber. This design, along with the high thermal conductivity of the liquid sample, makes the chamber temperature quite uniform. Along with the heaters, temperature sensors (diodes) are constructed on the diaphragm to monitor the temperature of the mixture. The low mass construction of the chamber allows for rapid heating cycles. Temperature control may handle samples of variable volume and heat capacity. The chamber also contains a set of electrodes and heating elements to drive the mixture out of the chamber at the completion of the reaction.

G. Electrophoresis and Detector Component Design

The present invention contemplates one or more gel electrophoresis modules as a component of the microscale device. Reducing the thickness of the electrophoresis channel may improve resolution. Thinner gels dissipate heat more readily and allow higher voltages to be used, with concomitant improvements in separation. The position and width of the electrophoresis detector are also critical to the ultimate resolution of the electrophoresis system. A micromachined electronic detector, such as a photodiode, placed in the underlying silicon substrate may be less than one micron from the gel matrix and can have a width of 5 microns or less. Since the gel length required for the resolution of two migrating bands is proportional to the resolution of the detector, the incorporation of micron-width electronic detectors can reduce the total gel length required for standard genotyping by at least an order of magnitude.

To demonstrate that standard gel electrophoresis can operate in micron-diameter channels, modules were fabricated using etched glass channels and fluorescent-labeled DNA (YOYO intercalating dye). Polyacrylamide gel electrophoresis of a complex DNA mixture was performed in a channel 500 µm wide and 20 µm deep. The electrophoresis was performed with the positive electrode to the right and the DNA sample applied at the left. The DNA sample (Bluescript KS digested with MspI) is labeled with intercalating UV-fluorescent dye (YOYO-1) and is visualized under incandescent light. Separation of the component bands is clearly visible less than 300/µm from the buffer reservoir-to-gel interface. The high resolution of the detector (in this case, a microscope) allowed the use of an unusually short gel, resolving several closely eluting bands.

H. Miniature Electrophoresis Chamber

A 20 µm×500 µm×4 cm channel etched into a glass wafer was used as an electrophoresis chamber. The channels may be made by three different processes: a glass channel wet-etched, a silicon channel dry-etched (RIE), or a silicon channel wet-etched. Although the edges of the channel are rough and the walls of the channels are not vertical, the floor of the channel is quite smooth. Better channels may also be constructed with silicon as the base material using dry or wet etching. The glass channel was then bonded to a quartz slide using UV-cure cement and loaded with a 15% polyacrylamide gel and 1×TBE running buffer. The gel was loaded with DNA ladder (BSKS/MSPI 50–500 bp), stained with TOTO fluorescent dye, and placed in a ~3 volt/cm field for 30 minutes. At these short times and low voltages, separation into visibly resolved bands is obtained.

I. Integrated Electrophoresis/Detection Device

Monolithic devices created from silicon have the advantage that no bonding is necessary and that electronic components may be integrated with the mechanical system in any location. A silicon micromachined gel electrophoresis channel integrated with a silicon radiation/fluorescence detector underneath it was fabricated. The "die" measures 1.25×1.25 cm and contains about 20 different types of gel devices. Among these devices, the channel width varies from 20 to 150 µm, and the channel height is approximately 3 µm. There are different channel formats including straight, folded, and looped channels, each of which has at least one DNA detector. The longest channel on this wafer is a 9.5 cm long folded channel. For folded channels, as long as the channel bends are paired curves, it may be shown that the electric field is uniform around the bend and the solute bands start and end as uniform bands.

The structure primarily comprising a silicon diffused diode detector (Kemmer, 1980; Wouters and van Sprakelaar 1993) fabricated underneath a gel channel. The diode is fabricated on a high purity p-type float zone substrate to assure a good carrier lifetime. A layer of silicon dioxide is used as a passivation layer below a silicon nitride blocking layer. The electrodes for the electrophoresis stage are formed by deposition and patterning of n+polycrystalline silicon. The channel for the microgel is built with two layers of phosphoslicate glass as described in Mastrangelo and Muller 1989; Mastrangelo and Muller 1989. The cap of the channel is deposited using a thin silicon nitride dielectric and a 2 m-thick undoped polysilicon shell. A series of etching holes are patterned on the side or top of the shell down to the phosphosilicate glass and used to sacrificially etch the phosphosilicate glass (Mastrangelo and Muller, 1989) thus forming the channel cavity. The cavity can then be refilled with polyacrylamide gel.

The invention has tested the radiation/fluorescence detectors and performed simple DNA separations with them. The experiments were performed using a $P^{32}$ labeled DNA source placed on top of the detector. Note that the chip used for this test did not have the channels formed on the surface and contained as an insulating layer. Pulse-shaped (Knoll, 1989) scope traces or the measured signals from the diode detector were detected from sample DNA. Not only is the response rapid ($\approx 1$ $\mu$s), but a single decay event (each trace is from only one particle) may be detected.

Fluorescent DNA may also be detected with the same detector. A detector was mounted in a 24 pin IC package and covered with a SYBR green gel filter (the filter was ~1 cm from the detector surface). A glass slide was placed over the filter and ~40 $\mu$l of 0.03 $\mu$g/$\mu$g of SYBR green labeled DNA solution was placed on the slide (contained by silicon grease wells). The sample was illuminated using a Ziess Axioskop UV source with a ~490 nm filter. The reverse current was measured with an HP 4145B semiconductor parameter analyzer as a function of the bias voltage. The signal from the SYBR sample is approximately twice the control signal (DI water). Although this experiment was not performed under optimum conditions, it clearly demonstrates that the detector is capable of detecting fluorescent DNA.

Sample separation experiments have also been performed using this detector. A 100 $\mu$m ID capillary tube filled with 10% polyacrylamide was glued on top of a detector (same as that described above) approximately 1.5 cm from the sample injection end. A 100 bp and a 300 bp PCR™ product (50/50 mixture) was electrokinetically injected into the channel for approximately 5 min using a field of 25 V/cm after which the sample well was flushed and refilled with running buffer. The results of the 125 minute run show the detection of the radioactive primers and the two PCR™ products. Note that, although the radiation detection scheme may not be used in the final sequencing system, it is very useful to evaluate the electrophoresis chambers until the necessary, fluorescent filters are constructed and tested.

The present invention contemplates an electrophoresis unit that integrates a micromachined channel and an electronic DNA detector. The channel is constructed using a sacrificial etch process on a single silicon wafer rather than the bonded surface-etch method described earlier. In the sacrificial etch technique, the channel configuration is patterned by depositing on the wafer surface an etch-sensitive material (phosphosilicate glass, $SiO_2 \cdot P_x$) with a thickness equivalent to the desired channel height. A triple-layer overlay of plasma-enhanced chemical vapor deposited silicon nitride, undoped polycrystalline silicon, and silicon nitride ($Si_xN_y$/polySi/$Si_xN_y$) completely covers the sacrificial material with the exception of small access holes on the top or sides. A selective liquid etch removes the sacrificial layer material, but not the overlay or the underlying substrate. The sacrificial etch technique results in a complete channel being formed directly on the substrate containing the electronic components. The 3 $\mu$m deep channel has two buffer reservoirs on either end with integral phosphorus-doped polycrystalline silicon electrodes. The channel height formed by this technique (~3/$\mu$m) is considerably smaller than the height of the bonded structures due to the limitations of the sacrificial layer deposition and the strength of the overlying layer. Note that, for these channel dimensions, liquid drops would have volumes on the order of picoliters.

The diffusion regions of the doped-diffusion diode radiation detector elements fabricated on a silicon wafer are approximately 300 $\mu$m long and 4 $\mu$m wide, and are flanked by the guard ring shielding electrodes.

A radiation detector, consisting of a 10 $\mu$m wide "p-n"-type diode with a 5 $\mu$m wide guard ring around the outer edge, is fashioned directly into the silicon substrate underneath the channel. In this implementation, an integral radiation detector was chosen because of high sensitivity (a single decay event), small aperture dimensions, and well-know fabrication and response characteristics. On this electrophoresis system, a 1 cm long, 3 $\mu$m thick gel is able to perform as separation on a 80 and a 300 base-pair fragment of DNA. It should be noted that this diode, although currently configured for high-energy beta particle detection, can also operate as a photon detector. With proper wavelength filters and light sources, detection of fluorescence emission may be accommodated with a similar device.

Radiation detectors were prepared as follows. A 200½-cm, float zone, boron-doped, p-type silicon wafer was used as a substrate. Diffused layers of phosphorus ($5\times10^{14}$ $cm^{-2}$) and boron ($1\times10^{15}$ $cm^{-2}$) were ion-implanted onto the sample in lithographically-defined regions; thermal silicon oxide was grown (0.2 $\mu$m at 900° C.) over the wafer; and contact holes were etched to the diffusion layer using buffered hydrofluoric acid solution (5:1). A 3.3 $\mu$m layer of Microposit 1400-37 photoresist was patterned to define the metal pads; 50 nm chromium followed by 400 nm gold was evaporated over the resist; and the metallization lifted off the regions retaining the resist. A layer of Microposit 1813 photoresist was applied across the wafer and baked for 110° C. for 30 min to form an aqueous solution barrier. Radioactive phosphorus ($^{32}$P) decay events could be detected using a sample of labeled DNA in PCR™ reaction buffer placed on the photoresist layer. The detector was connected to a charge-sensitive preamplifier (EV-Products 550A), followed by a linear shaping amplifier and a standard oscilloscope.

An oscilloscope trace of output from the radiation detector showing individual decay events from $^{32}$P-labeled DNA was generated after the aqueous DNA sample was placed directly on the detector and sampled for 30 sec. The screen is displaying a vertical scale of 0.5V/division and horizontal scale of 20 $\mu$sec/division.

J. Gel Voltage and Temperature Control Circuits

The control circuitry and software for the integrated DNA sample processing and sequencing devices are a further aspect of the invention. In particular, the devices will require circuitry for signal buffering and for the multiplexing of control signals. A microprocessor, either external or on-wafer, determines the synchronization of events on the device and store the output information.

Temperature control of gel occurs by heating with polysilicon or thin metal resistors imbedded in the surface of the wafer immediately beneath the channel. The precise temperature control of the gel is required as minute fluctuations contribute to the dispersion of the migrating sample and non-uniform bands. The power distribution and optimal heater placement is determined for each electrophoresis design by solving the relevant heat transfer equations. As long as the walls of the electrophoresis channel are maintained at the appropriate temperature and the height of the channel is constructed uniformly, the internal temperature of the across the gel should not vary by more than 1.0° C. and be maintained at any arbitrary temperature.

Although the electrophoresis voltages may be low, the potential use of high voltages in the gel electrophoresis channels will necessitate care in fabricating the silicon oxide/silicon nitride/silicon oxide insulating layer. Silicon nitride and silicon oxide have a breakdown field voltage of about 200–1000 V/$\mu$m (Sze, 1967; Harari, 1977; Sze, 1981). Consequently, the layers between the silicon circuitry (including the diode detectors) and the electrically active gel are approximately 2 to 4 microns thick. The possible presence of minute "pinholes" in the LPCVD deposited layers must also be carefully monitored, since such holes can provide local weak points in the insulation of the silicon circuitry. However, the routine use of silicon nitride as a mask for wet etch processes in solid-state fabrication indicate that pinholes are insignificant.

Glass may be used as their substrate material. In a glass-based device, any associated on-wafer circuitry must be constructed on polysilicon thin films adjacent to the electrophoresis channels (Tickle, 1969). As an alternative are designs that energize small fractions of the channel at a time, thereby decreasing the voltage required without sacrificing resolution. Cyclical or "loop" 9.5 cm channels were constructed to test this (Sun and Hartwick, 1994). However, since active electrodes are in immediate contact with the get matrix care must be exercised so as not to irreversibly adsorb the DNA samples on the electrodes. Alternative gel channel designs are possible.

In one embodiment of the device of the present invention, the device comprises a glass top bonded to a silicon substrate containing the heater, the contact pad and the resistive temperature detector. The glass side has channels and chambers etched into it. Inlet and overflow ports, a gas vent and a air chamber are also part of this embodiment.

III. FLUID MOVEMENT

The present invention contemplates a method for moving microdroplets, comprising providing a liquid microdroplet disposed within a microdroplet transport channel etched in silicon, the channel in liquid communication with a reaction region via the transport channel and separated from a microdroplet flow-directing means by a liquid barrier, and conveying the microdroplet in the transport channel to the reaction region via the microdroplet flow-directing means. It is intended that the present invention be limited by the particular nature of the microdroplet flow-directing means. In one embodiment, it comprises a series of aluminum heating elements arrayed along the transport channel and the microdroplets are conveyed by differential heating of the microdroplet by the heating elements.

It has been found empirically that the methods and devices of the present invention may be used with success when, prior to the conveying described above the transport channel (or channels) is treated with a hydrophilicity-enhancing compound. It is not intended that the invention be limited by exactly when the treatment takes place. Indeed, there is some flexibility because of the long-life characteristics of some enhancing compounds.

It has also been found empirically that the methods and devices of the present invention may be used with success when regions of the microchannel are treated with hydrophobic reagents to create hydrophobic regions. By using defined, hydrophobic regions at definite locations in microchannels and using a pressure source, one can split off precise nanoliter volume liquid drops (i.e., microdroplets) and control the motion of those drops though the microchannels.

In one embodiment employing such hydrophobic regions (or "hydrophobic patches"), the present invention contemplates a method for moving microdroplets, comprising providing microdroplet transport channel (or a device comprising a microdroplet transport channel), the channel having one or more hydrophobic regions and in communication with a gas source; introducing liquid into the channel under conditions such that the liquid stops at one of the hydrophobic regions so as to define a source of liquid microdroplets disposed within the channel and a liquid-abutting hydrophobic region, and separating a discrete amount of liquid from the source of liquid microdroplets using gas from the gas source under conditions such that a microdroplet of defined size comes in contact with, and moves over, the liquid-abutting hydrophobic region.

In one embodiment, the gas from the gas source enters the channel from a gas-intake pathway in communication with the microdroplet transport channel and exits the channel from a gas vent that is also in communication with the microdroplet transport channel. It is preferred, in this embodiment, that the introduction of liquid into the channel (as set forth in the above-described method) is such that the liquid passes over the gas-intake pathway and the desired size of the microdroplet is defined by the distance between the gas-intake pathway and the liquid-abutting hydrophobic region. In this embodiment, introduction of the gas (as set forth in the above-described method) forces the microdroplet to pass over the liquid-abutting hydrophobic region and pass by (but not enter) the gas vent.

In another embodiment employing such hydrophobic regions (or "hydrophobic patches"), the present invention contemplates a method for moving microdroplets, comprising: providing a device comprising a microdroplet transport channel etched in silicon, the channel having one or more hydrophobic regions and in communication with a gas source; introducing liquid into the channel under conditions such that the liquid stops at one of the hydrophobic regions so as to defined a source of liquid microdroplets disposed within the channel and a liquid abutting hydrophobic region, and separating a discrete amount of liquid from the source of liquid microdroplets using gas from the gas source under conditions such that a microdroplet of defined size comes in contact with, and moves over, the liquid-abutting hydrophobic region.

Again, it has been found empirically that there is a need for a liquid barrier between the liquid in the channels and the electronics of the silicon chip. A preferred barrier comprises a first silicon oxide layer, a silicon nitride layer, and a second silicon oxide layer.

The present invention further contemplates a method for merging microdroplets comprising providing first and second liquid microdroplets, a liquid microdroplet delivering means, and a device, said device comprising a housing comprised of silicon, first and second microdroplet transport channels etched in the silicon and connecting to form a third transport channel containing a reaction region, a microdroplet receiving means in liquid communication with the reaction region via the transport channels, and microdroplet flow-directing means arrayed along the first, second and third transport channels delivering the first liquid microdroplet via the microdroplet delivering means to the first transport channel, delivering the second liquid microdroplet via the microdroplet delivering means to the second transport channel, and conveying the microdroplets in the transport channels to the reaction region in the third transport channel via the microdroplet flow-directing means, thereby merging the first and second microdroplets to create a merged microdroplet.

In one embodiment, said first microdroplet comprises nucleic acid and the second microdroplet comprises a nuclease capable of acting on the nucleic acid. In this embodiment, it is desirable to enhance the mixing within the merged microdroplet. This may be achieved a number of ways. In one embodiment for mixing, after the conveying of step, the flow direction is reversed. It is not intended that the present invention be limited by the nature or number of reversals. If the flow direction of the merged microdroplet is reversed even a single time, this process increases the mixing of the reactants.

The present invention contemplates methods, compositions and devices for the creation of microdroplets of discrete (ie., controlled and predetermined) size. The present invention contemplates the use of selective hydrophobic coatings to develop a liquid-sample injection and motion system that does not require the use of valves. In one embodiment, the present invention contemplates a method of lift-off to pattern hydrophobic and hydrophilic regions on glass, quartz and silicon substrates, involving the deposition of a hydrophobic reagent (such as a self-assembled monolayer film of OTS) on a silicon oxide surface patterned by a metal layer and subsequent removal of the metal to give hydrophobic patterns. Other substrates such as plastics may also be used after depositing a think film of silicon oxide or spin-on-glass.

Previous work in patterning hydrophobic surfaces have been done by photocleaving of such monolayer films. The photocleaving procedure uses Deep-UV exposure to make the molecules of the monolayer hydrophilic. By contrast, the present invention contemplates a method which eliminates the use of high-power UV source; rather the preferred method of the present invention uses microfabrication procedures.

Following the proper hydrophobic patterning of the surface (e.g., the surface of a microdroplet transport channel), the present invention contemplates the placement of a patterned etched glass cap over the pattern on a flat surface. The hydrophobic/hydrophilic channels thus formed can then be used to move precise nanoliter-volume liquid samples.

Figure 3A:
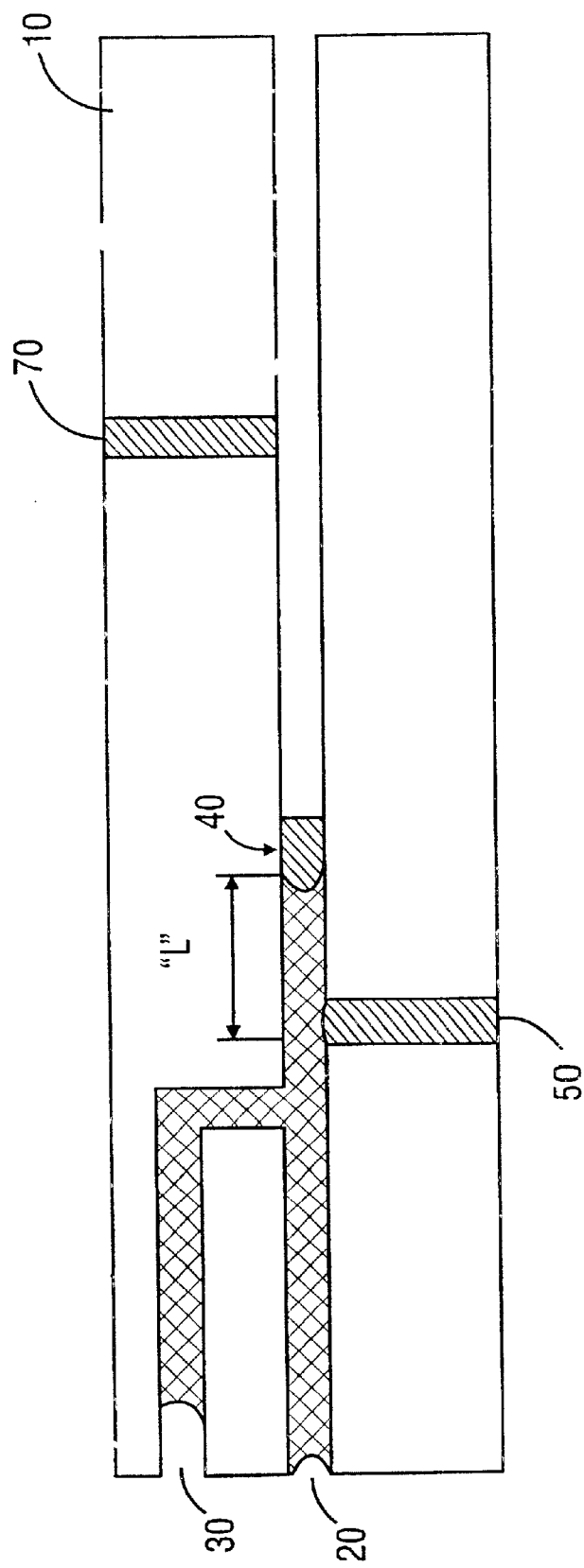
FIG. 3A and FIG. 3B. A schematic of one embodiment of a device to split a nanoliter-volume liquid sample and move it using gas from a gas source.
Figure 3B:
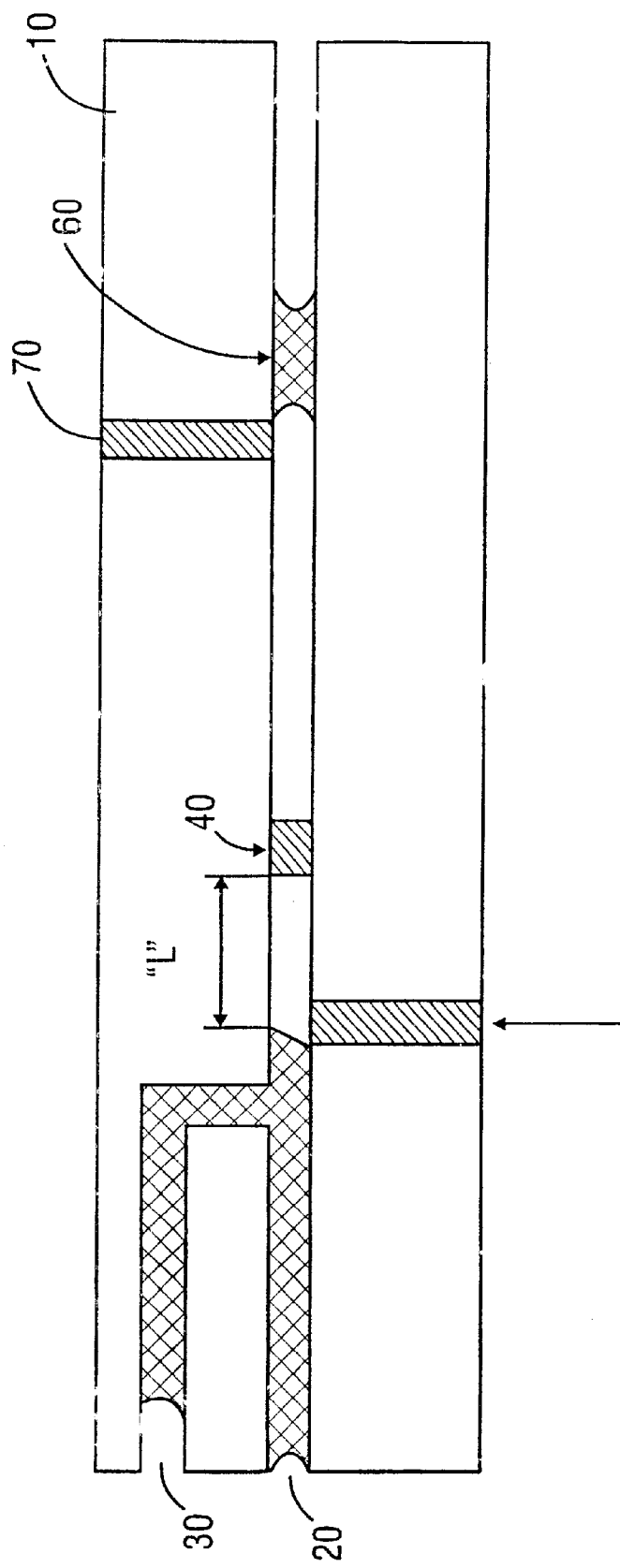

FIG. 3A and FIG. 3B show a schematic of one embodiment of a device (10) to split a nanoliter-volume liquid sample and move it using external air, said device having a plurality of hydrophobic regions (hatched regions). Looking at FIG. 3A, liquid (shown as solid black) placed at the inlet (20) is drawn in by surface forces and stops in the channel at the liquid-abutting hydrophobic region (40), with overflow handled by an overflow channel and overflow outlet (30). In the embodiment shown in FIG. 3A, the from of the liquid moves by (but does not enter) a gas-intake pathway (50) that is in fluidic communication with the channel; the liquid-abutting hydrophobic region (40) causes the liquid to move to a definite location. Gas from a gas source (e.g., air from an external air source and/or pump) can then be injected (FIG. 3B, lower arrow) to split a microdroplet of length "L". The volume of the microdroplet split-off (60) is predetermined and depends on the length "L" and the channel cross-section. To prevent the pressure of the gas (e.g., air) from acting towards the inlet side, the inlet (20) and overflow ports (30) may be blocked or may be loaded with excess water to increase the resistance to flow.

The patterned surfaces may also be used to control the motion of the drop. By placing a hydrophobic gas vent (70) further down the channel, one can stop the liquid microdroplet (60) after moving beyond the vent (70). As the drop (60) passes the vent (70), the air will go out through the vent (70) and will not push the drop further.

One can start moving the drop (60) again by blocking the vent (70). By using a combination of hydrophobic air pressure lines, hydrophobic vents and strategic opening and/or closing of vents, one can move the liquid drop back and forth for mixing or move it to precise locations in a channel network to perform operations such as heating, reaction and/or separations.

Figure 4A:
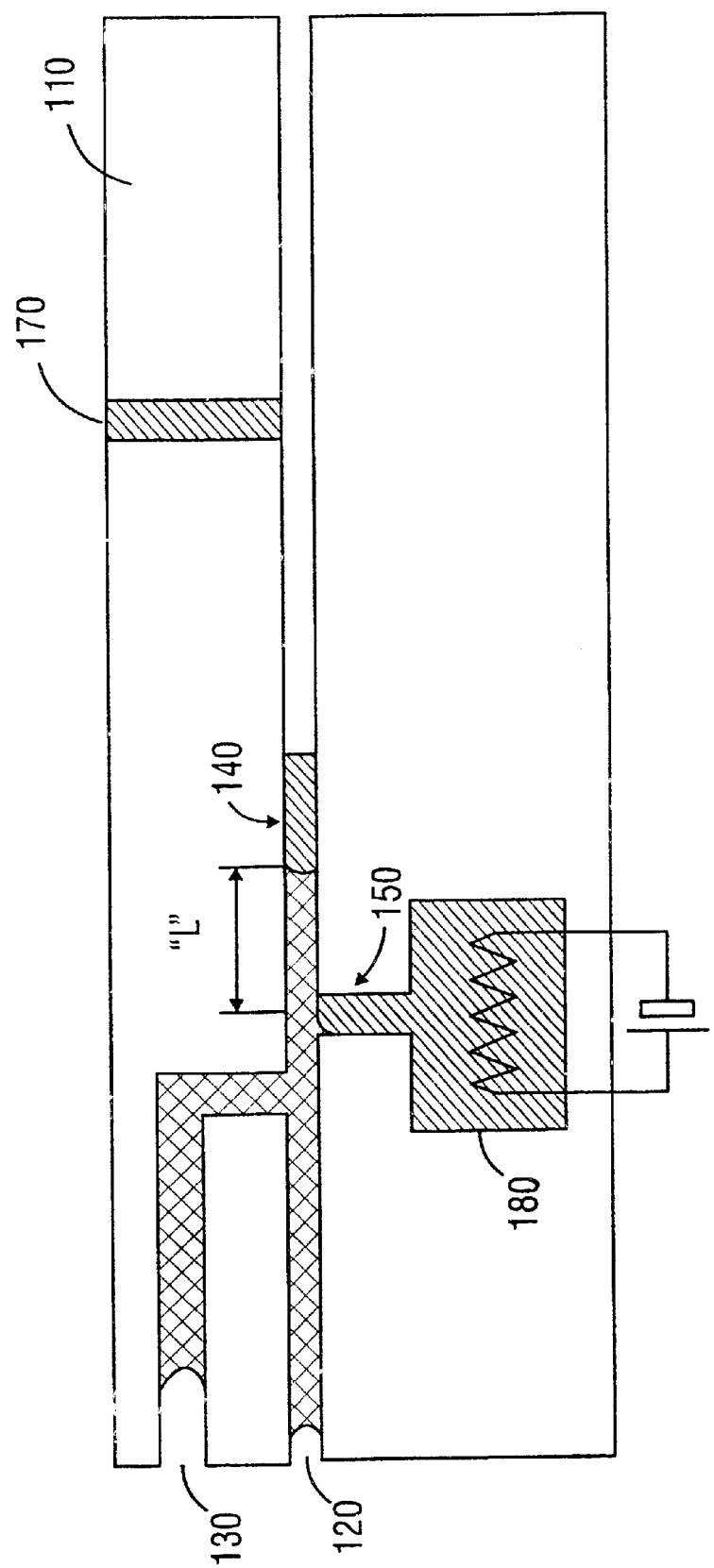
FIG. 4A and FIG. 4B. A schematic of one embodiment of a device of the present invention to split, move and stop microdroplets using internal gas pressure generation.
Figure 4B:
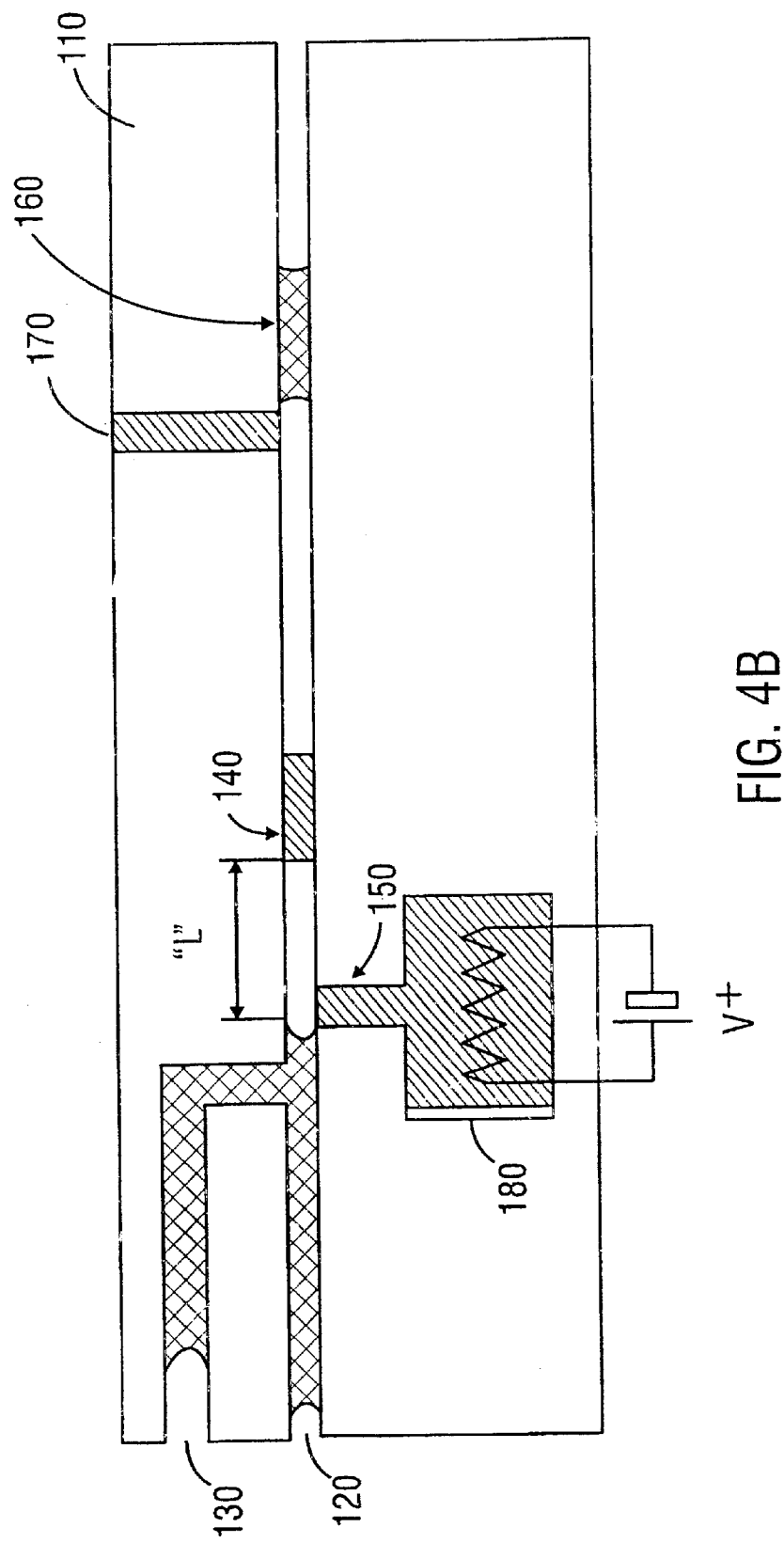

In addition to using external air, one can also use internally generated air pressure to split and move drops. FIG. 4A and FIG. 4B show a schematic of one embodiment of a device (110) of the present invention to split (e.g., define), move and stop microdroplets using internal gas (e.g., air) pressure generation, said device having a plurality of hydrophobic regions (hatched regions). Looking at FIG. 4A, liquid (shown as solid black) placed at the inlet (120) is drawn in by surface forces and stops in the channel at the liquid-abutting hydrophobic region (140), with overflow handled by an overflow channel and overflow outlet (130). In the embodiment shown in FIG. 4A, the front of the liquid moves by (but does not enter) a gas-intake pathway (150) that is in fluidic communication with the channel. By heating air trapped inside chambers (180) that are in fluidic communication with the microdroplet transport channel via the gas-intake pathway (150), an increased pressure may be generated. The magnitude of the pressure increase inside a chamber of volume V is related to the increase in temperature and may be estimated by the Ideal Gas relation.

Increasing the temperature of the gas (e.g., air) will cause the pressure inside the chamber to rise until the pressure is high enough to split off a drop (160) and move it beyond the liquid-abutting hydrophobic region (140). In order to avoid the problem of the expanded air heating up the liquid, the chamber may be placed at a distance from the transport channel. Moreover, having the heaters suspended inside the air chamber or placing them on a thin insulation membrane will not only avoid cross-talk, but will involve a minimal power consumption.

The compositions and methods are suitable for devices having a variety of designs and dimensions, including, but not limited to, devices with chamber volumes from 0.24 mm$^3$ to 0.8 mm$^3$ for channel dimensions of 40 μm by 500 μm. Drop splitting and motion is seen with 1–3 sec using voltages between 4.5 volts to 7.5 volts (the resistance of the heaters varied between 9.5 ohms to 11 ohms). The size of the drop split is between approximately 25 and approximately 50 nanoliters, depending on the value "L" used for the channel design. Keeping the heaters actuated keeps the microdroplet moving almost to the end of the channel (a distance of around 125 mm); the time taken depends on the voltage applied to the heater and the volume of the chamber. Initiation of drop motion is seen sooner for the operation of devices with smaller chambers. While an understanding of precise mechanisms is not needed for the successful practice of the present invention, it is believed that with smaller chamber, the volume is smaller and higher values of pressure are achieved more quickly. The maximum temperatures reached near the heater are approximately 70° C. measured by the RTD.

A. Movement of Discrete MicroDroplets

The present invention contemplates microscale devices, comprising microdroplet transport channels having hydrophilic and hydrophobic regions, reaction chambers, gas-intake pathways and vents, electrophoresis modules, and detectors, including but not limited to radiation detectors. In some embodiments, the devices further comprise air chambers to internally generate air pressure to split and move microdroplets (i.e., "on-chip" pressure generation).

The present invention describes the controlled movement of liquid samples in discrete droplets in silicon. Discrete droplet transport involves a system using enclosed channels or tubes to transport the liquid to the desired locations (FIG. 1-B). Within the channels, discrete liquid reagent microdroplets may be injected, measured, and moved between the biochemical analysis components. Discrete droplet movement has three advantages. First, each sample droplet is separated from all others so that the risk of contamination is reduced. Second, in a uniform channel, the volume of each sample may be determined by merely measuring the droplet length. Third, the motion of these droplets may be accomplished with heating (i.e., using internal forces and no moving parts). Movement is performed using thermal gradients to change the interfacial tension at the front or back of the droplets and, thus, generate pressure differences across the droplet. For example, a droplet in a hydrophilic channel may be propelled forward by heating the back interface. The local increase in temperature reduces the surface tension on the back surface of the droplet and, therefore, decreases the interfacial pressure difference. The decreased pressure difference corresponds to an increase in the local internal pressure on that end of the droplet ($P_1$ increases). The two droplet interfaces are no longer in equilibrium, with $P_1$ greater than $P_2$, and the pressure difference propels the droplet forward.

That is to say, forward motion may be maintained by continuing to heat the droplet at the rear surface with successive heaters along the channel, while heating the front surface may be used to reverse the motion of the droplet. Applying a voltage to the wire beneath the channel generates heat under the edge of the droplet. Heating the left interface increases the internal pressure on that end of the droplet and forces the entire droplet to the right. The pressure on the interior of the droplet may be calculated knowing the atmospheric pressure, $P_{atm}$, surface tension, $\sigma$, and the dimensions of the channel. For a circular cross-section, the interior pressure, $P_i$, is given by $P_i = P_{atm} (4\sigma \cos \theta)/d$ where d is the diameter of the channel and $\theta$ is the contact angle. Since $\sigma$ is a function of temperature ($\sigma = \sigma_o(1-bT)$ where $\sigma_o$ and b are positive constants and T is the temperature), increasing the temperature on the left end of the droplet decreases the surface tension and, therefore, increases the internal pressure on that end. The pressure difference between the two ends then pushes the droplet towards the direction of lower pressure (i.e., towards the right). The aqueous droplet shown is in a hydrophilic channel ($0<\theta<90$); for a hydrophobic channel ($90<\theta<180$), heating the right edge would make the droplet move to the right.

Contact angle hysteresis (the contact angle on the advancing edge of the droplet is larger than the contact angle on the retreating edge) requires a minimum temperature difference before movement will occur. The velocity of the droplet after motion begins may be approximated using the equation $v = AEPd^2/32 \mu L$ where AEP is the pressure difference, $\mu$ is the viscosity of the solution, and L is the length of the droplet. The present invention contemplates temperature differences of greater than 30° C. to create movement. Studies using temperature sensors arrayed along the entire channel indicate that a differential of approximately 40° C. across the droplet is sufficient to provide motion. In these studies, the channel cross-section was 20/$\mu$m×500/$\mu$m, and the volume of each these droplets may be calculated from their lengths and is approximately 100 nanoliters for a 1 cm long droplet.

B. Integrated Fluid Handling System

Although there are many designs currently available for liquid handling in micromachined devices, a preferred method uses individual drops propelled by induced gradients in surface tension. The principle behind the technique is to inject the samples into the device as discrete drops. These drops, once inside the channels, may be propelled by changing the forces on the two drop surfaces. For instance, if the drops are in a hydrophilic channel (glass), the interfacial tension acts outward from both ends. Since the surface tension of water decreases with increasing temperature, heating the left side of the drop causes the drop to be propelled towards the right. Splitting, merging, and mixing of such drops may also be accomplished by careful control of drop location in micromachined channels.

In certain embodiments, the channels contain approximately 30 heaters and 10 temperature sensors along the length of the channels. Location sensors can sense the location, length, and, therefore, the volume of the drop. The base material of the chip is silicon with silicon oxide and nitride layers used for insulation. The resistive heaters in the channel may be made from a variety of materials including platinum, aluminum, and doped polysilicon; in one aspect the chip has gold heaters. These resistive heaters are inlaid into the insulating oxide to provide a smooth (<1 $\mu$m) surface for the upper insulating layer: failure to make the upper surface smooth can result in layer instabilities and device failure during heating in an aqueous environment. Silicon or glass channels may be attached to the substrate with a variety of adhesive techniques. Anodic, UV cure cement, and polyimide bonding have been used in the invention, though other methods may be used, and are known to those of skill in the art.

Drop motion was induced by changes in the surface tension in a glass channel glued to a silicon substrate using UV-cure cement. Note that the surface conditions, solution conditions, and channel geometry, all affect the motion of the drop. Careful attention must be paid to both the construction procedure and the surface preparation procedure or drop motion will not occur. By being able to move drops in this manner, the mixing of two drops (for sample injection) or the splitting of one drop into two (for post reaction treatment) may be accomplished.

C. Characteristics of Micro-Scale Fluids

In miniaturization of a DNA processing system, most components may be designed similar to their benchtop equivalents. Fabrication at the micron level may then be accomplished using known silicon characteristics. Some specific components are easily miniaturized. For instance, a heating element on a silicon wafer will, for most applications, be able to heat a sample much more rapidly than a larger scale heater. This increase in efficiency is due to a decrease in the distance over which thermal energy must travel and to the reduced mass of the sample being heated.

In contrast to the heating of samples, the movement of samples is more complicated. The diameter of the "tubing" through which samples will flow in the proposed system may be reduced to a channel width as small as 10 $\mu$m. This extremely small diameter will change the typical characteristics of the fluid flow. Methods to move liquids become much more difficult in the nanoliter volume range. The Reynold's number (Re) of a liquid system is an indication of the ease with which a liquid will move, and is defined as Equation 1:

$$Re = (v)(d)(r/\mu) \quad (1)$$

where v is the velocity, d is the diameter of the tubing, r is the density of the solution, and $\mu$ is its viscosity. Using the Reynold's number, comparing a 1 cm diameter tube to a 10 $\mu$m diameter channel would result in a Re decrease from about 100 to $10^{-2}$ (for water moving with a velocity of 1 cm/s).

One method of coping with this new flow regime (very low Re) would be to use higher pressure pumps. High pressure liquid chromatography (HPLC) system (d~10 μm) typically run at thousands of pounds per square inch (PSI) pressure, while standard liquid chromatography systems (d~100 μm) can operate with only several PSI. In the silicon wafer system, a pump-based propulsion mechanism may be fabricated by designing an "in-chip" peristaltic pump (Folta et al., 1992). This micropump design consists of a heating element within a thermopneumatic chamber. The thermopneumatic chamber, when heated, causes a membrane along the flow channel to "bulge". Peristaltic pumping occurs by "bulging" of a set of thermopneumatic actuators in series (Van Lintel, 1988; Pohl, 1978). Unfortunately, these pumps must generate a relatively high pressure to move the liquids through micrometer-sized tubing.

Another method for moving small volumes of liquid is to use gradients in surface tension (Edwards et al., 1991). If a thin capillary, tube is inserted into water, the liquid in the capillary, will rise a centimeter or so above the surface of the surrounding water. This rise is due to the force of surface tension acting on the meniscus as defined by Equation 2:

$$F = (\pi)(d)(\delta)(\cos \theta) \quad (2)$$

where d is the inside diameter of the tube, δ is the surface tension (force/length) and θ is the contact angle (Osipow, 1962). If a smaller diameter capillary is used, the decrease in force is proportional to d but the decrease in weight of water per unit height in the capillary decreases by $d^2$. Therefore, for very large diameter tubes, the forces of surface tension can usually be neglected due to the large mass of fluid. However, for small tubes, pores, or channels, the force of surface tension may be great compared to the mass of liquid being moved. This "wicking" of liquid is a common occurrence and may be observed when a porous solid is brought in contact with a solution (i.e., paper towel and water).

By controlling the magnitude and direction of the surface forces, the movement of small sample volumes in the interior of capillary tubes may be controlled. Several researchers have described moving small drops through silicon channels using this principle (Beni and Tenan, 1981; Matsumoto and Colgate, 1990; Fuhr et al., 1992). The technique may be best understood by examining the liquid drop contained in a glass capillary. For glass, θ=0, consequently, the force due to surface tension is pulling the drop both to the right and to the left, and is perfectly balanced. If the surface tension on the left side of the drop is decreased or the surface tension on the left side is increased, the drop will be pulled to the right. Movement to the left may be accomplished in a similar fashion (decreasing the surface tension on the left or increasing the surface tension on the right). Most previous work has changed the surface tension force by altering the channel wall hydrophobicity, and consequently, the contact angle θ.

Alternatively, the surface force may be altered through changes in the liquid surface. It is known that the surface tension of liquids is a strong function of both temperature and surface electrical charge (Osipow, 1962). Matsumoto and colleagues used electrostatic control to develop a surface tension driven micropump (Beni and Tenan, 1981; Matsumoto and Colgate, 1990). Because of the possibility of charge attraction with the DNA molecules in solution, temperature control may be a preferred choice for changing liquid surface tension in the invention. For most liquids, surface tension decreases nearly linearly with increased temperature.

Modeling this dependence may be accomplished using the linear empirical expression. Equation 3:

$$\sigma = \sigma_o(1 - bT) \quad (3)$$

where $\sigma_o$ and b are constants (Beni and Tenan, 1981; Matsumoto and Colgate, 1990). This expression means that increases in temperature result in linear decreases in surface tension. An empirical model was obtained by a linear fit of $\sigma_o$ versus temperature for pure water. The change in surface tension with temperature for pure water is approximately −0.16 dyne/cm (Probstein, 1989) and remains nearly constant over all temperatures for liquid water. It is the magnitude of this change that can serve as the driving force for fluid movement; therefore, knowledge of this parameters magnitude is necessary for predictions of liquid velocities in a capillary system.

D. Micro-Scale Fluid/Solute Parameters

As demonstrated in Equation 4, the velocity profile for fluid motion in a capillary tube depends upon several characteristics of the liquid and its interface with the flow chamber. These include: Δσ, the surface tension difference between the drop ends, d, the capillary diameter, μ, the liquid viscosity, and L the drop length.

$$v_{ave} = (\Delta\sigma)(d)/(8)(\mu)(L) \quad (4)$$

For example, the liquid viscosity, the surface tension difference between the ends of the drop, and the contact angle between the liquid and the flow chamber all influence the magnitude of fluid motion. However, the flow chamber dimensions and geometry affect the shape of the velocity profile of the liquid.

E. Fluid Viscosity

Fluid rheology is the study of how a fluid reacts to a stress (force/area). For instance, a common class of fluids, termed Newtonian fluids, exhibit a regular response to a fluid stress. The behavior of a Newtonian fluid may be expressed in terms of its constitutive equation, which states that the shear stress (force/area) is proportional to the local velocity gradient (Bird et al., 1960):

$$\text{Shear Stress} = (\text{viscosity})(\text{velocity gradient}) \quad (5)$$

where the constant of proportionality, the viscosity of the fluid, is an indication of the resistance to flow.

The dilute aqueous DNA solutions are stored in a Tris-HCl (10 mM), EDTA (1 mM) buffer solution. Although the DNA concentration is presumably too low to affect the physical behavior of the macroscopic fluid, the Newtonian behavior of the water-based solvent was checked. Viscosity measurements, as a function of shear rate, were taken for pure Tris-HCl/EDTA buffer in addition to 1, 50, and 105 microgram/ml samples of DNA solution. The results indicate Newtonian behavior for all three DNA concentrations and for the Tris-HCl/EDTA buffer. As expected, the viscosities of four samples tested were Newtonian, and had viscosities very close to that for water at 25° C. (i.e., 1cP).

F. Surface Characteristics

The contact angle (force/contact length) between a fluid and its solid surface is an extremely important parameter in surface tension driven flow. The magnitude of this force is directly related to the cosine of the contact angle between the liquid and the solid flow chamber. To maximize this force, a perfectly hydrophilic (contact angle of 0°, cos 0°=13 or perfectly hydrophobic (contact angle of 180°, cos 180°=−1) surface is preferred. For example, clean glass surfaces are extremely hydrophilic and form a 0° contact angle with pure water producing the maximum surface tension. Surface treatments of glass can produce hydrophobic surfaces. Two hydrophobic glass surface treatment processes have been examined. First, a silane treatment was followed by addition of a long chain aldehyde (decyl aldehyde). In the second treatment, a commercial brand Rain-X used. Interestingly, the Rain-X treatment was the easiest to apply and produced a more hydrophobic surface than the silane treatment. However, the Rain-X contact angle was still much less than optimal 180° making it a less than ideal surface for surface tension driven flow.

G. Surface Tension

From equation 4, the change in surface tension can serve as the driving force for fluid motion. One embodiment of the invention is described as a micromechanical integrated DNA analysis technology, or MIDAT. In the MIDAT system a temperature difference between the ends of the drop will be used to produce a surface tension difference. For pure water, the change in surface tension with temperature is −0.15 dyn/cm-° C. (Probstein, 1989) and is constant over the entire liquid range of water (Osipow, 1962). Because the DNA solutions being used are very dilute, the surface tension values are expected to be identical to water.

Using the Krus Interfacial Tensiometer K8, the surface tension of both pure water and buffer solution was measured at several temperatures between 15° C. and 55° C. As expected, the buffer and the water solutions exhibit nearly identical slopes. Also, the surface tensions of DNA solutions at several concentrations between 0 and 120 ug/ml were measured. The DNA concentrations were chosen to reflect a range relevant to standard PCR™ reaction conditions (1 µg/ml, 50 µg/ml and 105 µg/ml). There is little to no change in surface tension with varying DNA concentrations at 25° C. These values, ranging from 70–71 dyn/cm, are very close to those described for pure water at 25° C. (72 dyn/cm).

H. Capillary Drop Movement

As an initial demonstration of surface tension driven flow, a small volume of water was moved in a 0.5 mm inside diameter glass capillary. This was accomplished by heating one of the liquid to air interfaces on the drop, thereby imbalancing the surface tension present in the two surfaces of the drop. The 1.5 centimeter long drop was moved approximately 3 cm forward and back using a hot water spray (80° C.) as a heating system. The spray was washed over the glass capillary near the back end of the drop, and followed the drop as it moved. A rough estimate of the velocity of the drop may be calculated from the timed video images. The drop is moving at approximately 0.5 cm/sec, which is of the same order of magnitude as the theoretical velocity prediction, as calculated from Equation 4.

I. Silicon Microfabrication and Integrated Systems.

FIG. 2B shows a physical layout of a constructed chip. It consists of a two wafer bonded structure. One of the wafers is made of silicon and the other is glass. In the glass wafer, two levels of thin-film aluminum are patterned to make electrodes, interconnects, and heaters for the driven mechanisms. On the silicon wafer, the chip is patterned with microchannels and sample inlets and outlets. The two wafers are bonded together to complete the system. The sample is moved inside the channel using a linear array of electrical devices.

Three propulsion mechanisms are contemplated other than the thermal surface tension method for fluid propulsion chips. Microchannels with electrowetting (Beni and Tenan, 1981; Matsumoto and Colgate, 1990; Washizu, 1992), dielectrophoretic, and thermal gradient (Van Lintel, 1988; Pohl, 1978) drives have been fabricated. Briefly, electrowetting propulsion relies on charge-induced change in the hydrophobicity (wetting) characteristics of the channel wall. Induction of a current along the channel makes the wall more hydrophilic, drawing the liquid drop toward the activated electrode. Dielectrophoresis utilizes the difference in dielectric constant between water and air. A liquid drop will be preferentially draw in between the plates of a charged capacitor. Each chip is designed to move samples in the 5–50 nL range.

Twenty-seven devices were fabricated from a single 100 mm diameter wafer. The chips are cut out of the wafer and bonded to a printed circuit (PC) board. The setup is constructed to control the signals to each microchannel heater or electrode using a computer for sample droplet formation, separation, and movement control. The complete fabrication process requires 5 lithographic steps and was completed in one week. Microchannels with thicknesses of 20, 50, 100, and 200 µm deep and 500–1000 µm width were patterned. Each of these was fabricated with 20, 50, or 150 electrodes along the microchannel length.

In determining whether a drop will move due to surface tension gradients, the two key parameters are the magnitude of the surface tension ($\sigma$) and the contact angle ($\theta$). For channels in silicon wafers, the surface is easily oxidized, producing a glass-like surface whose contact angle is approximately zero. This implies that the surface is hydrophilic and the liquid will "wet" the walls of the channel. For a drop in this channel, a force balance on a horizontally oriented drop gives $$(\pi)(d)(\sigma_{left}) = (\pi)(d)(\sigma)_{right} \tag{6}$$

from equation 2. Since the surface tension is constant for a liquid at constant temperature, the forces on each side of the drop are identical, thus the drop remains motionless.

Knowing that surface tension is a function of temperature, the surface tension on one side of the drop may be selectively changed. The surface tension of water decreases as the temperature at the liquid-solid interface increases. Therefore, using a microheater located slightly beneath the surface of the channel, the surface tension on one side of the drop may be reduced while keeping the other side constant. Using the heater in combination with a thermocouple (or other thermosensor), the temperature, and therefore the surface tension, at that edge may be accurately controlled. The unequal heating will accelerate the drop away from the heat source. Sensors fabricated beneath the channel may be used to locate the edge of the drop. (Dielectric sensors may be used for this application, as the dielectric constant of water is different from that of air.) By sensing this movement and turning on sequential heating elements at the rear edge of the moving drop, the drop may be propelled down the flow channel in a "bucket brigade" fashion. Sequence control of the heater activation may be performed by quadrature electrical signals.

The velocity at which the drop will move may be determined by balancing the force generated by the surface tension gradient with the drag caused by the fluid flowing through the channel. The average steady-state velocity for pressure-driven flow in a capillary tube, termed Poiseuille flow, is given as equation 7:

$$v_{ave} = [(\Delta P)(d^2)]/[(32)(\mu)(L)] \tag{7}$$

where $\Delta P$ is the pressure difference between the drop ends, d is the capillary diameter, $\mu$ is the liquid viscosity and L is the drop length (Bird et al., 1960). The pressure difference is a result of the curvature at the interface. Use of Young- Laplace equation relating the pressure difference across a curved interface (Probstein, 1989), such as in a hydrophilic capillary system, results in Equation 4 for calculating the average steady-state velocity for surface tension driven flow:

$$v_{ave} = [(\Delta\sigma)(d)]/[(8)(\mu)(L)] \tag{4}$$

where $\Delta\sigma$ is the difference in surface tension between the ends of the drop. Thus for only small temperature differences across the drop (on the order of 10° C.) velocities on the order of 1 cm/s may be obtained. This velocity is more than sufficient for transporting liquid drops in MIDAT and other chip based systems.

It should be noted that other methods also exist for moving a drop by changes in surface tension. The drop may be moved by changing the hydrophobicity of the channel surface (electrowetting). The surface may be made hydrophobic by a variety of chemical surface treatments. Imparting an electrostatic charge to the channel wall surface at the right edge of the drop, and thereby decreasing the contact angle will have the same effect as heating it: the drop will move to the right. These methods are particularly attractive as they are not greatly effected by the low Reynold's numbers associated with moving small liquid volumes.

J. MIDAT Channel Injection

Accurate and reproducible injection of a small liquid volume into micromachined channels may be accomplished using these principles. At the sample injection port, the channel immediately adjacent to the input reservoir contains a section that is hydrophobic. This portion of the channel contains a series of electrodes that can change the channel hydrophobicity (electrowetting).

A drop of solution is placed on the hydrophilic input reservoir to form a sessile drop. The reservoir is connected to the entrance of a microchannel that delivers the sample into the MIDAT device. A portion of the channel is then made hydrophilic by charging a set of electrodes. Once the required amount of liquid is drawn into the device, the region near the junction of the reservoir and the channel is made locally hydrophobic by turning off the most proximal electrode. Alternatively, a brief burst of heating at the junction could vaporize a small quantity of the sample and break the continuity of the drop. In either configuration, no further in-flow of liquid occurs. The drop is then moved forward by electrowetting or thermal surface tension effects, as discussed previously. Replacement air is drawn in through a small hydrophobic-coated channel. The volume of the drop is fixed by the cross-sectional area of the channel and the distance between cleavage point and the leading drop edge. Sample volumes as low as $10^{-12}$ liters may be manipulated by this system.

During the movement of solutions, the biological activity of the samples must be preserved. Since the channel may be designed to almost any dimension, the surface area/volume ratio may be kept low to avoid surface denaturation of reaction mixture protein components (i.e., DNA polymerase). Adsorption of solutes onto the surface of the channels must be minimized and may be controlled by proper treatment of the channel with various dopants. Conversely, the desorption of silicon dopants into the reaction solutions must be carefully monitored, as these may affect biochemical reactions.

When it is necessary to move the fluid within the channels or chambers of the device, pressure (e.g., air pressure) may be applied to an opening in the channel or chamber (e.g., the inlet port). When pressure is used to move the liquid, there is preferably a second opening or exit port which may be used to apply pressure in the opposite direction or to remove the liquid from the device. Alternatively, the fluid may be moved within the channel using a thermocapillary pump as described by Burns, et al. (1996). The thermocapillary pump has the advantage of providing a self-contained miniaturized device in which movement of discrete aliquots within the channels requires no moving parts or valves.

IV. FLOW CONTROL WITH SEALED VALVES

The present invention contemplates the use of sealed valves to control fluid flow. While the present invention is not limited to a particular sealing method, in one embodiment, an actuating force pushes a diaphragm against a valve seat to restrict fluid flow and the diaphragm is then sealed to the valve seat. In such an embodiment, the solder pads are associated with a heating element that can melt the solder. This liquefied solder flows over areas of the valve seat and diaphragm to cover contamination, cracks and crooks between the diaphragm and valve seat. With the actuating force still holding the diaphragm and valve-seat together, the heating element is turned off to allow the solder to cool and re-solidify. Upon solidification, the actuating force may be released and the valve is sealed. To open the valve again, the solder may be liquefied without applying an actuation force.

In certain aspects of the invention "diaphragm" may refer to an element capable of being manipulated such that it can at least partially block the passage of fluid in a channel in one position (extended) and permit the flow of fluid in a channel in another position. An "actuating force" is a force that is capable of extending a diaphragm. A "valve seat" is an element designed to accept a portion of the diaphragm when extended. A "movement means" is a means capable of moving liquefied meltable material (e.g., force air, magnetic field, etc.).

In a preferred embodiment, the valve is designed such that solder pads are placed on the diaphragm or valve seat. While the present invention is not limited to a precise method of placing these solder pads, it is specifically contemplated that they may be electroplated.

V. MIXING BIOLOGICAL SAMPLES IN REACTIONS

Droplet motion (described generally above) is contemplated as one step in a pathway. The other steps typically involve sample mixing and a controlled reaction. For example, the integral heaters arrayed along the entire surface of the channel used for droplet motion also allow for a region of a channel to be used as a thermal reaction chamber. For sample mixing prior to the reaction, a Y-channel device is one embodiment of the invention. In such a device, a first droplet containing a first sample (e.g., nucleic acid) is moved along one channel of the Y-channel device, and a second droplet containing a second sample (e.g., a restriction digest enzyme in digestion buffer) is moved along the other channel of the Y-channel device.

Following sample merging there is the concern that the combined samples have not been properly mixed. That is to say, if two similar microdroplets enter the single channel in laminar flow at the same flow rate, they will form an axially uniform droplet but will not be mixed width-wise. Width-mixing may be accomplished in a number of ways.

First, there is diffusion, although, for large DNA molecules, the characteristic time for this mixing could be on the order of several hours or more. Circulation patterns generated inside the droplets during movement and heating significantly reduce this time. In this regard, the present invention contemplates maintaining the mixture as a heated mixture (e.g., maintaining the temperature at 65° C. for 10 min) using the integral heaters and temperature sensors.

Second, the present invention contemplates mixing by reversing the flow direction of the mixture over a relatively short distance in the channel. While a variety of reverse flow approaches are possible, one or two direction changes over a distance comprising approximately two droplet lengths has been found to be adequate.

Finally, there is the mixing approach wherein the mixture is moved against or over physical obstacles. For example, the mixture may be either "crashed" back against merge point of the Y-channel or simply moved over deliberate imperfections in the channel (i.e., "roller coaster" mixing).

Successful mixing, of course, may be confirmed by characterization of the product(s) from the reaction. Where product is detected, mixing has been at least partially successful. The present invention contemplates, in one embodiment, using electrophoresis to confirm product formation.

A restriction digest was performed by mixing a DNA sample with an enzyme solution and heating the resulting mixture. The solutions were injected into the ends of the y-channel (simple capillary action drew the samples into the channels). The drops were then moved using the embedded heaters and, once the combined drop was in the single channel, it was heated to a constant temperature. Comparison of the results of this digestion with that performed on commercial thermocyclers indicated little difference.

A. Biocompatibility

A 5 mm×5 mm heater surface for is used as a polymerase chain reaction thermocycler. The cross-shaped loop that divides the region into four heating zones is an RTD (resistive temperature detector). The construction of this chamber is identical to the y-channel heaters described earlier. In fact, the chips are processed on the same wafers. Reactions may be carried out on this surface using either walled polymer vessels for large-volume reactions or etched caps for small-volume (~0.5 $\mu$l) reactions.

PCR™ was run on this chip. The reaction was carried out on the surface of this chip using a polypropylene ring cemented to the chip as the vessel walls. 20 gm of reaction mix was covered with oil to prevent evaporation and the solution was cycled through 94° C., 55° C., and 72° C. using a digital controller (National Instruments LabView, programmed VI, Macintosh Quadra 950 computer). Using such a controller based in LabView allows change in the function and design of the controller without the expense of circuit construction. As the electrophoresis gel indicates, the oxide surface of the chip and the heaters did not damage the enzyme or inhibit the reaction; the chip results appear identical to the control run on a commercial thermocycler. Extensive biocompatibility tests indicate that the results of the reaction are very sensitive to controller settings and to the materials used for construction (Burns, 1994).

B. Reaction Parameters

Solutions containing the DNA samples and solutions containing the reagents for the reaction must both be added to the MIDAT unit, thoroughly mixed, and reacted at the proper temperature. The mixing of solutes at very small length scales is both simple and complex. The simplicity arises because the radial distance that the solutes must diffuse is relatively small and, therefore, any radial mixing will occur quite rapidly. For instance, in a 1 $\mu$m channel, the characteristic time for diffusion a typical solute (D=$10^{-5}$ cm$^2$/s) is approximately (Probstein, 1989):

$$t=L^2/D=(10^{-4} \text{ cm})^2/(10^{-5} \text{ cm}^2/\text{s}) \approx 1 \text{ ms} \qquad (8)$$

Even for larger solutes with diffusion coefficients of $10^{-6}$ to $10^{-8}$ cm$^2$/s, the mixing time is under 1 s.

The complexity arises because the mixing lengthwise in a channel of length 1 cm or longer is not rapid (t≈several days). Care must be taken to assure that uniform mixing occurs along the length of a drop of solution. This uniform concentration may be assured in several ways. First as two drops are mixed, they will join at the front ends. This joining may be accurately controlled using dielectric sensors and heaters, as discussed before. If the drops are in a hydrophilic channel, each meniscus will naturally join. By controlling the force driving each drop, the liquids may be added at precisely the rate to yield a uniform axial concentration.

In addition to this precise control of the liquid motion, uniform axial concentrations may be assured due to the flow pattern generated within the drop moving in the channel. The liquid near the surface of the channel, due to intermolecular forces, remains motionless while liquid in the center of the drop is moving forward at twice the average velocity of the drop. At the back edge of the drop, this stagnant liquid is "picked off" the walls of the channel by surface tension while at the front of the drop, the liquid is deposited by surface wetting phenomena. In this way, the liquid is constantly circulating from the front of the drop, down the side of the drop, and returning through the center. During this travel, the solutes are rapidly mixing radially with the different velocity streams. The net result is that, as long as the drop travels approximately one or two drop lengths, complete mixing of the drop should occur.

VI. ISOTHERMAL AMPLIFICATION REACTIONS

A. Enzymatic Reactions

The channels of the DNA chip may be constructed in any configuration appropriate for the selected reaction protocol. The complete amplification reaction, including the target and the other components for the amplification reaction, may prepared and mixed outside of the DNA chip. The complete amplification reaction is then placed into the channel of the DNA chip and, if necessary, moved to a region of the channel in contact with a heater element which maintains the desired reaction temperature. Alternatively, the reaction may be performed in a device in which the sample containing the target and the sample containing the enzymes and other components of the amplification reaction are maintained as separate liquid aliquots until the reaction is to be initiated. At that time, the two liquid aliquots may be brought into contact by means of pressure, a thermocapillary pump, other equivalent means, such that they mix and react in a region of the channel which is maintained at the desired reaction temperature by a heater element. In an alternative embodiment, the channels of the DNA chip may be in the form of a "Y" such that a liquid aliquot containing the target placed in one arm of the "Y" is kept separate from the enzymes and amplification reagents in the other arm of the "Y". Using pressure applied to the inlet port of each arm of the "Y" or thermocapillary pumps in contact with each arm, the two liquid aliquots are moved into contact at the junction of the two arms and allowed to mix and react at a selected reaction temperature maintained by the heater element in the region of the channel which forms the stem of the "Y". Other configurations for the channels and device designs which also employ reaction chambers and/or detection areas will be apparent to those skilled in the art and are intended to be included within the scope of the invention. If desired, mixing may be enhanced by moving the liquid aliquot back and forth by alternately applying pressure on each side or alternately heating each side of the aliquot, though other equivalent means may be substituted.

In certain preferred embodiments of the invention, the device for use in the isothermal amplification of a selected nucleic acid further comprises one or more of the reagents for an isothermal nucleic acid amplification reaction. Such reagents may include polymerases, nucleotides, buffers, solvents, nucleases, endonucleases, primers, target nucleic acids including DNA and/or RNA, salts, and other suitable chemical or biological components. In certain preferred aspects, these reagents may be provided in dry or lyophilized form. In other embodiments the reagents may be dissolved in a suitable solvent.

In certain embodiments one or more of the reagents, including nucleotides, buffers, salts, chemicals, solvents, primers, target nucleic acids including DNA and/or RNA, polymerases, endonucleases, nucleases, and chemical or biological components suitable for the isothermal reaction mixture are added to the at least first and/or second microdroplet transport channels separately or in various combinations. In other preferred embodiments of the invention one or more of the nucleotides, buffers, salts, chemicals, solvents, primers, target nucleic acids including DNA and/or RNA, polymerases, endonucleases, nucleases, and chemical or biological components suitable for an isothermal amplification reaction are contained in, in liquid communication with, operably or functionally connected to, and/or provided with the microfabricated substrate. In certain other embodiments one or more or the reagents for an isothermal reaction may be contained in a detachable reservoir that may be contained in or attached to an inlet port, channel, or reservoir so to be in liquid communication with, and/or operably or functionally connected to the microfabricated substrate. In certain preferred embodiments the reagents may be in dry or lyophilized form. In other embodiments the reagents may be dissolved in a suitable solvent.

Any isothermal nucleic acid amplification method may be performed on the DNA chips essentially as described in the art. The lower, constant temperature and complex enzymology of isothermal amplification does not inhibit the reaction in the DNA chip format. That is, it has unexpectedly been found that movement and mixing of the liquid aliquots is not significantly compromised, that the enzymes involved in isothermal amplification are not significantly inhibited, and that the predicted stagnant temperature gradient does not prevent efficient amplification. Thermophilic SDA (tSDA) is a preferred amplification method for application to DNA chips because of its high amplification factors and rapid results. Amplification reactions are generally performed in the microfabricated device in a volume of about 0.6 $\mu$L–3 $\mu$L, but the dimensions of the channels and/or reaction chambers may be altered to accommodate larger or smaller reaction volumes.

Nucleic acid used as a template for amplification is isolated from cells contained in the biological sample, according to standard methodologies (Sambrook et al., 1989). The nucleic acid may be genomic DNA or fractionated or whole cell RNA. Where RNA is used, it may be desired to convert the RNA to a complementary DNA. In one embodiment, the RNA is whole cell RNA and is used directly as the template for amplification.

Pairs of primers that selectively hybridize to nucleic acids corresponding to an isolated target sequence for amplification are contacted with the isolated nucleic acid under conditions that permit selective hybridization. The term "primer", as defined herein, is meant to encompass any nucleic acid that is capable of priming the synthesis of a nascent nucleic acid in a template-dependent process. Typically, primers are oligonucleotides from ten to twenty base pairs in length, but longer sequences can be employed. Primers may be provided in double-stranded or single-stranded form, although the single-stranded form is preferred.

Once hybridized, the nucleic acid:primer complex is contacted with one or more enzymes that facilitate template-dependent nucleic acid synthesis. Multiple rounds of amplification, also referred to as "cycles," are conducted until a sufficient amount of amplification product is produced.

Next, the amplification product is detected. In certain applications, the detection may be performed by visual means. Alternatively, the detection may involve indirect identification of the product via chemiluminescence, radioactive scintigraphy of incorporated radiolabel or fluorescent label or even via a system using electrical or thermal impulse signals (Affymax technology).

B. Types of Nucleic Acid Amplification

A number of template dependent processes are available to amplify nucleotide sequences present in a given template sample. It is not intended that the present invention be limited by the nature of the reactions carried out in the microscale device. Reactions include, but are not limited to, chemical and biological reactions. Biological reactions include, but are not limited to sequencing, restriction enzyme digests, RFLP, nucleic acid amplification, and gel electrophoresis. It is also not intended that the invention be limited by the particular purpose for carrying out the biological reactions. In one medical diagnostic application, it may be desirable to differentiate between a heterozygotic and homozygotic target and, in the latter case, specifying which homozygote is present. Where a given genetic locus might code for allele A or allele a, the assay allows for the differentiation of an AA from an Aa from an aa pair of alleles. In another medical diagnostic application, it may be desirable to simply detect the presence or absence of specific allelic variants of pathogens in a clinical sample. For example, different species or subspecies of bacteria may have different susceptibilities to antibiotics; rapid identification of the specific species or subspecies present aids diagnosis and allows initiation of appropriate treatment.

Preferred methods are Strand Displacement Amplification (SDA) and thermophilic SDA for carrying out isothermal amplification of nucleic acids which involves multiple rounds of strand displacement and synthesis, i.e., nick translation.

In this method, either before or after the template nucleic acids are denatured, a mixture comprising an excess of all four deoxynucleosidetriphosphates, wherein at least one of which is substituted, a polymerase and an endonuclease are added. (If high temperature is used to denature the nucleic acids, unless thermophilic enzymes are used, it is preferable to add the enzymes after denaturation.) The substituted deoxynucleosidetriphosphate should be modified such that it will inhibit cleavage in the strand containing the substituted deoxynucleotides but will not inhibit cleavage on the other strand. Examples of such substituted deoxynucleosidetriphosphates include 2'deoxyadenosine 5'-O-(1-thiotriphosphate), 5-methyldeoxycytidine 5'-triphosphate, 2'-deoxyuridine 5'-triphosphate and 7-deaza-2'-deoxyguanosine 5'-triphosphate.

The mixture comprising the reaction components for target generation and SDA can optionally include NMP (1-methyl 2 pyrrolidinone), glycerol, polyp(ethylene glycol), dimethyl sulfoxide and/or formamide. The inclusion of such organic solvents is believed to help alleviate background hybridization reactions.

It should be appreciated that the substitution of the deoxynucleotides may be accomplished after incorporation into a strand. For example, a methylase, such as M. Taq I, could be used to add methyl groups to the synthesized strand. The methyl groups when added to the nucleotides are thus substituted and will function in similar manner to the thiosubstituted nucleotides.

It further should be appreciated that if all the nucleotides are substituted, then the polymerase need not lack the 5' forward arrow 3' exonuclease activity. The presence of the substituents throughout the synthesized strand will function to prevent such activity without inactivating the system.

The selection of the endonuclease used in this method should be such that it will cleave a strand at or 3' (or 5') to the recognition sequence. The endonuclease further should be selected so as not to cleave the complementary recognition sequence that will be generated in the target strand by the presence of the polymerase, and further should be selected so as to dissociate from the nicked recognition sequence at a reasonable rate. It need not be thermophilic. Endonucleases, such as HincII, HindII, AvaI, Fnu4HI, Tth111I, and NciI are preferred.

One can envision several alternative nicking enzyme systems in addition to those detailed in this application. For example, it is generally regarded that class IIS restriction endonucleases (e.g., FokI) contain two DNA cleavage centers within a single polypeptide unit. If one of the cleavage centers was inactivated, such as through site directed mutagenesis, the resultant nicking enzyme could be used in an amplification system not requiring modified deoxynucleosidetriphosphates. As an additional example, the restriction enzyme EcoRI has been shown to preferentially cleave one strand in noncanonical recognition sites or when its canonical recognition site is flanked by an oligopurine tract (Thielking et al., 1990; Lesser et al., 1990; Venditti & Wells, 1991). As another example, the restriction enzyme DpnI (available from New England Biolabs, Beverly Mass.) cleaves a recognition site containing me$^6$ dA on both strands. DpnI or an analogous restriction enzyme may be able to nick the methyl containing strand of a hemimethylated recognition site. Such a system would employ SDA primers ($P_1$ and $P_2$) with methylated recognition sequences along with unmodified deoxynucleosidetriphosphates. Alternatively, certain restriction enzymes are known to cleave the nonmethylated strand of a hemimethylated recognition site (e.g., MspI and me$^5$ dC). Such a system would use a methylated deoxynucleosidetriphosphate. Finally, one could use origin of replication proteins to nick one strand of a recognition sequence.

Polymerases useful in this method include those that will initiate 5'-3' polymerization at a nick site. The polymerase should also displace the polymerized strand downstream from the nick, and, importantly, should also lack any 5' forward arrow 3' exonuclease activity. It should be appreciated that a polymerase ordinarily having such exonuclease activity may be deemed to "lack" such activity if that activity is blocked by the addition of a blocking agent.

An additional feature of this method is that it does not require temperature cycling. Many amplification methods require temperature cycling in order to dissociate the target from the synthesized strand. In this method, a single temperature may be employed after denaturation has occurred. The temperature of the reaction should be high enough to set a level of stringency that minimizes non-specific binding but low enough to allow specific hybridization to the target strand. In addition proper temperature should support efficient enzyme activity. From about 37° C. to about 42° C. has been found to be a preferred temperature range.

The SDA reaction initially developed was conducted at a constant temperature between about 37° C. and 42° C. (U.S. Pat. No. 5,455,166, incorporated herein by reference,). This was because the exo $^-$Klenow DNA polymerase and the restriction endo nuclease (e.g., HindII) are mesophilic enzymes which are thermolabile (temperature sensitive) at temperatures above this range. The enzymes which drive the amplification are therefore inactivated as the reaction temperature is increased.

Methods for isothermal Strand Displacement Amplification which may be performed in a higher temperature range than conventional SDA (about 50° C. to 70° C., "thermophilic SDA") were later developed. Thermophilic SDA is described in published European Patent Application No. 0 684 315 and employs thermophilic restriction endonucleases which nick the hemimodified restriction endonuclease recognition/cleavage site at high temperature and thermophilic polymerases which extend from the nick and displacing the downstream strand in the same temperature range. At increased temperature, the amplification reaction has improved specificity and efficiency, reduced nonspecific background amplification, and potentially improved yields of amplification products. In addition, the need to add the enzymes in a separate step after the initial heat denaturation of double stranded targets may be eliminated when enzymes which are stable at the denaturation temperature are used. UDG decontamination of target-specific amplicons in the SDA reaction is also more efficient when the amount of nonspecific background amplicons is reduced.

Another method, called Repair Chain Reaction (RCR), involves annealing several probes throughout a region targeted for amplification, followed by a repair reaction in which only two of the four bases are present. The other two bases can be added as biotinylated derivatives for easy detection. Target specific sequences can also be detected using a cyclic probe reaction (CPR). In CPR, a probe having 3' and 5' sequences of non-specific DNA and a middle sequence of specific RNA is hybridized to DNA that is present in a sample. Upon hybridization, the reaction is treated with RNase H, and the products of the probe identified as distinctive products that are released after digestion. The original template is annealed to another cycling probe and the reaction is repeated.

Qbeta Replicase, described in PCT Application No. PCT/US87/00880, incorporated herein by reference, may also be used as still another amplification method in the present invention. In this method, a replicative sequence of RNA that has a region complementary to that of a target is added to a sample in the presence of an RNA polymerase. The polymerase will copy the replicative sequence that can then be detected.

An isothermal amplification method, in which restriction endonucleases and ligases are used to achieve the amplification of target molecules that contain nucleotide 5'-[alpha-thio]-triphosphates in one strand of a restriction site may also be useful in the amplification of nucleic acids in the present invention.

Yet another amplification method is described in PCT Application No. PCT/US93/07138, which is incorporated herein by reference, may be used in accordance with the present invention. This method of amplification features treating a target sequence with a first oligonucleotide (that has a complexing sequence sufficiently complementary to a 3'-end portion of the target sequence to hybridize therewith (this alone is termed a primer), and that has a sequence 5' to the complexing sequence that includes a sequence which, in double-stranded form, acts as a promoter for an RNA polymerase (this arrangement is termed a promoter-primer), and a second oligonucleotide (which is a primer or promoter-primer that has a complexing sequence sufficiently complementary to the complement of the target sequence to hybridize therewith), under conditions in which an oligonucleotide/target sequence complex may be formed and DNA and RNA synthesis may occur. In this invention, one or both of the first and second oligonucleotides is a mixture of a blocked and an unblocked oligonucleotide sequence (blocked oligonucleotides have a modified 3' end to prevent or reduce the rate and/or extent of primer extension by a DNA polymerase), or a mixture of oligonucleotides with different 3' modifications. Such a mixture significantly enhances the efficiency of the specific amplification reaction compared to use of only blocked or only unblocked oligonucleotides.

The amplification method synthesizes RNA copies of a target sequence by use of a mixture of blocked and unblocked promoter-primers, or promoter-primers with different 3' modifications, consisting essentially of the same nucleic acid sequence in a ratio that provides for lessened non-specific byproducts. The amplification process occurs spontaneously and isothermally under a broad range of conditions.

Still another amplification methods described in GB Application No. 2 202 328, and in PCT Application No. PCT/US89/01025, each of which is incorporated herein by reference in its entirety, may be used in accordance with the present invention. In the former application, "modified" primers are used in a PCR-like, template- and enzyme-dependent synthesis. The primers may be modified by labeling with a capture moiety (e.g., biotin) and/or a detector moiety (e.g., enzyme). In the latter application, an excess of labeled probes are added to a sample. In the presence of the target sequence, the probe binds and is cleaved catalytically. After cleavage, the target sequence is released intact to be bound by excess probe. Cleavage of the labeled probe signals the presence of the target sequence.

Other nucleic acid amplification procedures include transcription-based amplification systems (TAS), including nucleic acid sequence based amplification (NASBA) and 3SR Gingeras et al., PCT Application WO 88/10315, incorporated herein by reference. In NASBA, the nucleic acids can be prepared for amplification by standard phenol/chloroform extraction, heat denaturation of a clinical sample, treatment with lysis buffer and minispin columns for isolation of DNA and RNA or guanidinium chloride extraction of RNA. These amplification techniques involve annealing a primer which has target specific sequences. Following polymerization, DNA/RNA hybrids are digested with RNase H while double stranded DNA molecules are heat denatured again. In either case the single stranded DNA is made fully double stranded by addition of second target specific primer, followed by polymerization. The double-stranded DNA molecules are then multiply transcribed by an RNA polymerase such as T7 or SP6. In an isothermal cyclic reaction, the RNA's are reverse transcribed into single stranded DNA, which is then converted to double stranded DNA, and then transcribed once again with an RNA polymerase such as T7 or SP6. The resulting products, whether truncated or complete, indicate target specific sequences.

Davey et al., EPA No. 329 822 (incorporated herein by reference in its entirety) disclose a nucleic acid amplification process involving cyclically synthesizing single-stranded RNA ("ssRNA"), ssDNA, and double-stranded DNA (dsDNA), which may be used in accordance with the present invention. The ssRNA is a template for a first primer oligonucleotide, which is elongated by reverse transcriptase (RNA-dependent DNA polymerase). The RNA is then removed from the resulting DNA:RNA duplex by the action of ribonuclease H (RNase H, an RNase specific for RNA in duplex with either DNA or RNA). The resultant ssDNA is a template for a second primer, which also includes the sequences of an RNA polymerase promoter (exemplified by T7 RNA polymerase) 5' to its homology to the template. This primer is then extended by DNA polymerase (exemplified by the large "Klenow" fragment of E. coli DNA polymerase I), resulting in a double-stranded DNA ("dsDNA") molecule, having a sequence identical to that of the original RNA between the primers and having additionally, at one end, a promoter sequence. This promoter sequence can be used by the appropriate RNA polymerase to make many RNA copies of the DNA. These copies can then re-enter the cycle leading to very swift amplification. With proper choice of enzymes, this amplification can be done isothermally without addition of enzymes at each cycle. Because of the cyclical nature of this process, the starting sequence can be chosen to be in the form of either DNA or RNA.

Miller et al., PCT Application WO 89/06700 (incorporated herein by reference in its entirety) disclose a nucleic acid sequence amplification scheme based on the hybridization of a promoter/primer sequence to a target single-stranded DNA ("ssDNA") followed by transcription of many RNA copies of the sequence. This scheme is not cyclic, i.e., new templates are not produced from the resultant RNA transcripts. Other amplification methods include "RACE" and "one-sided PCR" (Frohman, 1990 incorporated by reference).

Methods based on ligation of two (or more) oligonucleotides in the presence of nucleic acid having the sequence of the resulting "di-oligonucleotide", thereby amplifying the di-oligonucleotide, may also be used in the amplification step of the present invention.

One of the best known amplification methods is the polymerase chain reaction (referred to as PCR™) which is described in detail in U.S. Pat. Nos. 4,683,195, 4,683,202 and 4,800,159, and each incorporated herein by reference in entirety.

Briefly, in PCR™, two primer sequences are prepared that are complementary to regions on opposite complementary strands of the marker sequence. An excess of deoxynucleoside triphosphates are added to a reaction mixture along with a DNA polymerase, e.g., Taq polymerase. If the marker sequence is present in a sample, the primers will bind to the marker and the polymerase will cause the primers to be extended along the marker sequence by adding on nucleotides. By raising and lowering the temperature of the reaction mixture, the extended primers will dissociate from the marker to form reaction products, excess primers will bind to the marker and to the reaction products and the process is repeated.

A reverse transcriptase PCR amplification procedure may be performed in order to quantify the amount of mRNA amplified. Methods of reverse transcribing RNA into cDNA are well known and described in Sambrook et al., 1989. Alternative methods for reverse transcription utilize thermostable, RNA-dependent DNA polymerases. These methods are described in WO 90/07641, filed Dec. 21, 1990, incorporated herein by reference. Polymerase chain reaction methodologies are well known in the art.

Another method for amplification is the ligase chain reaction ("LCR"), disclosed in EPA No. 320 308, incorporated herein by reference in its entirety. In LCR, two complementary probe pairs are prepared, and in the presence of the target sequence, each pair will bind to opposite complementary strands of the target such that they abut. In the presence of a ligase, the two probe pairs will link to form a single unit. By temperature cycling, as in PCR, bound ligated units dissociate from the target and then serve as "target sequences" for ligation of excess probe pairs. U.S. Pat. No. 4,883,750 describes a method similar to LCR for binding probe pairs to a target sequence.

Following any amplification, it may be desirable to separate the amplification product from the template and the excess primer for the purpose of determining whether specific amplification has occurred. In one embodiment, amplification products are separated by agarose, agarose-acrylamide or polyacrylamide gel electrophoresis using standard methods (Sambrook et al., 1989).

Alternatively, chromatographic techniques may be employed to effect separation. There are many kinds of chromatography which may be used in the present invention: adsorption, partition, ion-exchange and molecular sieve, and many specialized techniques for using them including column, paper, thin-layer and gas chromatography.

Amplification products must be visualized in order to confirm amplification of the marker sequences. One typical visualization method involves staining of a gel with ethidium bromide and visualization under UV light. Alternatively, if the amplification products are integrally labeled with radio- or fluorometrically-labeled nucleotides, the amplification products can then be exposed to x-ray film or visualized under the appropriate stimulating spectra, following separation.

In one embodiment, visualization is achieved indirectly. Following separation of amplification products, a labeled, nucleic acid probe is brought into contact with the amplified marker sequence. The probe preferably is conjugated to a chromophore but may be radiolabeled. In another embodiment, the probe is conjugated to a binding partner, such as an antibody or biotin, and the other member of the binding pair carries a detectable moiety.

In one embodiment, detection is by Southern blotting and hybridization with a labeled probe. The techniques involved in Southern blotting are well known to those of skill in the art and can be found in many standard books on molecular protocols. See Sambrook et al., 1989. Briefly, amplification products are separated by gel electrophoresis. The gel is then contacted with a membrane, such as nitrocellulose, permitting transfer of the nucleic acid and non-covalent binding. Subsequently, the membrane is incubated with a chromophore-conjugated probe that is capable of hybridizing with a target amplification product. Detection is by exposure of the membrane to x-ray film or ion-emitting detection devices.

One example of the foregoing is described in U.S. Pat. No. 5,279,721, incorporated by reference herein, which discloses an apparatus and method for the automated electrophoresis and transfer of nucleic acids. The apparatus permits electrophoresis and blotting without external manipulation of the gel and is ideally suited to carrying out methods according to the present invention.

VII. ANALYSIS AND MANIPULATION OF AMPLIFICATION PRODUCTS

A. Electrophoresis

The biochemical and electrophoretic manipulations for successful DNA sequencing are well characterized, but have not been assembled into a simple automated processing system. The use of silicon photolithographic fabrication techniques allows components to be compatible, readily assembled as a single device, and inexpensive to mass produce.

One type of device contains several components: liquid injection ports, self-pumping channels based upon surface-force gradient phenomena, a thermally isolated amplification chamber, a decision split point, and gel electrophoresis channels. Next to, and underneath, these components are the system detectors and the controlling circuitry. Within this system a sample is injected, moved to a specific location, and the enzymatic sequencing reactions are performed. A portion of the sequencing product is isolated and sent to a preliminary electrophoresis gel for screening. Using the preliminary information, sequence data acquisition may be optimized by dividing the remaining product between electrophoresis gels having different resolution characteristics.

1. Construction of a Miniature Electrophoresis System.

Existing electrophoresis technology is able to size fractionate sequencing reactions 800 basepairs and greater using gels 50–100 $\mu$m thick and 50 cm long. These results are duplicated using micromachined 5–100 $\mu$m channels. Short channels of about 1 cm length will be linear, longer channels of about 5 cm will use folded columns.

The invention will use technology for DNA electrophoresis and construct the system using microfabrication techniques. The existing technology for DNA sequencing has shown that a polyacrylamide gel 400 microns thick and 55 cm long can easily provide single-base resolution of DNA fragments 100–400 base pairs in length when operated in snapshot mode. The invention may duplicate this separation on a micromachined substrate by using a serpentine channel and an etched glass or silicon substrate. However, as has been reported in the literature, separation should be possible on a much smaller gel.

The first step in miniaturizing this technology is to analyze the resolution obtained in a typical gel and determine how the dimensions and operating conditions of a smaller unit would affect the resolution of the migrating bands. A radiograph of a 55 cm long, 400 $\mu$m thick polyacrylamide sequencing gel that was run for 2 h at 2000 V (58 W) using radioactively tagged DNA was used to estimate $\mu$, $\Delta\mu$, and $D_{\mathit{eff}}$. While the smaller DNA fragments have moved to the end of the gel, the 400 bp fragments are only 10 cm down from the sample wells. To the left of this run is a "G" reaction run for 5, 10, 15, 30, 45, and 60 min at the same voltage. The fragments passing the 10 cm point have been resolved. Thus, if a detector had been placed at 10 cm and monitored continuously (finishline mode), all bands would have been resolved. By using a single detector at the end of the gel and monitoring that detector continuously, the invention is able to use a shorter overall gel length. The net voltage that needs to be applied to the gel would be less to give the same electric field strength (i.e., for a 10 cm gel, only 360 V need to be applied to get the same field).

While this qualitative experiment indicates that the peaks should be resolved in only 10 cm for finishline operation, the invention may use the definition of resolution to quantitatively describe the operation for a variety of operating voltages and channel dimensions.

For a finishline run, the time of the run is just the length of the channel divided by the velocity of the slowest DNA fragment: the time, therefore, is $$t = L^2/(\mu_{slow} V) \qquad (9)$$

where L is the channel length, $\mu_{slow}$ is the mobility of the slowest band, and V is the applied voltage. The resolution between bands may be defined as $$R = 2\frac{(z_2 - z_1)}{(w_1 + w_2)} \tag{10}$$

where $z_i$ is the location of the center of each band and $w_i$ is the width of the band (measured at baseline). The width of the peaks may be approximated by $$w_i = (32 D_{\mathit{eff,ave}} t)^{1/2} \tag{11}$$

where $D_{\mathit{eff}}$,ave is the average dispersion coefficient between the two bands. Knowing that the difference in spatial locations $(z_2-z_1)$ is easily calculated from the electrophoretic mobilities, R may be rewritten as $$R = \tfrac{1}{4}\Delta\mu V/L(t/2D_{\mathit{eff,ave}} t)^{1/2} \tag{12}$$

Plugging Equation (9) into Equation (12) obtains $$R = \tfrac{1}{4}(V/(2D_{\mathit{eff,ave}}))^{1/2}\Delta\mu_{slow}/\mu_{slow}^{1/2} \tag{13}$$

where $D_{\mathit{eff}}$,ave is the average dispersion coefficient between the two bands and $\Delta_{slow}$ is the difference in mobility between the slowest and next slowest fragments.

Using a radiograph of a 55 cm long, 400 µm thick polyacrylamide sequencing gel that was run for 2 h at 2000 V (58 W) gel, these equations may calculate whether the 360 volts in the 10 cm gel would be able to obtain 400 bp resolution. The mobility, $\mu_{400}$, is given by $(dL)/(Vt) = 3.1 \times 10^{-5}$ cm$^2$/Vs. Since the 399 and the 400 bp-length fragments are 0.03 cm apart (band 399 and 397 are 0.06 cm apart, therefore 399 and 400 are ≈0.06/2 cm apart), then $\Delta\mu$, is $((\Delta d)L)/(Vt) = 9.2 \times 10^{-8}$ cm$^2$/Vs. $D_{\mathit{eff}}$ is more difficult to obtain. If the plot of the width of a bands vs, $t^{1/2}$, $D_{\mathit{eff,ave}}$ may be found, using equation 11, from the slope of the straight line through the points. This was difficult to do for the 400 bp band but the plot of this information for the 133 bp long fragment may obtain an estimate of $D_{\mathit{eff,ave}} = 7 \times 10^{-8}$ cm$^2$/s. This value is significantly above the molecular diffusion coefficient of DNA in free solution (~$10^{-9}$ cm$^2$/s) and probably represents both the dispersion caused by the gel matrix and the low resolution of the x-ray film (Lang and Coates, 1968). Note that this calculation assumes that the sample was applied in an infinitesimally small sample volume; the zero intercept on the plot indicates that this is essentially true. The microfluidic devices in the MIDAT system may be used to introduce the sample in a similar fashion as what is done on the large scale.

The invention may calculate the resolution that should be obtain based on the above approximate and the 360 V in the 10 cm finishline gel. Using $\Delta\mu = 10^{-7}$ cm$^2$/Vs, $\mu = 10^{-5}$ cm$^2$/Vs, $D_{\mathit{eff,ave}}$ $10^{-8}$ cm$^2$/s (this value was decreased to compensate for the band broadening caused by the film), and Equation 13, R≈1.0. Although an R value of 1 usually defines a adequate separation, peaks can still be resolved at significantly lower R values. This implies that voltages as low as 200 V (R=0.75) may be used and still achieve adequate resolution. These voltages pose little problems in either the glass or silicon devices. Note that, $D_{\mathit{eff}}$ in a variety of different media; $D_{\mathit{eff}}$ should be a function not only of the matrix used but also of the distance traveled.

The length of the channel governs the minimum spatial resolution the detector must possess; this spatial distance would be equal to the separation distance between the two most difficult peaks. Knowing that $\Delta z = \Delta\mu$ V/L t and using Equations 9 gets $$\Delta z = L\Delta\mu_{slow}/\mu_{slow} \tag{14}$$

Using the parameters obtained above, $\Delta z=0.003$ L. Thus if the electrophoresis channel was 10 cm long, the spatial resolution of the detector must be 0.03 cm (the distance actually obtained between the last two peaks).

The thickness of the gel governs both the quantity of DNA in a migrating band and the heat dissipation of the channel. The quantity of the DNA in the band must be matched with the sensitivity of the detector. Based on the fluorescent probes in current sequencing gels, electrophoresis channels 20–100 µm high should not have a problem with sensitivity of the fluorescent detector.

The temperature profile in the gel must remain constant to avoid viscosity/mobility gradients that could distort the bands. For symmetric gels, the temperature rise in the center of the gel may be calculated by solving the heat conduction equation with constant-temperature boundary conditions and a heat generation term. Published solutions are available and are of the form (Geankoplis, 1993)

$$\Delta T = (SH^2)/(2k) \tag{15}$$

where $\Delta T$ is the difference between the surface temperature and the center of the gel, S is the heat generation per volume in the gel, H is the thickness of the gel, and k is the thermal conductivity of the solution. Knowing the resistivity of the solution in the gel ($\rho$), one can obtain an equation for $\Delta T$ in terms of operating variables:

$$\Delta T = \frac{(HV/L)^2}{8k\rho} \tag{16}$$

Assuming a solution resistivity of 500 $\Omega$ cm and thermal conductivity of 0.006 W/cm K, $\Delta T$ for a typical sequencing gel (0.4 mm thick, 55 cm long run at 2000 volts (~50 watts)) is less than 0.1° C. Note that this analysis assumes that the wails of the gels were kept at constant, equal temperatures; microfabricated heaters and temperature sensors can easily accomplish this. Equation 8 can be rearranged to solve for the height of the channel:

$$H \leq 1.5 L/V \tag{17}$$

where V is in volts. Note that this equation was derived for the specific test gel that was used and for a temperature difference of 0.1° C.; the equation would need to be derived for other gel/polymer systems. Note also that, for their test gel, the equation correctly calculates that H≤0.4 mm.

There are a variety of other considerations for scale-down of DNA sequencing systems. For instance, the mobilities and dispersion coefficients may be functions of field intensities or channel wall materials. However, the analysis presented here provides the framework with which to design micromachined systems.

2. Summary of Channel Specifications

The channel specification will use three basic criteria: First, the resolution will be measured and designed to be above 0.8:

$$R = \tfrac{1}{4}(V/(2D_{\mathit{eff,ave}}))^{1/2}\Delta\mu_{slow}/\mu_{slow}^{1/2} \tag{13}$$

Second, the spatial resolution of the detector will be designed to give adequate spatial resolution:

$$\Delta z = L\Delta\mu_{slow}/\mu_{slow} \tag{14}$$

Third, the height of the channel will be small enough to prevent temperature gradients:

$$H \leq 1.5L/V \quad (17)$$

Thus, to sequence a 400 base-pair fragment by standard techniques, a 55 cm channel that was 400 μm high is used. The invention may be able to run the same sample in a 10 run channel that is 100 μm high. Both of these designs may be constructed using silicon microfabrication.

The use of very small diameter capillary systems for electrophoretic separations has been well established since the early 1980's (Jorgenson and Lukacs, 1981; Kuhr, 1990). Capillary electrophoresis has an enormous theoretical resolving power and has been commercially applied to a number of analytical systems (Datta, 1990; Gordon et al., 1988). A variety of liquid capillary formats are available, having glass, fused silica, coated, and rectangular columns. Automated injectors and high sensitivity detectors are also being actively developed. More recently, polyacrylamide gel-filled capillary columns have become available for use with DNA fragment separation (Mathes and Huang, 1992; Swerdlow et al., 1992; Drossman et al., 1990).

Standard liquid capillary electrophoresis has been reported as an integrated silicon chip technology (Manz et al., 1991; Manz et al., 1992; Lammcrink et al., 1993). The channel dimensions of the chip-integrated liquid capillary electrophoresis system were approximately 30 μm wide by 10 μm deep. These columns had very long effective lengths (several cm), and were constructed as spirals on the surface of the silicon chip. Very high voltages were used in the separation, on the order of several kilovolts. As a consequence, breakdown of the silicon substrate was seen as a major obstacle to routine use. As gel columns of the MIDAT may be micromachined channels etched on silicon chips, however, much lower voltages are required for gel electrophoresis (1 to 10 volts/cm). Glass capillary gel electrophoresis has been described with 50 μm to 75 μm inner diameter tubing, and effective column lengths of from 50 cm to a few millimeters (Pentoncy et al., 1992; Heller and Tullis, 1992). Theoretical models of DNA electrophoresis have been useful for estimating the matrix pore structure needed for a particular separation application (Datta, 1990; Gordon et al., 1988).

3. Electrophoretic Separation

Following the amplification reaction, the replicated DNA fragments may be transported to the separation system, again by means of heating-induced surface tension propulsion. In the MIDAT system, the separation may be performed using a chip-integrated capillary gel electrophoresis system. Additionally, the switch to a square channeled capillary obtained from the micromachining process may benefit the separation process. Turner (1993) has cited many reports that square capillaries are advantageous to circular ones due to their higher surface-volume ratio in providing for more effective heat dissipation.

The gel is polymerized inside a channel that is made entirely using thin films. The unpolymerized acrylamide enters the channel from a sessile drop using an injection scheme similar to that described previously. After filling, the acrylamide monomers are polymerized in situ by the addition of catalyst or by photoinduction. Channel walls may need to be chemically treated to alter the wetting properties or surface charge (Kolb and Cerro, 1991).

The sample may be directly moved to the anode chamber. The complex mixture of reagents in the isothermal amplification reaction, including unincorporated labeled nucleotide monomers, may necessitate a pre-electrophoresis separation step. This step may be accomplished by low-molecular weight dialysis. Microporous membranes may be fabricated in silicon (Petersen, 1982), and may provide an on-chip dialysis mechanism.

A low voltage field (1–10 V/cm) is applied to the gel column to induce electrophoretic motion. This field strength will allow fractionation of DNA fragments of the PCR™ size-range in about 10 min on a 1 cm-long column (Pentoncy et al., 1992; Heller and Tullis, 1992). Switched-field electrophoresis schemes may also be used for more rapid DNA fragment discrimination. In order to reduce the area of the separation stage, the column may be folded. Such arrangement is more compact and can increase DNA fragment resolution by several fold.

B. Detection

1. Detector Specifications and Construction

The detection scheme uses previously tested high-sensitivity semiconductor diode detectors placed about 0.5–1 μm beneath the electrophoresis stage. A preferred detection structure has a lightly-doped diffusion diode (Kemmer, 1980; Wouters and van Sprakelaar 1993) suitable for measurements of both β radiation decay from $^{32}$P labeling isotopes and visible-light wavelength photons from fluorescent labels. The detector consists of an n+ diffusion onto a lightly-doped 100 p-type float zone silicon substrate with resistivity of 100 Ω-cm. The n+ diffusion is buried under the electrophoresis stage and separated from it by a thin dielectric layer or layers. Fluorescence-based detection may be performed using these detectors as photodiodes and adding a thin film optical filter layer(s) placed between the gel and detector.

The operation of the diffusion detector is as follows. First a reverse bias is applied between the n+ and the substrate, creating a depletion region. Due to the low doping of the substrate, the depletion region is approximately 8 μm deep for a 10 V bias. When a particle or photon traverses the depleted area, electron hole pairs are generated. Carriers generated in the depletion region are readily swept to the electrodes generating a short current burst. When the mean free path of the impacting particle is greater than the depletion region, additional carriers diffuse through the substrate until they reach the edge of the depletion region where they are collected back over time. Therefore the detector current consists of a sharp peak (corresponding to the charge generated in the depletion region) followed by a long tail caused by the diffusing carriers. Diffusion detectors are highly sensitive to small charge packets, responsive to the initial position of the ionization charge, and easily fabricated in silicon. Approximately 50% of the charge is collected within 1 ns from the decay.

Because of the close proximity to the gel, these detectors can pinpoint the position of a radioactive decay or light emission event within 0.5 μm inside the gel. In simple radiation detection mode, each detector is capable of sensing a single decay of a β particle from a $^{32}$P DNA label yielding an average of 15,000 electrons per event and a charge of 2.5 fC. However, this extremely small charge packet demands the use of low-noise and low-parasitic capacitance instrumentation amplifiers. Therefore, the detectors will have on-wafer low-capacitance buffer amplifiers implemented in NMOS technology. Effective charge gains of 5 V/fC and noise level of 50 electrons are prepared. In existing CCD charge amplifiers, smaller charge packets have been sensed on silicon fabricated devices at noise levels of 10–18 electrons (Hynecek, 1992).

The primary improvements to the existing diode detector involve conversion to a narrow wavelength visible light detector. Since the detector can function as a fluorescence detector as long as the appropriate filters are used, the invention may include the design and construction of optical filter materials directly on the silicon substrate and diffusion diode. The electrophoresis channels are separated from the underlying silicon wafer and electronic components by layers of silicon oxide and silicon nitride (made by low pressure chemical vapor deposition, LPCVD). The same fabrication method may be used for production of optical filters. First, the spectral absorbance characteristics of silicon nitride are well known and vary depending on the stoichiometric ratios of silicon to nitrogen (Philipp, 1993; Macleod, 1986). The LPCVD method allows control of Si:N ratios, and for most ratios, some range of the visible spectrum is completely transmitted. In addition, stoichiometric $SiO_2$ is transparent to visible light and much of the UV-range, while pure crystalline silicon (Si) is opaque. Second, the sequential layering of silicon oxide and silicon nitride layers of approximately one-quarter the passed wavelength (0.25×λ) can produce narrow wavelength interference filters. The invention uses the known optical properties of silicon-based thin film materials to design and construct interference/absorbance filters, including primarily LPCVD deposition of silicon nitride and silicon oxide over the detector. The final filters may require less than 10 μm of material to achieve complete UV blocking.

Spatial resolution is an essential requirement in detectors used for separations. The spatial resolution determines the accuracy in the localization of an emission event within the sieving material. Detector structure design may assist in determining the position of an emission source. Three distinct phenomena affect the detector resolution. First, in order for the position of the impact to faithfully reflect the location of the DNA fragment, the distance between the gel and detector must be small. In the integrated structure, the detector is in direct contact with the gel channel, hence resolution loss through dispersion is minimal. Second, the detector capture width must be small. The diffusion diode detectors have a capture width of 2 μm and are easily formed with lithographic techniques.

Thirdly, to prevent sensing of emissions from adjacent DNA fragments, the detector response must be insensitive to events originating outside its capture width. The use of a guard ring around the sensing electrode (Belcarz et al., 1970) eliminates spurious signals. The ring collects charges generated outside the capture range of interest, preventing them from interacting with the central detector. The resulting structure is a low-noise, low-leakage detector. Further improvements on the localization are accomplished using charge division techniques (Knoll, 1989; Alberi and Radeka, 1976; Gerber et al.; 1977; Belau et al., 1983;). The position of the source of the emission event is calculated from the difference in the two outputs V1 and V2. The respective charges collected on a set of electrodes are used to estimate the centroid of the decay through the resistive network. Localization of the decay event within 0.5 μm may be possible. Other detector structures are based on MOSFET structures since these devices are directly compatible with NMOS process.

2. Implementation of Detection Circuits

The charge collected by the diffusion detector from a β particle or photon yields approximately $10^4$ electrons per event. Semiconductor radiation detectors of this type are typically (Knoll, 1989) connected to electronic amplifiers. The detector is essentially a diode in reverse bias subject to a transient pulse of charge lasting a few nanoseconds. The output of the detector is fed directly to a low noise op-amp (typically a JFET buried channel input device) which integrates the pulse of current and generates a step in the potential at its output. The virtual ground of the op-amp maintains a constant potential difference across the detector; therefore its output is independent of parasitics connected to this node. The parasitic cancellation allows the implementation of most of the circuits off of the device. Any leakage through the diode will induce an offset at the op-amp output. Since the charge packet is very small, the corresponding integrator capacitor should also be small. A 250 fF capacitor yields a change of 10 mV at the integrator output. Hence, it will be desirable to make the resistor as high as possible to minimize the noise of the circuit and to retain the capacitor charge as long as possible (a 10 Ω resistor yields a retention time of 2.5 sec). Any drifts in the leakage current, such as response to a temperature change, will lead to large drifts in the output voltage of the op-amp and may drive the op-amp outside its linear operation regime.

For the diffusion diode detector circuit, the invention uses an on-wafer circuit that eliminates most of these parasitic effects. The circuit consist of a current source depletion load, an enhancement discharge transistor, inverters linked to a non-inverting amplification stage, and a low-pass filter. The circuits are fabricated using a 3 μm NMOS process.

3. DNA Detection

An embodiment of the invention is the DNA sample detector. Two primary detection schemes are contemplated. First, fluorescent DNA labels are commercially available and may be detected using optical p-n photodiodes constructed below the electrophoresis column. The optical transducers are very small with areas on the order of 5 pm. Many detectors may be constructed in a small area, permitting multiple detector sampling of each electrophoresis column, if desired. The signal of each detector may be multiplexed with an on-chip circuit.

The fluorescent tags may be excited by an external laser scanning system or, more simply, a uniform source of light. Special attention is required for wavelength discrimination and detection of the faint fluorescent signals. For ethidium bromide-stained DNA, the excitation wavelength is 302 nm and fluorescent emission is 590 nm. The silicon nitride base of the electrophoresis channel absorbs all wavelengths less than −500 nm; thus blocking the UV radiation and transmitting the fluorescent signal. Alternatively, fluorescent DNA labels are becoming available with a variety of excitation and emission spectra (Middendorf et al., 1992).

A method for detection uses radioactively labeled DNA products. Silicon fabricated radiation detectors have been used since the earlier 1960's (Bertolini, 1968; Deme, 1971; Knoll, 1979), and are extremely sensitive. The basic structure is similar to that of the p-n photodetector. The incoming radiation ionizes the silicon creating free carriers that are collected by the reversed bias diode. The energy needed to create an electron hole pair is about 3 eV. Typical decay energies of β-emitting DNA labeling isotopes ($^{32}P$, $^{33}P$, $^{35}S$) are in the 50 to 500 keV region. These energies can create a collected charge of $10^{13}$ coulombs per event and an easily detectable current of a few microamps. To prevent the collection of radiation-generated carriers from adjacent regions of the chip, a shielding ring is constructed around the n+detector. The radiation detector may prove less expensive than the optical scheme, as radioactive DNA tracers are less expensive than fluorescent labels.

Amplification may be detected either in the DNA chip or after removal of the amplified sample. If the amplified sample is removed for post-amplification detection (either through the inlet port or through a second outlet port), the channels and/or chambers are preferably washed with additional liquid and the wash liquid added to the amplified sample for detection. If amplification is to be detected within the microfabricated device, the liquid may be moved through the channels to a separate area containing reagents for a detection reaction and means for detecting the amplification products (e.g., labeled probes for hybridization detection and means for detecting the hybridized label or microelectrophoresis channels and means for detecting the amplification products by electrophoresis). Alternatively, amplification products may be detected in the same area where the amplification reaction takes place when the detection system is compatible with or a component of the amplification reaction, as discussed below. Amplification products may be detected by hybridization to an assay probe which is typically tagged with a detectable label. The detectable label may be conjugated to the probe after chemical synthesis or it may be incorporated into the probe during chemical synthesis, for example in the form of a label-derivatized nucleotide. Such labels are known in the art and include directly and indirectly detectable labels. Directly detectable labels produce a signal without further chemical reaction and include such labels as fluorochromes, radioisotopes and dyes. Indirectly detectable labels require further chemical reaction or addition of reagents to produce the detectable signal. These include, for example, enzymes such as horseradish peroxidase and alkaline phosphatase, ligands such as biotin which are detected by binding to label-conjugated avidin, and chemiluminescent molecules. The probes may be hybridized to their respective amplification products in solution, on gels, or on solid supports. Following hybridization, the signals from the associated labels are developed, detected and optionally quantitated using methods appropriate for the selected label and hybridization protocol. The amount of signal detected for each amplification product may be used to indicate the relative amount of amplification product present. Ligand labels may also be used on assay probes to facilitate capture of the hybrid on a solid phase (capture probe).

An alternative method for detecting amplification products is by polymerase extension of a primer specifically hybridized to the target sequence. The primer is labeled as described above, for example with a radioisotope, so that the label of the primer is incorporated into the extended reaction product. This method is described by Walker, et al. (1992b) and Walker, et al. (1992a). Another method for detecting amplified target and control sequences is a chemiluminescent method in which amplified products are detected using a biotinylated capture probe and an enzyme-conjugated detector probe as described in U.S. Pat. No. 5,470,723. After hybridization of these two assay probes to different sites in the assay region of the target sequence, the complex is captured on a streptavidin-coated microtiter plate, and the chemiluminescent signal is developed and read in a luminometer.

The foregoing detection methods are generally used for post-amplification detection, either after removing the sample from the microfabricated device or in a separate detection area of the chip containing reagents and detecting means. As another alternative for detection of amplification products, a signal primer (essentially a detector probe which is extended by polymerase, displaced and rendered double-stranded in a target amplification-dependent manner) as described in EP 0 678 582 may be included in the amplification reaction. In this embodiment, labeled secondary amplification products are generated in a target amplification-dependent manner and may be detected as an indication of target amplification in a homogeneous assay format either post-amplification or in real-time (i.e., during amplification). The DNA chip assay formats of the invention are particularly well-suited to real-time homogeneous amplification detection, as the label of the detection system (e.g., a signal primer) may be detected through the glass or silica walls of the channel or reaction chamber as amplification is occurring in the liquid aliquot. When the signal primer is labeled with a fluorescent label, the increase in fluorescence polarization as the signal primer becomes double-stranded may be monitored in this manner, either in real-time or at a selected endpoint in the amplification reaction.

C. Fluidic and Electronic Integration of the Sequencing System

Using the invention's micromachined fluid-handling capabilities, they integrate the template preparation, biochemical reactions, and electrophoresis systems on a single device. Concurrent integration of electronic components (detector, heaters, liquid detectors, and temperature sensors) allows the construction of a self-contained sequencing system. The invention will use sequencing technology in their microfabricated electrophoresis devices. The widths of the channels are (20–100 $\mu$m) are on the same order of those currently being produced commercially and the interior material of the channels is silicon oxide (glass). While most substrates are only 10 cm in diameter (i.e., the largest linear dimension constructed is 10 cm), longer channels may be constructed by using a serpentine channel (Jacobson et al., 1994). Both radiation and fluorescence detectors may be constructed beneath these channels to provide either a snapshot (many detectors beneath the channel or finishline (one detector at the end) mode for running separations. The temperature of the gel may also be measured and controlled to insure that no gradients exist across the gel. These separation systems may be microfabricated in either silicon or glass.

1. Elimination of Sequencing Bottlenecks Using Intelligent Systems

The system of integrated fluid-handling, electrophoresis, detector, and circuitry components allows feedback and decision-making directly within the device. In one embodiment information-based processing is used to reduce both the systemic and random errors for each sequencing sample, and to improve reproducibility, error-detection, length of readable data, and compatibility with existing sequencing protocols.

The invention assembles individual components for DNA sample handling and DNA sequencing into increasingly complex, integrated systems. The incorporation of steps that normally occur in large volumes "on the bench" will reduce the bottlenecks associated with current large-scale DNA sequencing efforts. Since each individual sequencing preparation, reaction, and electrophoresis run has its own set of devices, bottlenecks cannot occur within the integrated system.

D. Chip Multitasking

It is contemplated that using micromachining techniques, reaction and separation units that are impossible or impractical to build by any other techniques are constructed. For instance, an electrophoresis chamber with hundreds of DNA detectors along its length may be constructed for the same cost as constructing a chamber with only one sensor. Also, several hundred of these chambers may be processed on a single wafer with no additional cost (aside from dicing and other post-wafer processing costs). The same technology that makes transistors in integrated circuits so cheap may allow these complicated, integrated systems to be produced for a fraction of what their larger-scale equivalents cost.

1. Fluidic Control and Integration

The controlled movement and mixing of nanoliter drops in micron-scale channels has been demonstrated using a differential-heating propulsion mechanism Control circuitry may maintain uniform biochemical reaction conditions and to reproducibly measure and detect the location of individual drops. The individual micro fluidic components for DNA sequencing may maintain compatibility among the devices. A variety of photofabricated, integrated DNA analysis systems is contemplated.

2. Photolithographic Components as Design Tools

Once a device component has been developed on a computer aided design program, it is replicated across the surface of the wafer as many times as desired. Each additional reiteration of the component or group of components does not cost appreciably more, since the entire wafer is processed uniformly. The machines are reproduced photographically. DNA analysis is a highly repetitive task, requiring many identical devices generating data with very uniform characteristics. Silicon photolithographic fabrication provides multiple identical devices cheaply.

3. Modules for Specific Multi-Step Tasks

To perform a DNA analysis task, the individual components is linked and function as an integrated device. A set of tasks which are often found together in a molecular biology protocol are designed as a functional group or module. The module may be replicated at multiple locations in the larger device, wherever the specific tasks are required. Since each sample has its own set of devices at each step, no time or effort is lost waiting for batch processes to occur, and there are no points where process bottlenecks occur.

4. Incorporation of Earlier Sample Processing Steps in the System

Increasingly complex devices may be assembled from the individual components and basic functional modules. The modules do not perform any template handling, and consequently require well-characterized template as starting material. The entire processing stream may be incorporated onto the device, with all steps included within the silicon-fabricated environment. This embodiment will eliminate process bottlenecks since each sample will have its own dedicated series of instruments.

As an example of an "intelligent" system, the modules take advantage of the ability to hold a sample in reserve, while portion of the sample is being examined. The determination of a DNA template size and quantity prior to more extensive processing is an use of this capability. Size information, for example, can inform the temperature, number of cycles, and electrophoresis conditions of a cycle sequencing run.

A single source DNA is used to supply three sequencing reactions. Template DNA is amplified from the source independently for each sequencing reaction. The template is then divided into two samples and one is assayed for quality and size by gel electrophoresis. The remaining template is then treated to remove unincorporated primers and dNTPs prior to cycle sequencing. The information obtained by analysis of half of the sample is used to determine the reaction parameters of later steps. This figure is presented only as an example: alternative template preparation strategies are contemplated.

5. Reduction of Systemic and Random Error

Once a fundamental design is established in the microfabricated format, it is a minor additional expense to prepare and run additional gels for each synthesis reaction. Rerun gels are, in fact, one of the major custom-handling difficulties of current large sequencing groups. As an embodiment, one design would generate two gel reads for each Sanger reaction. Double gel runs, under different conditions, may be able to resolve bands that migrate anomalously under a single condition. If two parallel gels are run, the output data must then be merged and compared to resolve the differences between gel reads.

A second method to reduce error involves duplicate synthesis reaction conditions. For example, longer gel reads are possible (up to 1000 bp) using a combination of modified dideoxy:deoxy ratios and extended gel electrophoresis lengths. The original template is divided in to two samples, one half receiving standard Sanger reaction mix, the other a modified mix which emphasizes longer read length. Both reactions are then run on sequencing gels, and their output merged. This example describes one possible system developed from individual components: a large number of alternative strategies are contemplated.

The MIDAT system is constructed from a conventional silicon wafer using advanced micromechanical fabrication techniques. In certain embodiments, it is contemplated that silicon wafers are constructed with 100 to 1000 Parallel MIDAT processing units. The multiplex wafer may be capable of simultaneous genotyping an equivalent number of DNA samples, and may provide computer-readable data in less than 3 hours. Miniaturization of DNA analysis results in significant savings in reagents, enzyme, sample handling, and sample processing time.

As a result of the enormously flexible design characteristics of silicon, improved versions may be developed rapidly as the basic biochemical methods advance. Consequently, other methods of nucleic acid amplification and analysis should be compatible with the MIDAT system.

6. Integration of Micromachined Components on a Single Substrate

It is contemplated the invention will comprise hundreds of control and detector connections. In practice, the number of external connections may be limited by the chip size. By integrating the system with on chip electronics, it may be controlled using as little as 5 external leads. One embodiment of the invention is on-chip circuitry to control the operation of the MIDAT system. These circuits may be implemented on the same substrate as the fluidic parts. On-chip integrated control circuitry may result in a highly compact and efficient design capable of making real-time control decisions. The system may comprise a sample size and flow control circuit, temperature cycling and timing circuit, electrophoretic separation bias, data detection and transmission, and a sequencer/timer to control the overall operation. All the data will be transmitted in serial form between an external computer and the MIDAT chip.

A multicomponent, integrated device includes the elements in FIG. 1. The sections in the diagram represent fundamental process components fabricated on silicon. Sample and reagent are injected into the device through entry ports or reservoirs (A), and individual liquid drops are pumped through channels (B) to a thermally controlled reactor, where mixing and restriction enzyme digestion or DNA amplification occurs (C). The drop movement is controlled by simple heating, as differential heating of the two ends of a drop in a capillary tube produces motion (i.e., a thermocapillary pump; Burns et al., 1996). After reaction, the biochemical products are moved by the same pumping method to an electrophoresis channel (D), where DNA migration data are collected by an integral photodiode (E). The output data are sent off the integrated device for signal processing and DNA band identification.

Additional components may be added to the system, provided the channel connection format remains consistent. Such components may comprise low temperature polymer-based channels. A silicon wafer with two liquid reservoirs, 1000×1000×25 µm), each connected to a 200×25-µm channel. The channel and reservoir structures are made of a low-temperature polymer (p-xylylene) using a sacrificial etch procedure. Platinum electrophoresis electrodes are visible within each reservoir. Additional platinum surface electrodes and photodiode detectors have been placed beneath the channels. The interior channel opening is ~100×25 µm. Peltier cooling surfaces, optical sensors, and ultraviolet filters for continuous spectrophotometric analysis may be present.

Using photolithographic fabrication, a silicon wafer having >30 different electrophoresis channels and integral detectors within a 1.25×1.25-cm unit area has been developed. The devices provide a reproducible test platform for understanding gel electrophoresis at a micron-size scale (Webster et al., 1996). The silicon components have provided considerable preliminary information on channel and detector formats. The overall arrangement of components across several 1.25×1.25-cm DNA processing unit repetitions on a single wafer. Within each unit are ~30 different electrophoresis channel and photodiode configurations. The components include an opening to one electrophoresis channel, an associated photodiode, buffer reservoir, external contact points for electronic control, and connections for the integral electrodes and photodiodes. The channels are made using a silicon nitride sacrificial etch process and have an interior cross section of 40×5 µm.

VIII. KITS

All the essential materials and reagents required for the various aspects of the present invention may be assembled together in a kit. The kit generally will comprise reagents to provide the necessary reaction mixture for nucleic acid amplification, including polymerases, nucleotides, buffers, solvents, nucleases, endonucleases, primers, target nucleic acids including DNA and/or RNA, salts, and other suitable chemical or biological components, and a microfabricated substrate defining at least a first channel connected to an isothermally regulated reaction chamber. One or more of the reagents for the reaction mixture may be contained in the microfabricated device and/or in a separate reservoir. When the components of the kit are provided in one or more liquid solutions, the liquid solution is preferably an aqueous solution, with a sterile aqueous solution being preferred.

In a particularly preferred embodiment, the components of the kit may also be provided in dried or lyophilized forms. When reagents or components are provided as a dried form, reconstitution generally is by the addition of a suitable solvent. It is envisioned that the solvent also may be provided in another container means. The kits of the invention may also include an instruction sheet defining the use of the microfabricated substrate to amplify nucleic acids.

The kits of the present invention also will typically include a means for containing the reagent vials and microfabricated substrate in close confinement for commercial sale such as, e.g., injection or blow-molded plastic containers into which the desired vials are retained.

IX. DIAGNOSTICS

The diagnostic system of the present invention generally involves determining either the type or the amount of a wild-type or mutant nucleic acid segment amplified from a biological sample using the chip-based devices of the invention. The biological sample may be from a patient suspected of having a variety of diseases including cancer. Irrespective of the disease, it will be understood that the detection of a mutant is likely to be diagnostic of a disease, and that the detection of altered amounts of the target nucleic acid segment is also likely to have diagnostic implications, particularly where there is a reasonably significant difference in amounts between the patient and samples from a normal subject.

The type or amount of the target nucleic acid present within a biological sample, such as a tissue sample, may be determined or identified by means of a molecular biological assay, particularly an isothermal nucleic amplification reaction in a microfabricated substrate defining at least a first channel connected to an isothermally regulated reaction chamber connected to a nucleic analysis component and a detector for the amplified product. Additionally, any of the foregoing microfabricated substrate nucleic acid amplification, processing, and detection systems may be employed as a diagnostic system in the context of the present invention.

The following examples are included to demonstrate preferred embodiments of the invention. It should be appreciated by those of skill in the art that the techniques disclosed in the examples which follow represent techniques discovered to function well in the practice of the invention, and thus may be considered to constitute preferred modes for its practice. However, those of skill in the art should, in light of the present disclosure, appreciate that many changes may be made in the specific embodiments which are disclosed and still obtain a like or similar result without departing from the spirit and scope of the invention.

In the experimental disclosure which follows, the following abbreviations apply: eq (equivalents); M (Molar); M (micromolar); N (Normal); mol (moles); mmol (millimoles); µmol (micromoles); nmol (nanomoles); gm (grams); mg (milligrams); µtg (micrograms); L (liters); ml (milliliters); µl (microliters); cm (centimeters); mm (millimeters); µm (micrometers); µm (nanometers); ° C. (degrees Centigrade); Ci (Curies); MW (molecular weight); OD (optical density); EDTA (ethylenediamine-tetracetic acid); PAGE (polyacrylamide gel electrophoresis); UV (ultraviolet); V (volts); W (watts); mA (milliamps); bp (base pair); CPM (counts per min).

EXAMPLE 1

This example is a minimal fully integrated device and would include the elements identified in FIG. 1. In the chip format, sample and reagent are injected into the device through entry ports (FIG. 1A) and the solutions pumped through channels (FIG. 1B) to a thermally controlled reactor where mixing and isothermal nucleic acid amplification reactions (SDA, Qβ-replicase, etc.), restriction enzyme digestion, ligation, phosphorylation, dephosphorylation, sequencing, other nucleic acid amplification reactions (e.g. PCR™), or other enzymatic or chemical reaction known to those of skill in the art occurs (FIG. 1C). The biochemical products may then moved by the same or a different pumping method to an electrophoresis channel (FIG. 1D), where nucleic acid migration data are collected by a detector (FIG. 1E) and exported as electronic information. A component of the system is a thermocapillary pump capable of connecting diverse individual elements.

The microfabricated elements in this example are capable or performing several processing steps in conventional DNA analysis. The individual elements have the potential for combination into a complete DNA genotype analysis processing path. Each component was developed using only silicon or glass photolithographic production methods. As a consequence, all components retain the ability to be fabricated concurrently on the same substrate wafers. The use of common fabrication methods allows the assembly of increasingly complex, multicomponent, integrated systems from a small, defined set of standardized elements. Fine control of discrete drop location is only dependent on the density of individual heating elements or other fluid movement devices along the channel. Detection of the drop location within the channel may be performed by using capacitors or conductive wires as sensors. Because the thermocapillary pump mechanism requires no external force (other than application of heat), it should remain scaleable within a wide range of integrated device sizes. Finally, because each droplet is moved uniquely, devices that incorporate branching pathways or parallel sample analysis present no inherent obstacle, other than requiring more complex electronic control circuitry.

Thermocapillary Pump

The thermocapillary pump provides movement of discrete drops in micron-sized channels with no moving parts or valves. A pumping system based on individual drop movement has three advantages for DNA and/or nucleic acid analysis: samples may be readily divided and mixed, the sample volume may be determined by measuring the drop length, and each sample is kept separate, reducing the risk of cross-contamination.

Figure 5:
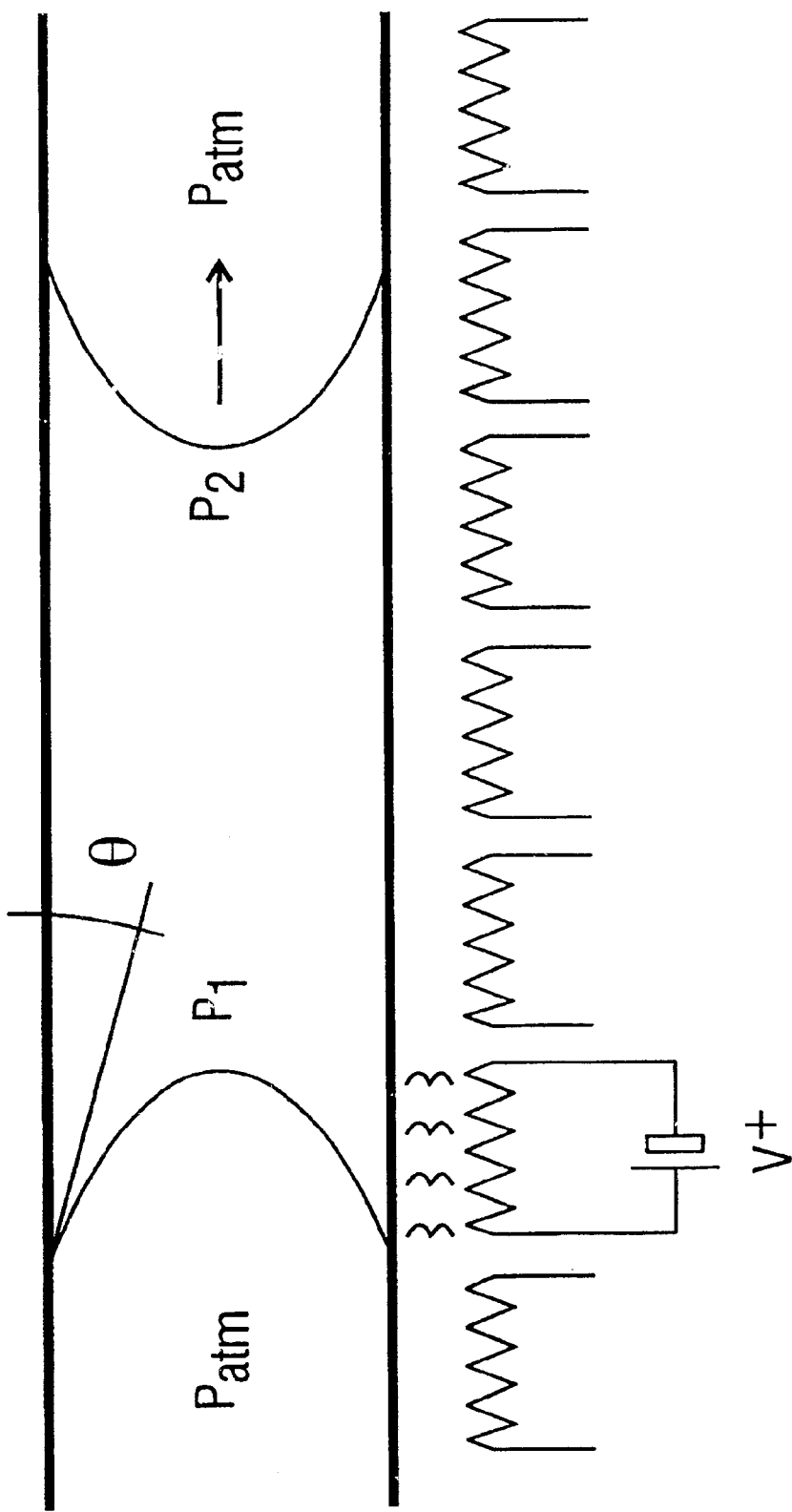
FIG. 5. Schematic drawing showing the principle of thermally induced drop motion in a closed channel. The case of a single aqueous drop in a hydrophilic channel is presented, where V is an applied voltage, $P_{atm}$ is atmospheric pressure, $P_2$ is the receding-edge internal pressure, $P_2$ is the advancing-edge internal pressure, and $\theta$ is the contact angle of the liquid-gas-solid interface. The contact angle will depend on the surface characteristics of the channel and the constituents of the drop, with a hydrophilic interaction giving $\theta$ between 0° and 90°, and a hydrophobic surface giving $\theta$ between 90° and 180°. Surface treatments can also reduce contact angle hysteresis and, therefore, reduce the temperature difference necessary for drop motion.

Motion of discrete liquid samples in micron-sized channels may be accomplished by differentially heating the drop interfaces (FIG. 5). In channels, a pressure difference occurs across the liquid-air interface (i.e., capillary pressure). The pressure difference, $\Delta P_c$, is a function of the surface tension and, for rectangular channels, is given by $$\Delta P_c = P_{atm} - P_{liquid} = (2\sigma \cos \theta)(1/h + 1/w), \quad (18)$$

where $\theta$ is the contact angle, h is the channel height, w is the channel width, and $\sigma$ is the liquid-vapor interfacial tension given by $$\sigma = \sigma_o(1-bT), \quad (19)$$

where $\sigma_o$ and b are positive constants and T is the temperature (Probstein, 1989). Increasing the temperature on one end of the drop decreases the surface tension and, therefore, increases the internal pressure on that end. The pressure difference between the two ends pushes the drop towards the direction of lower pressure at a rate given by (ignoring edge effects, h<<w)

$$(v) = (h/6 \mu L)[(\sigma \cos \theta)_a - (\sigma \cos \theta)_r], \quad (20)$$

where $\mu$ is the viscosity, L is the length of the drop, and the subscripts a and r refer to the advancing and retreating interfaces, respectively. Note that contact angle hysteresis ($\theta_a \neq \theta_r$) requires a threshold pressure difference for positive motion (Tenan et al., 1982, Dussan, 1979).

A device capable of moving and mixing nanoliter drops using differential heating was constructed by bonding a surface-etched glass wafer to a silicon substrate. A standard aqueous acid wet-etch is used to produce channels on the 0.5-min glass wafer having two parallel lanes merging into a single lane of the same cross-sectional dimensions (a Y shape) with dimensions 500 $\mu$m wide and 25 $\mu$m deep. Metal heaters are patterned on the silicon substrate having the same Y format and are protected from liquid by a thin-film barrier. The elements are designed to match the channel layout and are arrayed as two parallel lanes, each 500 $\mu$m wide, merging into one lane. The individual heaters consist of paired aluminum wires winding across a 500×500 $\mu$m region. Broad metal areas on either side of the elements are bonding locations for connection to external circuitry. The heaters are formed by using an inlay process to prevent defects in the barrier layer. A scanning electron micrograph of a heater wire in cross section showed the deposited aluminum, silicon oxide, and silicon nitride layers. The plasma-enhanced chemical vapor deposition process for forming the silicon oxide and silicon nitride layers results in an undefined stoichiometry; therefore, the layers are designated $SiO_x$ or $Si_xN_y$. The width of the aluminum element is 5 $\mu$m. The complementary heater and channel wafers are aligned and bonded with an adhesive to form the finished device Heater Element Wafer Fabrication Heater elements were made with a silicon wafer (p-type, 18–22 fl-cm, boron≈concentration≈$10^{15}$ cm$^{-3}$) as a substrate for growth of $SiO_2$ thermal oxide (1 $\mu$m). A photoresist (AZ-5214-E; Hoescht-Celanese) was applied to the wafer and spun at 3000 rpm for 30 sec. The resist was patterned using a mask (M1) and developed. Reactive ion etching (PlasmaTherm, St. Petersburg, Fla.) was performed to 0.35-$\mu$m depth into the $SiO_2$ layer at the following conditions: $CHF_3$, 15 standard cubic centimeters per minute (sccm); $CF_4$, 15 sccm; 4 mTorr; de bias voltage of 200 V, 100 W, 20 min. The etch depth was measured by profilometer, and 0.35-$\mu$m metallic aluminum was electron beam deposited. The resist and overlying metal were lifted off by development using Microposit 1112A remover in solution (Shipley, Marlboro, Mass.). The barrier layers covering the aluminum elements consist of sequentially deposited 1 $\mu$m $SiO_x$, 0.25 $\mu$m $Si_xN_y$, and 1 $\mu$m $SiO_x$ using plasma-enhanced chemical vapor deposition. Reactive ion etch was used to etch contact holes to the metal layer using a second mask (M2) with conditions: $CHF_3$, 15 sccm; $CF_4$, 15 sccm; 4 M Torr; and dc bias, voltage of 200 V, 100 W, 120 min. Each heating element used as a temperature sensor was calibrated by measurement of electrical 5 resistance at 22° C. and 65° C. under constant voltage; intermediate temperatures were estimated by linear interpolation.

Channel Wafer Fabrication

Channels were prepared on 500-$\mu$m-thick glass wafers (Dow Coming 7740) using standard aqueous-based etch procedures. The initial glass surface was cleaned and received two layers of electron beam-evaporated metal (20 nm chromium, followed by 50 nm gold). Photoresist (Microposit 1813) was spun at 4000 rpm for 30 sec, patterned-using a mask (G1), and developed. The metal layers were etched in chromium etchant (Cr-14; Cyantek, Newark, Calif.) and gold etchant (Gold Etchant TFA; Transene, Rowley, Mass.) until the pattern was clearly visible on the glass surface. The accessible glass was then etched in a solution of hydrofluoric acid and water (1:1). Etch rates were estimated using test wafers, with the final etch giving channel depths of 20–30 $\mu$m. For each wafer, the depth of the finished channel was determined using a surface profilometer. The final stripping steps removed the remaining photoresist material (PRS-2000; J. T. Baker) and metal layers (Cr-14 and Gold Echant TFA).

Glass-to-Silicon Wafer Bonding and Channel Pretreatment

Channels etched on glass were bonded to the heater element wafer using a thin film of applied optical adhesive (SK-9 Lens Bond; Sumers Laboratories, Fort Washington, Pa.). The bond was cured under a UV light source (365 nm)

for 12–24 h. Tests of cured adhesive samples indicated little or no inhibition of restriction endonuclease or thermostable DNA polymerase. Prior to each drop-motion study, the bonded channels were prepared by washing with ≈100 µl each of the following solutions in series: 0.1 M NaOH, 0.1 M HCl, 10 mM Tris. HCl (pH 8.0), deionized $H_2O$, Rain-X Anti-Fog (Unelko, Scottsdale, Ariz.), and bovine serum albumin at 500 µg/ml (restriction enzyme grade; GIBCO/BRL).

Movement and Mixing of Liquid Sample

Two 80-nl drops at their starting locations in the branches of the Y-channel; the hydrophilic surface of the channel allows the process to occur spontaneously. The drop volumes are ≈60 nl and are calculated from the drop length and the known channel cross section. Activating the heaters under the left interfaces propels the drops forward to the channel intersection where they meet and join to form a single larger drop. The combined drop is stopped by turning off all heating elements and may be reversed by heating the right interface. Additionally, circulation patterns generated in the drop during motion aid in mixing the liquid sample studies using the metal elements as both heaters and temperature sensors demonstrate that a temperature differential of 20–40° C. across the drop is sufficient to provide forward motion in this particular channel.

Other sample-handling operations may be performed with this device. For example, drop splitting may be accomplished in two ways. First, a drop may be moved from the single channel, past the Y-channel intersection, and into the two separate channels. While the motion of the drop is accomplished by heating the retreating interface, the amount of liquid that enters each of the two channels may be controlled, by selectively heating one of the advancing interfaces. The drop will preferentially move into the less-heated branch channel. Alternatively, splitting may be performed on a drop held in a single channel by localized heating at the drop's center until a bubble of water vapor forms. Continued heating of the expanding water-vapor bubble propels the two drop-halves in opposite directions. Although an increased gas-phase, pressure is responsible for this latter motion, properly placed, air vents in the channel may allow the split drops to be moved independently using thermocapillary pumping To confirm compatibility of the propulsion system with DNA samples and enzymes, an integrated system was tested combining drop motion, sample mixing, and controlled thermal reaction (FIG. 1A–C). A sample containing plasmid DNA (supercoiled BluescriptSK; Stratagene) was loaded into one branch of the Y channel, and a second sample containing Taq I restriction enzyme and digestion buffer was loaded into the other. After sample merging by thermocapillary pumping, the combined drop was maintained at 65° C. for 10 min using the integral heaters and temperature sensors. Capillary gel electrophoresis of the reaction products confirmed that DNA digestion on the silicon device was similar to reactions performed in a standard polypropylene vessel. The enzymatic reaction occurred by moving two drops (Taq I restriction enzyme and supercoiled plasmid) down separate channels using the thermocapillary technique, combining the drops, and heating the merged sample to 65° C. in the channel. After the reaction, the sample was expressed from the microfabricated device and analyzed by conventional capillary get electrophoresis. The electrophoretic chromatogram shows complete digestion products (elution time, 18–22 min) and minor residual undigested DNA (elution time, 34 min).

Drop Motion and Restriction Enzyme Digestion

The bonded channel device was placed on a stereoscope stage (Olympus SZ1145), and the contact pads for the heating elements were connected to a regulated power supply. Aqueous samples were applied to each of the Y-channel branches by gently touching a suspended drop to channel opening and allowing capillary action to draw the sample into the device. Measurements of drop length in the channel provided a visual check of the loaded volumes. Heating of the drops occurred by passing ≈30 V dc through the element in short pulses and observing the movement of the drops. A small detectable reduction in drop volume from evaporation was noted in each study, usually <30% of the initial drop length. Drop movement was recorded with a Hamamatsu (Middlesex, N.J.) video camera on videotape, and still images were obtained from the videotape without modification.

For the restriction enzyme digestion of DNA, a drop containing 0.2 unit of Taq I restriction enzyme in reaction buffer (100 mM NaCl/10 mM $MgCl_2$/10 mM Tris-HCl, pH 8.0), 150 nl total volume was introduced into one branch of a Y-channel while a drop containing 150 nl of 0.1 µg of supercoiled plasmid per µl (Bluescript SK; Stratagene) was introduced into the other. Following drop motion, digestion occurred by holding the drop at a previously calibrated 65° C. for 10 min using ≈4 V de. The single channel portion of the device was uniformly heated by using seven contiguous heater elements, and the temperature was monitored by measuring electrical resistance. The electronic control system consisted of a National Instruments (Austin, Tex.) LabView controller and virtual instrument software operating on an Apple Macintosh 950.

PCR™ on Silicon Wafer Surfaces

PCR™ was performed using standard buffer and primer concentration conditions for Thermus aquaticus DNA polymerase enzyme (Mullis and Faloona, 1987, Artheim and Erlich, 1992). PCR™ temperature profiles were as follows: 94° C. for 4 min, preincubation; 94° C. for 1 min, 62° C. for 1 min, 72° C. for 1 min, 35 cycles; 72° C. for 10 min, final extension is specific for a portion of the mouse Tfe3 locus and produces a 460-bp-amplified product (primer A, 5'-TAAGGTATGCCCCTGGCCAC-3' (SEQ ID NO:1); primer B, 5'-AAGGTCAGCACAGAGTCCTCA-3') (SEQ ID NO:2 (Roman et al., 1992). For each experimental run a complete 75-µl reaction mixture was prepared using 100 ng of purified genomic mouse DNA as template and divided into three reactions of 25 µl each. The first reaction was maintained at room temperature for 2 h; the second was reacted in a thin-wall polypropylene tube under mineral oil and cycled in a standard thermal cycler; and the third was placed on the surface of the described heater wafer within a small polypropylene ring (4 mm diameter, 1.5 mm height) and covered with light mineral oil. Wafer temperatures were determined by measuring changes in heater element resistance and were controlled by a National Instruments LabView controller and software operating on an Apple Macintosh 950. On completion of the reactions, the three samples were examined for efficiency of amplification by agarose gel electrophoresis and ethidium bromide staining.

Capillary Gel Electrophoresis

Following PCR™ amplification or restriction enzyme digestion, DNA genotyping reactions are typically analyzed by gel electrophoresis. To demonstrate that standard DNA gel electrophoresis can operate in micron-sized channels identical to those used for drop motion, studies were performed using etched glass channels bonded to planar quartz. Channels etched on glass were bonded to a quartz microscope slide using SK-9 optical adhesive and 24-h UV-illuminated curing. A 10% acrylamide electrophoresis mix (10% acrylamide/0.3% bis-acrylamide/89 mM Tris. HCl/89 mM sodium borate/10 mM EDTA/0.001% N,N,N', N'-tetramethylethylenediamine/0.01% ammonium persulfate) was injected into the channel and allowed to polymerize. Following polymerization, the slide was immersed in a horizontal electrophoresis apparatus containing gel running buffer (89 mM Tris-HCl/89 mM sodium borate/10 mM EDTA). A 50-μl sample of 100 ng of DNA per μl (Bluescript SK plasmid digested with Msp I) containing 0.01% YOYO-1 dye (Molecular Probes) was placed at the negative electrode opening of the channel, and current was applied until a green fluorescing band appeared at the buffer-to-gel interface (12 V/cm, ≈2 min). The remaining DNA solution was rinsed away, replaced by running buffer, and electrophoresis was continued by applying current at 12 V/cm for 120 min. The gel was photographed under an incandescent light source and viewed using an Olympus stereo microscope and Nikon 35 mm camera with no filters. Separation of the component bands in a range of 100–1000 bp is clearly visible <1 mm from the buffer reservoir-to-gel interface. The high resolution of the detector (in this case, a conventional stereo microscope at×10 magnification) allowed the use of an unusually short gel, and resolved several migrating bands.

Capillary gel electrophoresis of DNA samples was performed using a Beckman P/ACE instrument with a laser-induced fluorescence detector and 37 cm length, 100 μm diameter, linear polyacrylamide gel capillary according to manufacturer's recommendation. Samples were stained, then injected electrokinetically using a water-stacking procedure and run at 7400 V dc for 45 min.

Additional DNA Analysis System Components

Using microfabrication processes compatible with the construction of the thermocapillary pump channels, a thermal cycling plat-form, a gel electrophoresis chamber, and a DNA detector were fabricated and tested. PCR™ thermal cycling was performed on a silicon substrate using heaters and temperature sensors from the same processed wafer as the thermocapillary pump. In this thermal reaction chamber device, a group of four closely spaced heater elements were tested to ensure compatibility with the standard PCR™ biochemical reactions. The device successfully amplified a single-copy sequence from total genomic mouse DNA in small aqueous drops (10–25 μl) placed on the processed silicon surface and covered with mineral oil to prevent evaporation. However, variations in PCR™ amplification efficiency as large as 4-fold were observed between repetitions of the study.

Diffusion Diode Wafer Fabrication

Integral DNA sensor elements were fabricated on the surface of silicon wafers to electronically detect migrating DNA bands. A sensor capable of detecting decay events from radioactively labeled DNA may be fabricated on the surface of silicon wafers as p-n-type diffusion diode. Radiation detection was chosen for the initial device since such diodes have a high sensitivity, small aperture dimensions, and well-known fabrication and response characteristics. Testing of the device with $^{32}$P-labeled DNA demonstrates that it readily functions as a sensor capable of detecting single impacting events. For each diode element, the diffusion regions of the central detector are ≈300 gm long and 4 μm wide and guard ring shield the electrodes. This diode, although currently configured for high-energy β particle detection, can also operate as a fluorescent light detector when combined with a matched fluorophore, wavelength filter, and excitation source.

Diode detectors were prepared on 200 Ω-cm, (100), boron-doped, p-type silicon wafer substrates. Diffused layers of phosphorus ($5\times10^{14}$ cm$^{-2}$) and boron ($1\times10^{15}$ cm$^{-2}$) were ion-implanted onto the sample in lithographically defined regions (mask D1); thermal silicon oxide was grown (0.2 μm at 900° C.) over the wafer; and contact holes were etched to the diffusion layer with buffered hydrofluoric acid solution. A 3.3-μm layer of photoresist (Microposit 1400-37) was patterned to define the metal pads (mask D2); 50-nm chromium followed by 400-nm gold was evaporated over the resist; and the metallization lifted off the regions retaining the resist. In some initial radiation sensitivity tests, a layer of photoresist (Microposit 1813) was applied across the wafer and baked for 110° C. for 30 min to form an aqueous solution barrier. Additional studies used a double layer of plasma-enhanced chemical vapor deposition silicon oxide and silicon nitride as a barrier, similar to the layers described for the heater-element wafer. Radioactive phosphorus ($^{32}$P) decay events were detected using a sample of labeled DNA in PCR™ buffer placed on the barrier layer. To test sensitivity, the detector was connected to a charge-sensitive preamplifier (model 550A, EV-Products, Saxonburg, Pa.), followed by a linear shaping amplifier and a standard oscilloscope, and events were computer recorded.

The resolving ability of DNA gel electrophoresis systems may be improved by the proximity and narrow width of silicon-based detectors placed immediately beneath the gel channel. Microfabricated diodes may be placed within 1 micron of the gel matrix and can have an aperture of 5 microns or less. Since the gel length required for the resolution of two migrating bands is proportional to the resolution of the detector, the incorporation of micron-width electronic detectors may significantly reduce the total gel length required for DNA analysis without sacrificing band-reading accuracy.

Currently, optical methods using efficient fluorophores can detect atto-molar concentrations (corresponding to ≈$10^5$ DNA molecules) migrating in capillary channels of 8×50 μm internal cross section (Woolley and Mathies, 1994). Reactions for synthesizing such DNA quantities can reasonably occur in 10 μl. An integrated system designed for picoliter volumes may require channel dimensions on the order of 10 μm$^2$×100 μm (cross section×length). At this size, thousands of individual devices would occupy a single 100-mm-diameter wafer.

EXAMPLE 2

Isothermal Amplification in a Silicon Chip

The compatibility of the isothermal amplification reagents (available from Becton Dickinson), particularly enzymes, with the silicon DNA chip assay format was investigated. The components of an SDA reaction for amplification of the IS6110 element of *Mycobacterium tuberculosis*, except for the enzymes, were assembled externally to the chip, denatured in a boiling water bath for 2 min and cooled to 52° C. for 2 min. The enzymes were added to bring the total volume to 50 μL containing 35 mM K$_2$HPO$_4$ PH 7.6, 50 mM NaCl; 10 mM TRIS pH 7.6, 9 mM MgOAc$_2$, 1.4 mM dCTPα S, 0.2 mM TrP, 0.2 mM dGTP, 0.2 mM dATP, 18.5% (v/v) glycerol, 1 mM DTr, 500 ng human DNA, 500 nM SDA primers (S$_1$ and S$_2$), 2.5 mM SDA bumpers (B$_1$ and B$_2$), $10^6$ *M tuberculosis* genomes containing the IS6110 target, 160 units BsoBI and 13 units exo $^-$Bst polymerase. The amplification and bumper primers were as follows, with the BsoBI recognition sequence shown in bold and the IS6110 target binding sequence underlined:

5'-C G A T T C C G C T C C A G A C T T C T C G G G T CTACTGAGATCCCCT-3' (S1) (SEQ ID NO:3)

5'-ACCGCATCGAATGCATCTCTCGGGT
AAGGCGTACTCGACC-3' (S2) (SEQ ID NO:4)
5'-CGCTGAACCGGAT-3' (B1) (SEQ ID NO:5)
5'-TCCACCCGCCAAC-3' (B2) (SEQ ID NO:6)

A 4 µL sample of the amplification reaction was immediately placed in a 60 µm deep, 5.1 cm long glass channel etched in 7740 PYREX (Dow Coming) and adhered to a silicon chip, filling the entire channel. The channel was open at both ends. The channel chip was placed on a heater element wafer in contact with about one third of the sample, and the temperature was held at 52° C. for up to 30 min to allow the amplification reaction to proceed. To remove the sample, about 5 µL of amplification reaction buffer without the enzymes was placed at one end of the channel and the sample was withdrawn from the other end using a sequencing pipette tip. This process was repeated four times to wash the channel. The total volume recovered was about 20 µL. The amplification reaction was then stopped by boiling in a water bath and amplification was detected in a chemiluminescent assay as described in U.S. Pat. No. 5,470,723. The biotinylated capture probe and the alkaline phosphatase labeled detector probe used in the assay are described in Spargo, et al. (1993). As a control, the same SDA reaction was performed in a test tube in the conventional manner. Target amplification efficiency was equivalent in the conventional SDA reaction and on the DNA chip, with amplification of almost a million-fold. This demonstrated that the physical changes in the environment on the DNA chip, including temperature gradients, inhibitors and surface interactions, did not adversely affect the amplification reaction.

The ability of the separate components of the amplification reaction to adequately mix within the channels of the DNA chip was then investigated. In one study, 160 nL of enzyme mix was placed in a channel prepared as described above. The target was denatured at 95° C. in amplification buffer (3.84 µL) and cooled to 52° C. prior to loading into the channel with the enzyme. The total volume of the reaction mix filled the entire channel. Amplification was allowed to proceed at 52° C. for 16 min and assayed as before. In a second study, the target in amplification buffer (1.5 µL) was loaded into the channel and moved over the heating element using air pressure. Using the heater element the temperature was raised to 80° C. for about 10 sec (temperature spiked to about 95° C.) to denature the target, then cooled to 52° C. The enzyme mix (1.5 µL) was added to the channel with the denatured target to fill the channel. The amplification reaction was performed (15 min reaction time) and assayed as before. In an additional study, 1 µL of enzyme mix was loaded into one end of the channel and 1 µL of target in amplification buffer was loaded into the other end. The portion of the channel containing the target was heated to 80° C. for about 15 sec to denature the nucleic acids (temperature spiked to about 90° C.) and cooled to 52° C. The two samples were brought into contact by applying air pressure to the open ends of the channel until the target and enzyme aliquots moved into contact with each other. The reaction was held at 52° C. on the heater element for 15 min, then removed with washing as described above. Chemiluminescent detection of amplification products in all of these studies revealed efficient amplification of the target, indicating adequate mixing and diffusion of the reactants in all channel configurations and protocols tested.

EXAMPLE 3

This example describes approaches to the problem of forming a moisture barrier over electrical elements of the microscale device. Initial prototypes employed 5000 angstroms of aluminum and covered it with PECVD $SiO_x$. Upon testing, it was determined that the liquids were penetrating this later and destroying the aluminum heating elements.

Without clear evidence what was causing this problem, it was hypothesized that the step height of the aluminum was causing cracks in the passivation layer (the oxide). In order to alleviate the cracking problem, a layer of $Si_xN_y$ tried between two layers of $SiO_x$, with the thought that the additional thickness would overcome the cracking caused by the step height. It did not.

As a follow-up approach, a thinner layer (500 angstroms) of aluminum was tried. This gave 1/10th the step height of the original prototype devices. On top of this aluminum, a triple layer of $SiO_x$, $Si_xN_y$, and $SiO_x$ was employed. Moreover, the process for making the $Si_xN_y$ layer was changed to one which would give a more dense layer. This appeared to solve the problem. However, the thinner layer of aluminum created a higher resistance which was not acceptable. It was determined that one needed a way to generate thicker layers of aluminum for lower resistance, yet keep the surface relatively smooth (planar). An etch back process was used (now called "the inlay process") to accomplish the task. By etching back into a layer of $SiO_x$ depositing aluminum in the resulting cavity, then stripping the resist mask, a surface was obtained with a step height low enough to prevent cracking of the passivation layers.

It was also discovered that the metal bonding pads were not adhering well to the initial PECVD $SiO_x$ layer. To overcome the problem, the process was modified by using a wet thermal $SiO_2$ layer.

EXAMPLE 4

This example describes approaches to enhancing droplet motion by surface treatment. In this regard, the principle of using surface tension to cause droplets to move may be applied to either hydrophilic or hydrophobic surfaces. Glass, for instance, is naturally hydrophilic with a near zero contact angle with water. Because the oxide coating of the present invention is made principally of the same material as glass, it was expected that the devices would also exhibit near zero angles. It was discovered, however, that the actual construction materials had contact angles far from zero, thus enhancing the effects of contact angle hysteresis (discussed in greater detail in Example 3). For instance, water gave a contact angle (static) of ~42° on polyamide, ~41° on $SiO_2$ (major component of most glasses), ~62° on silicone spray. To enhance the surface effectiveness, several treatment processes for both hydrophilic and hydrophobic surfaces were tried, as described below.

To improve the hydrophilicity of a surface, several cleaning procedures were tried. It has been reported that surface contamination and/or roughness can reduce the hydrophilicity of surfaces. Therefore, a high concentration chromic acid cleaning, a high concentration sulfuric acid cleaning a baking procedure (to 600° C. for 8 h to burn off contaminates), and surface coatings were tried. The acid cleaning procedures were not as effective as the baking procedure; however, neither proved to be compatible with the devices since the concentrated acids would attack the aluminum pads and the high temperature could peal the aluminum (melting pt. ~660° C.) or break the adhesive bond between the heater chip and the channel.

Rain-X antifog (commercially available) as a treatment was observed to work. This is a surface treatment which makes surfaces hydrophilic. Although, the resulting surfaces may not be 0°, by using this coating the entire surface gets treated giving a uniform surface for the droplet. Experimentally, it was found that Rain-X antifog treatments greatly enhanced droplet motion studies using heat. Another such treatment which was tested but which did not work was a material called SilWet. This material is used in the agriculture industry for enhancing the wetting of plants with agricultural sprays.

To obtain hydrophobic surfaces, capillaries were coated with Rain-X and silane treatments. Neither of these gave angles much greater than 90°, therefore, would not work with this mechanism. These treatments would have to have given angles ~180° to be useful for hydrophobic studies of motion. Eventually, it was discovered that one could apply a teflon coating that was sufficiently hydrophobic to possibly warrant future tests.

EXAMPLE 5

This example describes approaches to droplet motion by heat treatment. As noted previously (above), the contact angle on the advancing end of a liquid droplet in motion (known as the advancing contact angle) is greater that the that on the receding end (receding contact angle). In the case of a hydrophilic surface—such as water on glass—this tends to create a back pressure countering attempts at forward motion by heating the back side of a droplet. This is best shown by a simple model describing laminar flow through a channel.

Average Flow Through a Circular Channel:

$$\langle v \rangle = -\Delta P * [R^2/(8\mu L)]$$

where:

$\Delta$ = value at back – value at front end of droplet $\Delta P = (1/R) * (\Delta G)$ = pressure difference between droplet ends $\Delta G$ = change in surface tension between ends of the droplet.

$R$ = channel radius $L$ = droplet length $\mu$ = viscosity

Also, for water, $\Delta G$=-constant * $\Delta T$, where temperature increases lower the surface tension of most liquids (constant=0.16 dyn/cm for water).

Therefore:

$$\langle v \rangle = -(\Delta G)*(1/R)*[R^2/8\mu L)] = [-0.16*\Delta T*R/(8\mu L)]$$

where:

$\Delta T = T_{back} - T_{front}$ giving $$\langle v \rangle = [0.16*R/(8\mu L)]*(T_{back} - T_{front}).$$

This expression indicates that any heating on the back end of the droplet (if the front remains at a lower temperature) will cause the liquid droplet to move. This was not the case experimentally, however. By way of studies using glass capillaries, it was found that there was a minimum temperature difference required to move the droplet. This effect is believed to be the result of contact angle hysteresis (CAH). In CAH, the advancing contact angle is greater than the receding contact angle resulting in a sort of back pressure which must be overcome to achieve droplet movement. CAH occurs when the interface is placed in motion (dynamic angles). To account for this effect, it was included in a steady-state (1D) model for flow. For instance, if the advancing angle is 36° and the receding angle is 29° (with the front of the droplet being 25° C.), then the back of the droplet would need to be heated to ~60° C. for a 1 mm long droplet in a 20 μm high channel. This is just one example situation.

It was discovered experimentally, however, that the channel dimension and fluid parameters (other than surface tension) do not affect whether or not the droplet will move. They do determine the magnitude of motion (if it occurs). What does determine whether motion will occur or not is the following inequality:

$$G_{front}/G_{back} > (R_{front}/R_{back})*(\cos \beta_{back}/\beta_{front})$$

where: β=contact angle.

The present calculations suggest that a ~35° C. difference between the front and back of a droplet should be sufficient to initiate droplet motion in a system with advancing angles of 36° and receding angles of 29° in a 20 μm high channel. Experimental testing of actual devices however, showed that the front of the droplet heats relatively quickly thus reducing the temperature difference needed for movement between the front and the back of the droplet. This effect required the invention to use higher voltages to obtain droplet motion. Voltages typically in the range of ~30° Volts were found to be required to obtain motion. Further studies showed that the resulting temperature difference was ~40° C. between the front and back of the droplet thus corroborating the initial determination of the requirements.

Discrete droplet motion in a micromachined channel structure using thermal gradients was demonstrated. The device consists of a series of aluminum heaters inlaid on a planar silicon dioxide substrate and bonded by glue to a wet-etched glass channel (20 μm depth, 500 μm width). Liquid samples were manually loaded into the two channels on the left using a micropipette. Heating the left interface of each droplet propels it toward the intersection of the channels. At the intersection, the droplets meet and join to form a single larger droplet. Note that, since the channel cross-section is 20 μm×500 μm, the volume of each of these droplets may be calculated from their lengths and is approximately 50 nanoliters.

The heaters along the entire surface of the channel allow it to be used as a thermal reaction chamber in addition to a droplet-motion device. The upper droplet in the figure contains a DNA sample, while the lower contains a restriction digest enzyme (TaqI) and digestion buffer. Following sample merging, the combined droplet was maintained at 65° C. for 30 min using the integral heaters and temperature sensors. The completed enzymatic reaction was confirmed by expressing the droplet from the right end of the channel and loading it onto a capillary gel electrophoresis system with a laser-induced fluorescence detector. The chromatogram produced by the silicon-device sample was similar to chromatograms generated from DNA digests runs in a standard polypropylene microreaction vessel.

EXAMPLE 6

This example describes various approaches for bonding channels to the substrate which contains circuitry for heating and temperature sensing of the device of the present invention (see discussion of two-part construction, above). First attempts involved Polyamide; regular polyamide was unsatisfactory in that it was found the two pieces would not stick together.

Follow-up attempts involved a photo-definable Polyamide. This produced a sticky surface, but would not give a perfect seal along the channel. It was discovered that the solvents released during the final baking process were causing pockets in the polyamide layer. An adhesion layer was needed which would seal by "curing" and not release solvents.

Several different epoxies and glues were investigated, as listed in Table 1 below.

TABLE 1

| | Adhesive | Form | Dries | Texture | Comments |
|---|---|---|---|---|---|
| 1. | Dymax UV Glue | Gel | Clear | Rubbery | Cures on UV exposure. |
| 2. | Carter's Rubber Cement | Goo | Yellow/ Clear | Rubbery | Dries quickly and stringy when thinned. |
| 3. | Borden's Krazy Glue | Liquid | Clear | Hard | Thin, dries on first contact. |
| 4. | UHU Bond-All | Gel/ Goo | Clear | Hard | Dries quickly and stringy when thin. |
| 5. | Dennison Permanent Glue Stick | Paste | Clear | Hard | Will not flow on applying. |
| 6. | Elmer's Glue-All (Borden) | Thick Liquid | White | Hard | Slow drying. |
| 7. | Liquid Nails | Thin Paste | Wood-like | Hard | Thick, dries quickly when thinned. |
| 8. | Devcon 5-Minute Epoxy | Gel | Yellow/ Clear | Hard | Thick, cures on about 5 min. |
| 9. | Scotch Double-Stick Tape | Tape | Clear | Rubbery | Tape. |
| 10. | Dow Corning High Vacuum Grease | Thick Gel | Frosty | Soft | Seals but does not bond. |
| 11. | Nujol Mineral Oil (Perkin Elmer) | Liquid | Clear | Runny | Neither seals (doesn't spread on glass) nor bonds. |
| 12. | Household Goop | Gel/ Goo | Clear | Rubbery | Contact cement which dries stringy. |
| 13. | Permatex Weather Strip Cement | Gel/ Goo | Yellow/ Clear | Rubbery | Dries quickly on stringy when thinned. |
| 14. | Thick Gel Super Glue | Gel | Clear | Hard | Does not cure on contact but does quickly. |
| 15. | DAP Weldwood Contact Cement | Goo | Orange/ Clear | Rubbery | Contact cement which gets stringy when thinned. |
| 16. | Scotch (3M) Photo Mount Spray Adhesive | Thin Goo | Yellow/ Clear | Rubbery | Spray. "Gooey" but not stringy. |
| 17. | Silicone Resin (spray) Lacquer (GC Electronics) | Liquid | Clear | Smooth | Spray. Dries to thin, clear, and sealed coating. |

A preferred glue was a UV cured glue, although the process of applying the UV glue is tedious and requires some practice to avoid putting the glue in places where it does not belong, e.g., in the channels.

Hydroxide bonding and screen printing of bonding substances was also attempted. Another option was glass tape, but the high temperatures required to melt the tape appeared to be too high for the present devices.

EXAMPLE 7

This example describes a nucleic acid amplification reaction on a silicon-based substrate. The established DNA biochemistry steps for PCR™ occur within physiological conditions of ionic strength, temperature, and pH. Thus, the reaction chamber components have design limitations in that there must be compatibility with the DNA, enzymes and other reagents in solution.

To assess biocompatability, components were added to a standard PCR™ reaction. The results indicate PCR™ works well with bond-all glue, goop glue, rubber cement, vacuum grease, silicone spray, reaction vial plastic, stainless steel, wire thermocouple, crushed glass, and glass capillary, but indicated that crystalline silicon, crushed silicon, rubber gasket, polyamide, UV glue, cured silicone sealer, and liquid nails glue may not be the ideal material for biological compatibility. Given these results, it may be desirable to modify the surface of the micromachined silicon substrate with adsorbed surface agents, covalently bonded polymers, or a deposited silicon oxide layer.

To form a biologically compatible heating element, a standard silicon wafer was coated with a 0.5 $\mu$m layer of silicon dioxide. Next, a 0.3 $\mu$m deep, 500 $\mu$m wide channel was etched into the silicon oxide and gold or aluminum was deposited (0.3 $\mu$m thick). This inlay process results in a relatively planar surface and provides a base for deposition of a water-impermeable layer. The impermeable layer is made by a sequence of three plasma enhanced vapor depositions: silicon oxide ($SiO_x$), silicon nitride ($Si_xN_y$) and silicon oxide ($SiO_x$). Since the materials are deposited from the vapor phase the precise stoichiometries are not known. A thin metal heater design was used for this device rather than the doped-silicon resistive heaters previously demonstrated for micromachined PCR™ reaction chambers, since the narrow metal inlay allows viewing of the liquid sample through a transparent underlying substrate, such as glass or quartz. Also, the use of several independent heating elements permits a small number to operate as highly accurate resistive temperature sensors, while the majority of elements are functioning as heaters.

A device fabricated with metal resistive heaters and oxide/nitride/oxide coating was tested for biological compatibility and temperature control by using PCR™ amplification of a known DNA template sample. The reaction was carried out on the planar device using twenty microliters of PCR™ reaction mix covered with mineral oil to prevent evaporation. The reaction mixture was cycled through a standard 35-cycle PCR™ temperature cycling regime using the integral temperature sensors linked to a programmable controller. Since the reaction volume was significantly larger than intended for the original heater design, a polypropylene ring was cemented to the heater surface to serve as a sample containment chamber. In all test cases, the presence of amplified reaction products indicated that the silicon dioxide surface and the heater design did not inhibit the reaction. Parallel amplification studies performed on a commercial PCR™ thermocycler gave similar results. A series of PCR™ compatibility tests indicated that the reaction on the device is very sensitive to controller settings and to the final surface material in contact with the sample.

From the above it should be evident that the present invention may be adapted for high-volume projects, such as genotyping. The microdroplet transport avoids the current inefficiencies in liquid handling and mixing of reagents. Moreover, the devices are not limited by the nature of the reactions, including biological reactions.

EXAMPLE 8

In this example, a test structure is fabricated. The main part is constructed from a two mask process with five layers of materials on top of the Si substrate. Proceeding from the lowest to the uppermost layer, the SiO, serves as an insulator between the Si substrate and the other metal layers, which function as solder pads and heating elements. The Ti layer (250A) is for adhesion of Ni. The layers of Ni (1000 A) and Au (1000 A) act as a diffusion barrier for the solder. The Au layer also serves as a wettable pad. Finally, the layer of solder is for bonding two substrates together. The solder will melt by heating the metal layers. Another substrate that will be bonded has the same construction except for the solder.

A thermo-pneumatic microvalve is utilized in the test structure. A corrugated diaphragm is chosen for its larger deflection and higher sensitivity. The diaphragm (side length=1000 $\mu$m, thickness=3 $\mu$m, boss size length=500 $\mu$m boss thickness=10 $\mu$m) has a deflection of 27 $\mu$M at an applied pressure of 1 atm. This applied pressure is generated by a thermo-pneumatic mechanism, which provides a greater actuation force. A pressure of 1 atm is generated in the cavity between the diaphragm and glass by Freon-11 when it is heated 11° C. above room temperature. Ten masks are expected to fabricate the microvalve.

A portion of a silicon substrate is a p-type (100)-oriented Si wafer of normal thickness and moderate doping (>1 cm). The preferred wafer thickness, however, is ordinarily a function of the wafer diameter. The upper surface of the silicon wafer containing substrate is lapped, polished and cleaned in the normal and accepted manner. Isotropic etching using reactive ion etching (RIE) forms the diaphragm corrugations with photoresist as the masking material.

Deep boron diffusion areas form the rims, center bosses, inlet and outlet holes of the finished device. The deposition of shallow boron diffusion areas to form a diaphragm. The various metal layers, including solder, are then deposited. The deep and shallow boron diffusion processes define the shape of the diaphragm and the etch-stop for the dissolved wafer process.

Following this, the definition of oxide layer to serve as insulator of the solder of the finished device. Ti adhesion/Ni/Au barrier and wettable pads are then deposited. The solder mold of Ni and photoresist is then defined and the first Ni channel is created by surface-micromachined using photoresist as sacrificial layers. The Ni channel hole is defined using EDP to remove the sacrificial layers, and define an channel hole.

A second Ni channel is defined by Ni and photoresist, and inlet and outlet holes are defined using EDP to remove the sacrificial layers.

Lastly, a Ti/Pt heater in glass is anodically bonded to the silicon substrate. Freon fills the cavity through a hole in the glass substrate. This hole is created from a diamond drill bit and sealed with epoxy.

EXAMPLE 9

In this example, a low melting point solder was intended to be utilized in the test structure. Because a universally useful solder-sealed microvalve will be used in a gas phase microanalytical system, it is not desirable to use a high melting point (m.p.) solder (>200° C.), which might affect the gas properties. In addition, a high m.p. solder may affect other components on the device, such as integrated circuits, and increase power consumption. As a result, low melting point solder is required. Bismuth-bearing solders have the lowest m.p.'s of 47–138° C. However, when a test structure was dipped into a pool of solder belonging to this group, all the metal layers dissolved into the solution of solder. Moreover, this solder was not selective in wetting the surface of the test structure.

EXAMPLE 10

In light of the results of the study set forth in Example 7, an attempt was made with commonly available 60:40 Sn:Pb solder (m.p. 183° C.). When the test structure was dipped into a solution of this solder, the metal layers remained intact. Furthermore, these layers demonstrated excellent wettability for the solder, i.e., the solder was confined only to the areas of metals.

EXAMPLE 11

In this example, a device and method for blocking fluid flow in a channel is described. 60:40 Sn:Pb solder, associated with a heating element, is placed within a side channel. The heating element at least partially liquefies the solder and air flow moves the liquefied solder from the side channel into a main channel and cooled, blocking the main channel.

EXAMPLE 12

In this example, a device, which was fabricated using lift-off method described above to pattern hydrophobic regions on glass and silicon substrates, was testing for the separation of water droplets. For the device, a patterned metallic thin film was used to expose regions that were chosen to be made hydrophobic on a hydrophilic substrate. Chromium, Gold or Aluminum was used as the metal layer; the choice of the metal being based on process compatibility with other processing steps and step height coverage of the etched channels.

Line widths as narrow as 10 $\mu$m were patterned on silicon substrates using the methods of the present invention. Water drops separated by lines of hydrophobic and hydrophilic regions patterned by this new technique (the width of the hydrophilic line in the middle is 1 mm). The contact angle of water on the OTS (SAM) coated silicon oxide surface was measured to be approximately 110°.

One can also define hydrophobic regions in etched channels in glass by performing the lithography using a thick resist. It was found empirically that cleaning of the substrates prior to immersion in the OTS (SAM) solution is important; improper cleaning results in films that partially covers the surface.

EXAMPLE 13

The results of Example 10, above, demonstrate that hydrophobic and hydrophilic patterns enable one to define and control the placement of aqueous liquids, and more specifically microdroplets of such liquids, on a substrate surface. Use of this patterning technique to split a liquid droplet into multiple liquid droplets. A concentric pattern of alternating hydrophobic and hydrophilic sectors was imparted to a silicon substrate (the diameter of the circular substrate was 1 cm) using the methods of the present invention as described above. A water drop was placed on the pattern and the excess water pulled away using a pipet, resulting in multiple drops separated from each other.

EXAMPLE 14

In this example, studies to position a water front inside a channel using straight channels (depth ranging from 20–40 $\mu$m and width between 100–500 $\mu$m) with a 500 $\mu$m wide hydrophobic region (or patch) patterned a few millimeters away from the side inlet. Water was placed at the inlet using a sequencing pipette (Sigma, least count 0.5 $\mu$l) and was drawn into the channel by surface forces. The water front stopped at the hydrophobic patch if a controlled amount of liquid was placed at the inlet. However, if the channels were overloaded, the liquid would tend to overrun the hydrophobic patch. This behavior was prominent in the channels with smaller cross-section.

To eliminate the over-running of the liquid over the patches, an overflow channel was introduced in the design to stop the water running over the hydrophobic patch (such as that shown FIG. 3). The dimensions of the channels varied in depth and width as before. Water placed at the inlet is drawn in and splits into two streams at the intersection point. The two fronts move with almost equal velocity until the front in the main channel reaches the hydrophobic patch. The front in the main channel stopped at the hydrophobic patch; however, the other front continued to move to accommodate the excess injected water. Using this overflow channel design, one can successfully stop aqueous liquids for the full range of variation in channel dimensions.

EXAMPLE 15

One embodiment of the device of the present invention (in operation) utilized a heater. Liquid placed at the inlet stops at the hydrophobic interfaces, and more specifically, stops at the liquid-abutting hydrophobic region. The inlet and overflow ports were blocked or heavily loaded with excess liquid to ensure that the pressure generated acts only in the direction away from the inlet holes. The heater resistor was actuated by an applied voltage. The flow of current caused resistive heating and subsequently increases the air temperature in the chamber and, therefore, the pressure. After the pressure builds up to a particular value, a microdrop splits and moves beyond the hydrophobic patch. The drop keeps moving as long as the heater is kept on; the drop velocity decreases as it moves further away. While it is not intended that the present invention be limited by the mechanism by which this takes place, it is believed that the added volume (the volume by which the drop has moved) brings about a decrease in the pressure.

To stop or block the moving drop at a location, two strategies may be employed. In the first method, the inlet and overflow ports were opened to the atmosphere and the heater was slowly turned off. The temperature inside the chamber falls quickly to around room temperature, thereby reducing the pressure inside the chamber. The water from the inlet flows into the chamber to relieve the pressure. In the second method, a hydrophobic vent was placed away from the chamber to the right. As soon as the moving drop goes past the hydrophobic vent, the drop stops moving farther. Cooling the chamber to room temperature at this instant will cause air to flow back through the vent to relieve the low pressure in the chamber.

From the above, it should be clear that the compositions, devices and methods of the present invention permit on-chip actuation using etched chambers, channels and heaters. There is no requirement for mechanical moving parts and the patterns are readily fabricated. While the operations described above have been for simple designs, the present invention contemplates more complicated devices involving the introduction of multiple samples and the movement of multiple microdroplets (including simultaneous movement of separate and discrete droplets).

All of the compositions and/or methods and/or apparatus disclosed and claimed herein may be made and executed without undue experimentation in light of the present disclosure. While the compositions and methods of this invention have been described in terms of preferred embodiments, it will be apparent to those of skill in the art that variations may be applied to the compositions and/or methods and/or apparatus and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

Alberi and Radeka, "Position sensing by charge division," *IEEE Trans. Nucl. Sci.*, 23:251–258, 1976.

Arnheim and Erlich, "Polymerase chain reaction strategy," *Annu Rev Biochem.*, 61:131–156, 1992.

Barony, *Proc. Natl. Sci.* USA, 88:189–193, 1991.

Barringer et al., *Gene*, 89:117–122, 1990.

Belau, Klanner, Lutz, "Charge collection in silicon strip detectors," *Nuclear Inst. Meth.*, 214:253–260, 1983.

Belcarz, Chwaszewska, Slapa, Szymczak, Tys, "Surface barrier lithium drifted silicon detector with evaporated guard ring," *Nuclear Inst. Meth.*, 77:21–28, 1970.

Beni and Tenan, "Dynamics of electrowetting displays," *J. Appl. Phys.*, 52:6011–6015, 1981.

Bertolini, In: Semiconductor Detectors, Amsterdam, North-Holland, 1968.

Bird, Stewart, Stewart, Lightfoot, In: *Transport Phenomena*, John Wiley and Sons, New York, 1960.

Burggraf, Manz, de Roij, Widmer, "Synchronized cyclic capillary electrophoresis: a novel concept for high-performance separations using low voltages," *Analytical Methods and Instrumentation*, 1:55–59, 1993.

Burns, "Small-scale PCR™," *Genome Digest*, 1:6, 1994.

Burns, Mastrangelo, Sammarco, Man, Webster, Johnson, Foerster, Jones, Fields, Kaiser, Burke, "Microfabricated structures for integrated DNA analysis," *Proc. Natl. Acad. Sci.*, 93:5556–5561, 1996.

Cheng, Shoffner, Wilding, "Chip PCR™II: Investigation of different PCR amplification systems in microfabricated silicon-glass chips," *Nucleic Acids Res.*, 24:380–385, 1996.

Colgate and Matsumoto, *J Vac. Sci. Technol.*, 8:3625–3633, 1990.

Datta, "Theoretical evaluation of capillary electrophoresis performance," *Biotechnol. Prog.*, 6:485–493, 1990.

Deme, In: *Semiconductor Detectors for Nuclear Radiation Measurement*, Wiley, New York, 1971.

Drossman, Luckey, Kostichka, D'Cunha, Smith, "High-speed separations of DNA sequencing reactions by capillary electrophoresis," *Anal. Chem.*, 62:900–903, 1990.

Dussan, *Annu. Rev. Fluid Mech.*, 11:371–399, 1979.

Edwards, Brenner, Wasan, In: *Interfacial Transport Processes and Reology*, Butterworth-Heinemann, Boston, pp. 21–36, 1991.

Effenhauser, Manz, Widmer, "Glass chips for high-speed capillary electrophoresis separations with submicrometer plate heights," *Anal. Chem.*, 65:2637–2642, 1993.

Effenhauser, Paulus, Manz, Widmer, "High-speed separation of antisense oligonucleotides on a rnicromachined capillary electrophoresis device," *Anal. Chem.*, 66:2949–2953, 1994.

Esashi, Shoji, Nakano, "Normally close microvalve and micropump fabricated on a silicon wafer," *Iternational Workshop on Microelectromechanical Systems* (MEMS), Institute of Electrical and Electronics Engineers (IEEE), New York, N.Y., 89:29–34, 1989.

Fan and Harrison, "Micromachining of capillary electrophoresis injectors and separators on glass chips and evaluation of flow at capillary intersections," *Anal. Chem.*, 66:177–184, 1994.

Fodor, Rava, Huang, Pease, Holmes, Adams, "Multiplexed biochemical assays with biological chips," *Nature*, 364:555–556, 1993.

Folta, Raley, Hee, "Design. Fabrication and Testing of a Miniature Peristaltic Membrane Pump," *IEEE*, 186–189, 1992.

Fuhr, Hagedorn, Muller, Benecke, Wagner, "Pumping of water solution in microfabricated electrohydrodynamic systems," *Micro. Electro. Mech. Systems* 1992, Feb. 2–4, 1992.

Geankoplis, In: *Transport Processes and Unit Operations*, PTR™ Prentice-Hall, Inc. Englewood Cliffs, N.J., 1993.

Gerber, Miller, Schlosser, Steidley, Deutchrnan, "Position sensitive gamma ray detectors using resistive charge division readout," *IEEE Trans. Nuc. Sci.*, 24:182:187, 1977.

Gordon, Huang, Pentoney, Zare, "Capillary electrophoresis," *Science*, 242:224–228, 1988.

Gravensen, Branebjerg, Jensen, *J. Micromech. Microeng.*, 3:168–132, 1993.

Guatelli et al., *Proc. Natl. Acad. Sci.* USA, 87:1874–1878, 1990.

Hacia, Brody, Chee, Fodor, Collins, "Detection of heterozygous mutations in BRCA1 using high density oligonucleotide arrays and two-color fluorescence analysis," *Nature Genet.*, 14:441–449, 1996.

Harari, "Dielectric breakdown in electrically stressed thin films of thermal $SiO_2$," *J. Appl. Phys.*, 49:2478–2489, 1977.

Harrison, Fluri, Chiem, Tang, Fan, "Micromachining chemical and biochemical analysis and reaction systems on glass substrates," In: *Transducers, 1995—Eterosensors IX*, 752–755, Institute of Electrical and Electronics Engineers (IEEE), New York, N.Y., 1995.

Harrison, Fluri, Seiler, Fan, Effenhauser, Manz, In: *Science*, 261:895–897, 1993.

Harrison, Manz, Fan, Lüdi, Widmer, "Capillary electrophoresis and sample injection systems integrated on a planar glass chip," *Anal. Chem.*, 64:1926–1932, 1992a.

Harrison, Kurt, Manz, Zhoghui, "Chemical analysis and electrophoresis systems integrated on glass and silicon chips," *International Workshop on Solid-State Sensors and Actuators*, Hilton Head, 92:110–113, 1992b.

Heller and Tullis, "Microelectrophoresis for the separation of DNA fragments," *Electrophoresis*, 13:512–520, 1992.

Hynecek, "Theoretical analysis and optimization of CDS signal processing method for CCD image sensors," *IEEE Trans Electron Devices*, 39:2497–2507, 1992.

Jacobson and Ramsey, "Microchip electrophoresis with sample stacking," *Electrophoresis*, 16:481–486, 1995.

Jacobson and Ramsey, "Integrated microdevice for DNA restriction fragment analysis," Anal. Chem. 68:720–723, 1996.

Jacobson, Hergenröder, Koutny, Warmack, Ramsey, "Effects on injection schemes and column geometry on the performance of microchip electrophoresis devices," *Anal. Chem.*, 66:1107–1113, 1994a.

Jacobson, Hergenröder, Koutny, Ramsey. "High-speed separations on a microchip," *Anal. Chem.*, 66:1114–1118, 1994b.

Jacobson, Hergenröder, Koutny, Ramsey, "Open Channel Electrochromatography on a Microchip." *Anal Chem.* 66:2369–2373, 1994c.

Jorgenson and Lukacs, "High-resolution separations based on electrophoresis and electroosmosis," *J. Chromatography*, 218:209–216, 1981.

Kemmer, "Fabrication of low noise radiation detectors by the planar process," *Nuclear Inst. Meth.*, 169:499–502, 1980.

Knoll, In: *Radiation Detection and Measurement*, John Wiley & Sons, New York, 1979.

Knoll, In: *Radiation Detection and Measurement*, John Wiley & Sons, New York, 1989.

Kolb and Cerro, "Coating the inside of a capillary of square cross section," *Chemical Engineering Science*," 46:2181–2195, 1991.

Kuhr, "Capillary electrophoresis," *Anal Chem.*, 62:403R–414R, 1990.

Kwoh et al., *Proc. Natl. Acad Sci.*, USA, 86:1173–1177, 1989.

Lammerink, Elwenspoek, Fluitman, "Integrated microliquid dosing system," *International Workshop on Micro Electromechanical Systems* (MEMS), 93:254–259, 1993.

Lesser et al., *Science* 250:776, 1990.

Lintel, "A piezoelectric micropump based on micromachining of silicon," *Sensors Actuators*, 15:153–157, 1988.

Lizardi et al., In: *BioTechnology*, 6:1197–1202, 1988.

Macleod, In: *Thin-Film Optical Filters*. 2nd ed., Bristol: Hilger, 1986.

Manz, Effenhauser, Burggraf, Harrison, Seiler, Fluri, *J. Micromech. Microeng,.* 4:257–265, 1994.

Manz, Harrison, Fettinger, Verpoorte, Ludi, Widmer, "Integrated electroosmotic pumps and flow manifolds for total chemical analysis systems," *Transducers*," 91:939–941, 1991.

Manz, Harrison, Verpoorte, Fettinger, Paulus, Ludi, Widmer, "Planar chips technology for miniaturization and integration of separation techniques into monitoring systems: Capillary electrophoresis on a chip," *J. Chromatogr.*, 593:253–258, 1992.

Manz, Harrison, Verpoorte, Fettinger, Paulus, Ludi, Widmer, "Planar chips technology for miniaturization and integration of separation techniques into monitoring systems: Capillary electrophoresis on a chip," *J. Chromatogr.*, 593:253–258, 1992.

Manz, Verpoorte, Raymond, Effenhauser, Burggraf, Widmer, "µTAS: Miniaturized total chemical analysis," In: *Micro-total analysis systems*, 5–27, Kluwer Academic Publishers, Dordrecht, The Netherlands, 1995.

Mastrangelo and Muller, "Vacuum-sealed silicon micromachined incandescent light source," *Int. Electron Devices Meeting* IEDM, 89:503–506, 1989.

Mathes and Huang, "Capillary array electrophoresis: an approach to high-speed high-throughput DNA sequencing," *Nature*, 359:167–169, 1992.

Matsumoto and Colgate, "Preliminary Investigation of Micropumping Based on Electrical Control of Interfacial Tension," In: *International Workshop on Solid-State Sensors and Actuators*, Institute of Electrical and Electronics Engineers (IEEE), New York, N.Y., 105–110,1990.

McIntyre, "Microfabrication technology for DNA sequencing," *Trends Biotechnol.*, 14:91–95, 1996.

Middendorf, Bruce, Bruce, Eckles, Grone, Roemer, Sloniker, Steffens, Sutter, Brumbaugh, Patonay, "Continuous, on-line DNA sequencing using a versatile infrared laser scanner/electrophoresis apparatus," *Electrophoresis*, 13:487–494, 1992.

Miyake, Lammerink, Elwenspoek, Fluitman, "Micro mixer with fast diffusion," *International Workshop on Micro Electromechanical Systems* (MEMS), 93:248–253, 1993.

Mullis and Faloona, "The polymerase chain reaction," *Methods Enzymol.*, 155:335–350, 1987.

Nakagawa, Shoji, Esashi, "A micro chemical analyzing system integrated on a silicon wafer," *International Workshop on Solid-State Sensors and Actuators*, Hilton Head, 90:89–94, 1990.

Northrup, Ching, White, Watson, In: *Digest of Technical Papers: Transducers* 1993 (IEEE, New York), 924–926, 1993.

Northrup, Gonzalez, Hadley, Hillis, Landre, Lehew, Saiki, Sninsky, Watson, Watson Jr., "A MEMS-based miniature DNA analysis system," In: *Transducers 1995—Eumsensors IX*, Institute of Electrical and Electronics Engineers (IEEE), New York, N.Y., 94:764–767, 1994.

Ocvirk, Verpoorte, Manz, Widmer, "Integration of a micro liquid chromatograph onto a silicon chip," In: *Transducers 1995—Eurosensors IX*, Institute of Electrical and Electronics Engineers (IEEE), New York, N.Y., 95:756–759, 1995.

Ohnstein, Fukiura, Ridley, Bonne, "Micromachined silicon valve," *International Workshop on Solid-State Sensors and Actuators*, Hilton Head, 90:95–97, 1990.

Olsson, Enoksson, Stemme, Stemme, "A valve-less planar pump in silicon," In: *Transducers 1995—Eurosensors IX*, Institute of Electrical and Electronics Engineers (IEEE), New York, N.Y., 95:935–938, 1995.

Osipow, In: *Surface Chemistry: Theory and Industrial Applications*, Reinhold Publishing Corp., New York, pp. 7–21, 232–248, 1962.

Pentoncy, Konrad, Kaye, "Single-fluor approach to DNA sequence determination using high performance capillary electrophoresis," *Electrophoresis*, 13:467–474, 1992.

Petersen, "Silicon as a mechanical material," *IEEE Proceedings* 70:420–457, 1982.

Pfahler, Harley, Bau, Zemel, "Liquid transport in micron and submicron channels," *Sensors and Actuators*, A21–23:431–434, 1990.

Philipp, "Optical properties of silicon nitride," *J. Electrochem. Soc: Solid-State Science and Technology*, 120:295–300, 1993.

Pohl, In: *Dielectrophoresis*, Cambridge, Cambridge University Press, 1978.

Probstein, In: *Physicochemical Hydrodynamics*, Butterworth Publishers, Stoneham, Mass., 1989.

Ramsey, Jacobson, Knapp, "Microfabricated chemical measurement systems," *Nature Med.*, 1:1093–1096, 1995.

Roman, Matera, Cooper, Artandi, Blain, Ward, Calame, *Mol. Cell. Biol.*, 12:817–827, 1992.

Saiki et al., *Science*, 230:1350–1354, 1985.

Sambrook et al., "Molecular Cloning," *A Laboratory Manual*, 2d Ed., Cold Spring Harbor Laboratory Press, New York, 13.7–13.9, 1989.

Schena, Shalon, Davis, Brown, "Quantitative monitoring of gene expression patterns with a complementary DNA microarray," *Science*, 270:467–470, 1995.

Schoonevald, Audet, van Eijk, Gelsema, Hollander, Wouters, In: *Nuclear Instr. Methods Phys. Res.*, A305:581–586, 1991.

Shoffner et al., 1995.

Smits, "Piezoelectric micropump with three valves working peristaltically," *Sensors Actuators*, A21–A23: 203–206, 1990.

Spargo et al., *Molec. Cell. Probes*, 7:395–404, 1993.

Sun and Hartwick, "The effect of electric fields on the dispersion of oligonucleotides using a multipoint detection method in capillary gel electrophoresis," *J. Liquid Chrom.*, 17:1861–1875, 1994.

Swerdlow, Dew-Jaeger, Brady, Grey, Dovichi, Gesteland, "Stability of capillary gels for automated sequencing of DNA," *Electrophoresis*, 13:475–483, 1992.

Sze, "Current transport and maximum dielectric strength of silicon nitride films," *Journal of Applied Physics*, 38:2951–2956, 1967.

Sze, In: *Physics of Semiconductor Devices*, 2nd edition, John Wiley and Sons, New York, 852, 1981.

Tenan, Hackwood, Beni, *J. Appl. Phys.*, 53:6687–6692, 1982.

Terry, Herman, Angell, "A gas chromatographic air analyzer fabricated on a silicon wafer," *IEEE Trans. on Electron Devices* ED-26:1880–1886, 1979.

Thielking, et al., 1990. *Biochemistry* 29:4682.

Tickle, "*Thin-film transistors: a new approach to microelectronics*," John Wiley and Sons, New York, 1969.

Turner, "New dimensions in capillary electrophoresis columns," *Liquid Chrom. Gas Chrom*, 9:42–45, 1993.

U.S. Pat. No. 5,102,784
U.S. Pat. No. 5,451,500
U.S. Pat. No. 5,455,166
U.S. Pat. No. 5,470,723
U.S. Pat. No. 5,498,392, Wilding et al,
U.S. Pat. No. 5,587,128, Wilding et al.
U.S. Pat. No. 5,589,136, Northrup et al.
U.S. Pat. No. 5,639,423, Northrup et al.

Van den Berg, and Bergveld, In: *MESA Monograph: Micro Total Analysis Systems*, Kluwer Academic Publishers, Boston, 1995.

Van Lintel et al., *Sensors and Actuators*, 15:153–167, 1988.

Venditti & Wells, 1991. *J. Biol. Chem.* 266:16786.

Walker et al., *Proc. Natl. Acad. Sci. USA*, 89:392–396, 1992a.

Walker et al., *Nuc. Acids. Res.*, 20:1691–1696, 1992b.

Washizu, "Manipulation of biological objects in micromachined structures," *International Workshop on Micro Electromechanical Systems* (MEMS), 92:196–201, 1992.

Weber and May, "Abundant class of human polymorphisms which can be typed using the polymerase chain reaction," *Am. J. Hum. Genet.*, 44:388–396, 1989.

Webster and Mastrangelo, "Monolithic capillary gel electrophoresis stage with on-chip detector," *International Workshop on Micro Electromechanical Systems* (MEMS), Institute of Electrical and Electronics Engineers (IEEE), New York, N.Y., 96:491–496, 1996.

Wilding, Pfahler, Bau, Zemel, Kricka, "Manipulation and flow of biological fluids in straight channels micromachined in silicon," *Clin. Chem.*, 40:4347, 1994a.

Wilding, Shoffner, Kricka, "PCR™ in a silicon microstructure," *Clin. Chem.*, 40:1815–1818, 1994b.

Woolley and Mathies, "Ultra-high-speed DNA fragment separations using microfabricated capillary array electrophoresis chips," *Proc. Natl. Acad. Sci. USA*, 91:11348–11352, 1994.

Wooley and Mathies, "Ultra-high-speed DNA sequencing using capillary electrophoresis chips," *Anal. Chem.* 67:3676–3680,1995.

Wooley et al., 1996.

Wouters and van Sprakelaar, "Diffusion-based silicon nuclear radiation detectors with on-chip readout circuitry," *Nuclear Inst. Meth. Phys. Res.*, A326:299–303, 1993.

Wu et al., *Genomics*, 4:560–569; 1989.

Zeineh and Zeineh, "Miniature electrophoresis for speed and productivity," *Applied Biochemistry and Biotechnology*, 23:81–90, 1990.

Zengerle, Richter, Sandmaier, "A micro membrane pump with electrostatic actuation," *International Workshop on Micro Electromechanical Systems* (MEMS), 92:19–24, 1992.

---

What is claimed is:

1. A method for isothermal amplification of at least one selected nucleic acid, comprising:
   a) providing at least one sample comprising at least one selected nucleic acid, and reagents effective to permit at least one isothermal amplification reaction, to at least one microfabricated substrate that defines at least one channel, said channel connected to at least one isothermally regulated reaction chamber, wherein said sample is conveyed from said channel to said isothermally regulated reaction chamber by differential heating of said sample, wherein said substrate further comprises at least a second channel or at least one reservoir, wherein said at least a second channel or at least one reservoir is directly or indirectly connected to said at least one reaction chamber, wherein said reagents are prefabricated in a lyophilized form into said at least one reaction chamber, said at least one channel, said at least a second channel or said at least one reservoir; and
   b) conducting at least one isothermal amplification reaction to amplify said selected nucleic acid.

2. A method for isothermal amplification of at least one selected nucleic acid, comprising:
   a) providing at least one sample comprising at least one selected nucleic acid, and reagents effective to permit at least one isothermal amplification reaction, to at least one microfabricated substrate that defines at least one channel, said channel connected to at least one isothermally regulated reaction chamber, wherein said substrate comprises at least one flow-directing means system, wherein said flow-directing means system comprises at least one series of hydrophobic and hydrophilic surface structures arrayed along said channel; and
   b) conducting at least one isothermal amplification reaction to amplify said selected nucleic acid.

3. The method of claim 2, wherein said channel is treated with at least one hydrophilicity-enhancing compound.

4. The method of claim 2, wherein said channel is modified to comprise one or more hydrophobic regions.

5. The method of claim 1, wherein said microfabricated substrate further defines at least a one entry port connected to said at least one channel or said at least a second channel.

6. The method of claim 1, wherein said microfabricated substrate further defines at least a second channel directly or indirectly connected to said reaction chamber.

7. The method of claim 5, wherein said microfabricated substrate further defines at least a second entry port in operable connection with said at least a one channel or said at least a second channel.

8. The device of claim 6, wherein said at least a second channel is connected to said at least one channel at a point prior to connection of said at least one channel to said at least one reaction chamber.

9. The method of claim 1, wherein said microfabricated substrate further defines at least a first reservoir directly or indirectly connected to said at least one channel or to said at least one reaction chamber.

10. The method of claim 1, wherein said at least one microfabricated substrate is comprised of silicon, quartz or glass.

11. The method of claim 1, wherein said reagents comprise reagents for conducting a Strand Displacement Amplification reaction.

12. The method of claim 1, wherein said reagents comprise reagents for conducting a self-sustained sequence replication amplification reaction.

13. The method of claim 1, wherein said reagents comprise reagents for conducting a Qβ replicase amplification reaction.

14. The method of claim 1, wherein said reagents further comprise a DNA ligase.

15. The method of claim 1, wherein said reagents further comprise a nuclease.

16. The method of claim 15, wherein said reagents further comprise a restriction endonuclease.

17. The method of claim 1, wherein said sample is derived from an animal having or suspected of having a disease.

18. The method of claim 17, wherein said sample is derived from a human subject.

19. The method of claim 1, wherein said substrate comprises at least one replaceable cartridge.

20. The method of claim 19, wherein said replaceable cartridge comprises said at least one reservoir.

21. The method of claim 1, wherein said substrate further comprises at least one flow-directing means system in operable relation to said at least one channel.

22. The method of claim 21, wherein said flow directing means system comprises at least one series of heating elements.

23. The method of claim 22, wherein said heating elements are comprised of aluminum, platinum, gold or doped polysilicon.

24. The method of claim 21, wherein said flow-directing means system is separated from at least a first channel by a liquid barrier.

25. The method of claim 21, wherein said flow-directing means system comprises a gas source in fluid communication with said at least one channel.

26. The method of claim 25, wherein said gas source is at least one bubble pump.

27. The method of claim 21, wherein said flow-directing means system comprises at least one series of hydrophobic and hydrophilic surface structures arrayed along said channel.

28. The method of claim 27, wherein said channel is treated with at least one hydrophilicity-enhancing compound.

29. The method of claim 27, wherein said channel is modified to comprise one or more hydrophobic regions.

30. The method of claim 2, wherein said microfabricated substrate further defines at least a one entry port directly or indirectly connected to said first channel or said reaction chamber.

31. The method of claim 2, wherein said microfabricated substrate further defines at least a second entry port in operable connection with said at least one channel or said at least a second channel.

32. The method of claim 31, wherein said at least a second channel is connected to said at least one channel at a point prior to connection of said at least one channel to said reaction chamber.

33. The method of claim 32, wherein said microfabricated substrate further defines at least a one reservoir directly or indirectly connected to said at least a first channel or to said reaction chamber.

34. The method of claim 2, wherein said microfabricated substrate further defines at least a second channel directly or indirectly connected to said reaction chamber.

35. The method of claim 2, wherein said substrate further comprises at least one replaceable cartridge.

36. The method of claim 35, wherein said replaceable cartridge comprises said reservoir.

37. The method of claim 2, wherein said reagents are prefabricated into a component of said substrate.

38. The method of claim 37, wherein said reagents are prefabricated in a lyophilized form.

39. The method of claim 2, wherein said flow directing means system comprises at least one series of heating elements.

40. The method of claim 39, wherein said heating elements are comprised of aluminum, platinum, gold or doped polysilicon.

41. The method of claim 2, wherein said flow-directing means system is separated from said at least a first channel by a liquid barrier.

42. The method of claim 2, wherein said flow-directing means system comprises a gas source in fluid communication with said at least one channel.

43. The method of claim 42, wherein said gas source is at least one bubble pump.

44. The method of claim 2, wherein said microfabricated substrate is comprised of silicon, quartz or glass.

45. The method of claim 2, wherein said reagents comprise reagents for conducting a Strand Displacement Amplification reaction, a self-sustained sequence replication amplification reaction or a Qβ replicase amplification reaction.

46. The method of claim 2, wherein said reagents further comprise a DNA ligase, a nuclease or a restriction endonuclease.

47. The method of claim 2, wherein said sample is derived from an animal having or suspected of having a disease.

48. The method of claim 2, wherein said sample is derived from a human subject.

* * * * *

UNITED STATES PATENT AND TRADEMARK OFFICE
CERTIFICATE OF CORRECTION

PATENT NO. : 6,379,929 B1
DATED : April 30, 2002
INVENTOR(S) : Mark A. Burns et al.

It is certified that error appears in the above-identified patent and that said Letters Patent is hereby corrected as shown below:

Column 90,
Line 45, please delete "flow directing" and insert -- flow-directing -- therefor.
Line 52, after "from" please insert -- said -- therefor.

Signed and Sealed this

Fourteenth Day of January, 2003

JAMES E. ROGAN
*Director of the United States Patent and Trademark Office*

SEQUENCE LISTING (1) GENERAL INFORMATION:

(iii) NUMBER OF SEQUENCES: 6

(2) INFORMATION FOR SEQ ID NO:1:

(i) SEQUENCE CHARACTERISTICS:
       (A) LENGTH: 20 base pairs
       (B) TYPE: nucleic acid
       (C) STRANDEDNESS: single
       (D) TOPOLOGY: linear (xi) SEQUENCE DESCRIPTION: SEQ ID NO:1:

TAAGGTATGC CCCTGGCCAC                                        20

(2) INFORMATION FOR SEQ ID NO:2:

(i) SEQUENCE CHARACTERISTICS:
       (A) LENGTH: 21 base pairs
       (B) TYPE: nucleic acid
       (C) STRANDEDNESS: single
       (D) TOPOLOGY: linear (xi) SEQUENCE DESCRIPTION: SEQ ID NO:2:

AAGGTCAGCA CAGAGTCCTC A                                    21

(2) INFORMATION FOR SEQ ID NO:3:

(i) SEQUENCE CHARACTERISTICS:
       (A) LENGTH: 40 base pairs
       (B) TYPE: nucleic acid
       (C) STRANDEDNESS: single
       (D) TOPOLOGY: linear (xi) SEQUENCE DESCRIPTION: SEQ ID NO:3:

CGATTCCGCT CCAGACTTCT CGGGTCTACT GAGATCCCCT              40

(2) INFORMATION FOR SEQ ID NO:4:

(i) SEQUENCE CHARACTERISTICS:
       (A) LENGTH: 40 base pairs
       (B) TYPE: nucleic acid
       (C) STRANDEDNESS: single
       (D) TOPOLOGY: linear (xi) SEQUENCE DESCRIPTION: SEQ ID NO:4:

ACCGCATCGA ATGCATCTCT CGGGTAAGGC GTACTCGACC              40

(2) INFORMATION FOR SEQ ID NO:5:

(i) SEQUENCE CHARACTERISTICS:
       (A) LENGTH: 13 base pairs
       (B) TYPE: nucleic acid
       (C) STRANDEDNESS: single
       (D) TOPOLOGY: linear (xi) SEQUENCE DESCRIPTION: SEQ ID NO:5:

CGCTGAACCG GAT                                                    13

(2) INFORMATION FOR SEQ ID NO:6:

-continued

```
    (i) SEQUENCE CHARACTERISTICS:
        (A) LENGTH: 13 base pairs
        (B) TYPE: nucleic acid
        (C) STRANDEDNESS: single
        (D) TOPOLOGY: linear (xi) SEQUENCE DESCRIPTION: SEQ ID NO:6:

TCCACCCGCC AAC                                                            13
```